United States Patent [19]
Brown et al.

[11] Patent Number: 5,976,851
[45] Date of Patent: Nov. 2, 1999

[54] METHODS AND COMPOSITIONS FOR THE IDENTIFICATION, CHARACTERIZATION, AND INHIBITION OF FARNESYL PROTEIN TRANSFERASE

[75] Inventors: Michael S. Brown; Joseph L. Goldstein, both of Dallas, Tex.; Yuval Reiss, Tel-Aviv, Israel

[73] Assignee: Board of Regents, The University of Texas System, Austin, Tex.

[21] Appl. No.: 08/021,625

[22] Filed: Feb. 16, 1993

Related U.S. Application Data

[63] Continuation-in-part of application No. 07/822,011, Jan. 16, 1992, abandoned, which is a continuation-in-part of application No. PCT/US91/02650, Apr. 18, 1991, which is a continuation-in-part of application No. 07/615,715, Nov. 20, 1990, Pat. No. 5,141,851, which is a continuation-in-part of application No. 07/510,706, Apr. 18, 1990, abandoned.

[51] Int. Cl.$^6$ ........................................ C12N 9/10
[52] U.S. Cl. ................ 435/193; 435/69.1; 435/320.1; 435/172.3; 435/252.3; 435/252.33; 435/325; 435/363; 435/366; 435/91.1; 536/23.1; 536/23.2; 930/240; 935/14; 935/22; 935/29; 935/32; 935/70; 935/71; 935/72; 935/73
[58] Field of Search .................................. 435/69.1, 193, 435/320.1, 172.3, 240.2, 252.3, 252.33, 91, 325, 363, 366; 536/23.1, 23.2; 930/240; 935/14, 22, 29, 32, 70, 71, 72, 73

[56] References Cited

U.S. PATENT DOCUMENTS

| | | | |
|---|---|---|---|
| 4,675,285 | 6/1987 | Clark et al. | 435/6 |
| 5,026,554 | 6/1991 | Bartizal et al. | 514/452 |
| 5,043,268 | 8/1991 | Stock | 435/15 |
| 5,055,487 | 10/1991 | Bartizal et al. | 514/452 |
| 5,185,248 | 2/1993 | Barbacid | 435/15 |
| 5,202,456 | 4/1993 | Rando | 558/438 |
| 5,245,061 | 9/1993 | Singh | 554/121 |

FOREIGN PATENT DOCUMENTS

| | | |
|---|---|---|
| 0 456 180 | 11/1991 | European Pat. Off. . |
| 0 461 869 A2 | 12/1991 | European Pat. Off. . |
| 0 520 823 | 12/1992 | European Pat. Off. . |
| 0 523 873 | 1/1993 | European Pat. Off. . |
| 0 528 486 | 2/1993 | European Pat. Off. . |
| 0 535 730 | 4/1993 | European Pat. Off. . |
| 0 535 731 | 4/1993 | European Pat. Off. . |
| 2 261 373 | 5/1993 | United Kingdom . |
| 2 261 374 | 5/1993 | United Kingdom . |
| 2 261 375 | 5/1993 | United Kingdom . |
| WO 91/16340 | 10/1991 | WIPO . |
| WO 94/03597 | 2/1994 | WIPO . |
| WO 94/10184 | 5/1994 | WIPO . |

OTHER PUBLICATIONS

Nancy E. Kohl, et al., "Selective Inhibition of ras–Dependent Transformation by a Farnesyltransferase Inhibitor", *Science*, 260:1934–1937 (1993).

Clarke et al., "Posttranslational Modification of the Ha–ras oncogene Protein: Evidence for a Third Class of Protein Carboxyl Methyltransferases," *Proc. Natl. Acad. Sci. USA*, 85:4643–4647, 1988.

Hancock et al., "All ras Proteins Are Polyisoprenylated but Only come Are Palmitoylated," *Cell*, 57:1167–77, 1989.

Schafer et al., "Genetic and Pharmacological Suppression of Oncogenic Mutatins in RAS Genes of Yeast and Humans," *Science*, 245:379–385, 1989.

Bos, "ras Oncogenes in Human Cancer: A Review," *Cancer Research*, 49:4682–4689, 1989.

Lowy et al., "New Clue to Ras Lipid Glue," *Nature*, 341:384–85, 1989.

Casey et al., "p21ras Is Modified by a Farnesyl Isoprenoid," *Proc. Natl. Acad. Sci. USA*, 86:8323–8327, 1989.

Goldstein et al., "Regulation of the Mevalonate Pathway," *Nature*, 343:425–430, 1990.

Reiss et al., Inhibition of Purified p21$^{ras}$ Farnesyl:Protein Transferase by Cys–AAX Tetrapeptidesanne et al. *Cell*, 62:81–88, 1990.

Schaber et al., "Polyisoprenylaytion of Ras in Vitro by a Farnesyl–Protein Transferase," *J. Biolog. Chem.*, 265(25):14701–14704, 1990.

Manne et al., "Identification and Preliminary Characterization of Protein–Cysteine Farnesyltransferase," *Proc. Natl. Acad. Sci. USA*, 87:7541–7545, 1990.

Reiss et al., "Sequence Requirement for Peptide Recognition by Rat Brain p21$^{ras}$ Protein Farnesyltransferase," *Proc. Natl. Acad. Sci. USA*, 88:732–736, 1991.

Chen, et al., "cDNA Cloning and Expression of the Peptide–Binding β Subunit of Rat p21$^{ras}$ Farnesyltransferase, the Counterpart of Yeast DPR1/RAM1," *Cell*, 66:327–334, 1991.

Goldstein, et al., "Nonfarnesylated Tetrapeptide Inhibitors of Protein Farnesyltransferase," *J. Biol. Chem.*, 266(24):15575–15578, 1991.

(List continued on next page.)

*Primary Examiner*—Christopher S. F. Low
*Attorney, Agent, or Firm*—Arnold, White & Durkee

[57] ABSTRACT

Disclosed are methods and compositions for the identification, characterization and inhibition of mammalian farnesyl protein transferases, enzymes involved in the farnesylation of various cellular proteins, including cancer related ras proteins such as p21$^{ras}$. The nucleotide and amino acid sequences of the α and β subunits of both rat and human farnesyl transferase are disclosed, as are methods and compositions for the preparation of farnesyl transferase by recombinant means, following the molecular cloning and co-expression of its two subunits, for assay and purification of the enzyme, as well as procedures for using the purified enzyme in screening protocols for the identification of possible anticancer agents which inhibit the enzyme and thereby prevent expression of proteins such as p21$^{ras}$. Also disclosed is a families of compounds which act either as false substrates for the enzyme or as pure inhibitors and can therefore be employed for inhibition of the enzyme. The most potent inhibitors are ones in which phenylalanine occurs at the third position of a tetrapeptide whose amino terminus is cysteine.

36 Claims, 34 Drawing Sheets

OTHER PUBLICATIONS

Goodman, et al., "Structure and Expression of Yeast DPR1, a Gene Essential for the Processing and Intracellular Localization of ras Proteins," *Yeast*, 4:271–281, 1988.

Goodman, et al., "Mutants of *Saccharomyces cerevisiae* Defective in the Frnesylation of Ras Proteins," *Proc. Natl. Acad. Sci.*, 87:9665–9669, 1990.

Schaber, et al., "Polyisoprenylation of Ras in Vitro by a Farnesyl–Protein Transferase," *Chem. Abstr.*, 114:302, Abstract # 38170r, 1991.

Kim, et al., "Prenylation of Mammalian Ras Protein in Xenopus Oocytes," *Chem. Abstr.*, 114:373, Abstract # 3711r, 1991.

Kohl et al., "Structural Homology Among Mammalian and *Saccharomyces cerevisiae* Isoprenyl–protein Transferases," *J. Biol. Chem.*, 266(28):1884–18888, 1991.

He et al., "RAM2, an essential gene of yeast, and RAM1 encode the two polypeptide components of the farnesyltransferase that prenylates a–factor and Ras proteins," *PNAS*, 88:11373–11377, 1991.

Reiss, et al., "Divalent Cation and Prenyl Pyrophosphate Specificities of the Protein Farnesyltransferase from Rat Brain, a Zinc Metalloenzyme," *J. Biol. Chem.*, 267:6403–6408, 1992. Published in USA.

Seabra, et al., "Protein Farnesyltransferase and Geranylgeranyltransferase Share a Common α Subunit," *Cell*, 65:429–434, 1991. Published in USA.

Reiss, et al., "Purification of ras Farnesyl:Protein Transferase," *Methods: A Companion to Methods in Enzymology*, 1(3):241–245, 1990. Published in USA.

*Webster's II New Riverside University Dictionary*, 1984, Houghton Mifflin Co., Boston, MA, pp. 1056–1057.

Stryer, L. 1975, in: *Biochemistry*, W. H. Freeman and Compamy, San Francisco, CA, p. 595.

Dudov et al., 1984, Cell 37, 457–468.

Sambrook et al., 1989 *Molecular Cloning, A Laboratory Manual*, Second Edition, Cold Spring Harbor Laboratory Press, Cold Spring Harbor, NY, pp. XVIXVIII, and 9.2–9.62.

Watson, J.D. 1987. In: *Molec. Biol. of the Gene.* 3rd Edition. Benjamin/Cummings Publ. Co.. Membo Park, CA, p. 313.

Strickberger, M. 1976, in *Genetics.*Second Edition. Macmillan Publ. Co. Inc., NY. p. 484.

Day, R. A. 1983. in: How to write and Publsih a Scientific Paper. Second Edition. ISI Press., Philadelphia pp. 15–19.

```
PCR Primer α1 →
     T       A T
GAC GCI ATI GAG CTA AAC GCA GCC AAC TAT ACG GTC TGG CAC TT
Asp Ala Ile Glu Leu Asn Ala Ala Asn Tyr Thr Val Trp His Phe Arg
        (SEQ. ID NO: 59)              (SEQ. ID NO: 58) CAI ACC GTA AAA TC
                                                               G      G  G
                                                       ← PCR Primer α2
```

(SEQ. ID NO: 57)

FIG. 16A

RAT FT-α   1 MAATEGVGESAPGGEPGQPEQPPPPPAQQPQEEMAAEAGFAAASP
          51 MDDGFLSLDSETYVLYRDRAEWADIDFVPQNDGPSPVVQIMSEKFRDVY
         101 DYERAVLQRDERSERAFKLIRDAIELNAANYTVWHFRRVIRSIQKDLQE
         151 EMNYIAIIEEQPKNYQVWHHRRVLVEWLKDPS--QELEFIADILNQDAK
         199 NYHAWQHRQWVIQEFRLWDNELQYVDQLKEDVRNNSVWNQRHFVISNTT
         249 GYSDRAVLEREVQYTLEMIKLVBHNFSAWNYIKG--IL-QDR--GISRY
         293 PNLLNQLID-L-QPSHSSPYLIAFLVDIYEDMLENQCDNKEDILNKALEL
         341 CEILAKEKDIIRKEYWRYIGRSLQSKHSRESDIPASV  377 (SEQ. ID NO:1)

FIG. 17

Rat FT-β  1    M--ASSSS------E-TYYCPPSSSPV---WSEPLYSLRPEHARERTQDDSV

41   ETVISIEQAKVEEKIQEVFSSYKFNHLVPRLVLQREKHFHYL-KRGLRQLTDAYECLDAS

100   RPWLCYWILHSIELIDEPIPQIVADVCQFLEL-CQSPDGG-EGGGPGQYPHLAPTYAAV

158   NAL-CIIGTEEAYNVINBEKLIDYLYSLKQPDGSE-LMHVGGEVDVRSAYCAASVESIIN

216   IIIPDLFEGTAEWIARCQNWEGGIGGVB-GMEAHGGYTFCGLIAALVILKKERSINLKSLL

275   QWVTSRQMRFEGEQGRCNKLVDGCYSFWQAGLLPLLHRALHAQGDPALSMSHWMEHQQA

335   LPEYIIMCCQ--CPAGGLLDKPGKSRDFYHTQYCLSGISIAQHFGSGAMLHCVVMGVPENV

394   LQEHEVYNIGPDK-VIQATTHEL-QKHVPGFEECEDAVTSDPATD  437  (SEQ. ID NO: 3)

FIG. 18

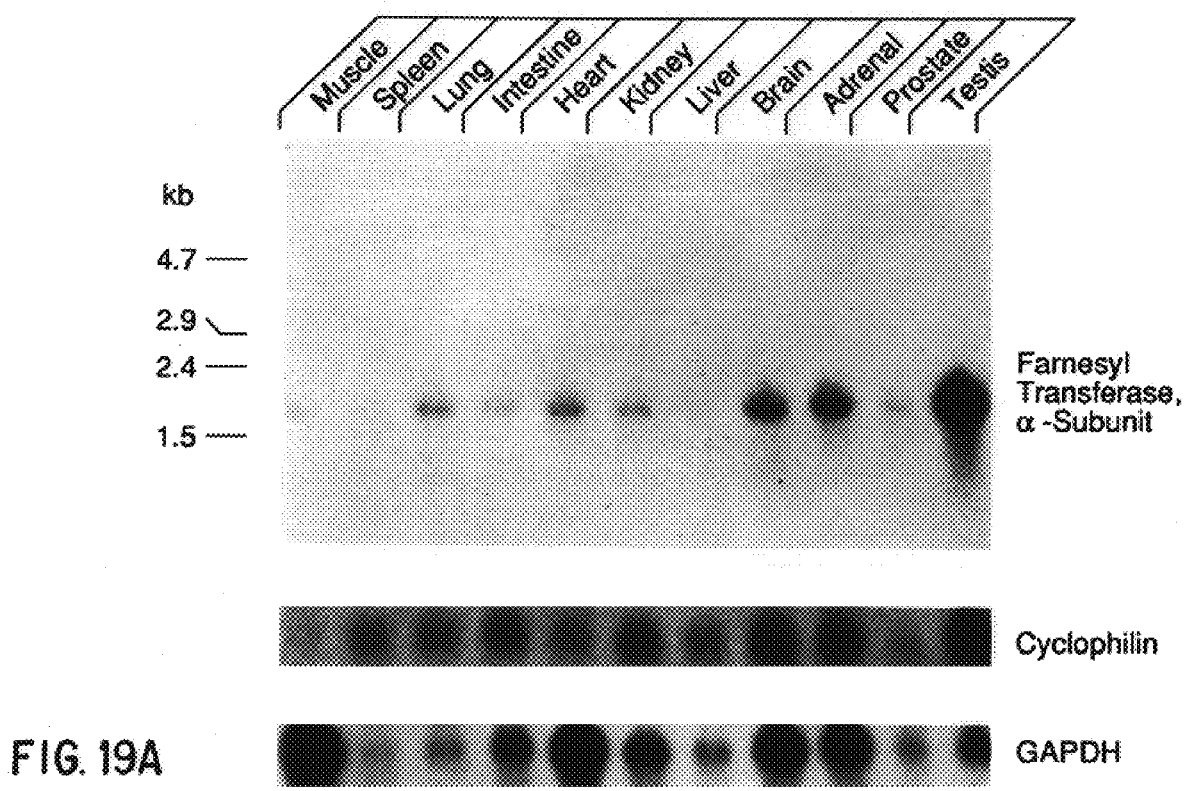

```
GGCGAGATGGCGGCCACCGAGGGGTCGGGGGAGGCTGGGCAAGGGGGCGAGCCCGGGCAG         60
        MetAlaAlaThrGluGlyValGlyGlyGluAlaGlnGlyGlyGluProGlyGln         18
                                              Ser    Pro

CCGGCGCAACCCCCGCCCCAGCCGCCACCCCCCAGCCGCCGCCAGCAGCACAAGGAAGAG        120
ProAlaGlnProProProGlnProHisProProProGlnGlnGlnHisLysGluGlu         38
   Glu                   Pro           Pro    Ala    ProGlnGlu

ATGGCGGCCGAGGCTGGGGAAGCCGTGGCGGTCCCCATGGACGACGGGTTTGTGAGCCTG        180
MetAlaAlaGlyAlaGlyGluAlaGlyGlyGluAlaValAlaSerProMetAspAspGlyPheValSerLeu   58
                                   Ala                          Leu

GACTCGCCCCTCCTATGTCCTGTACAGGGACAGAGAGCAGAATGGGGCTGATATAGATCCGGTG    240
AspSerProSerTyrValLeuTyrArgAspArgGluGlnAsnGlyAlaAspIleAspProVal         78
          Thr

CCGCAGAATGATGGCCCCAATCCCGTGGTCCAGATCATTTATAGTGACAAATTTAGAGAT       300
ProGlnAsnAspGlyProAsnProValValGlnIleIleTyrSerAspLysPheArgAsp         98
                  Ser                        Glu

GTTTATGATTACTTCCGAGCTGTCCTGCAGCGTGATGAAAGAAGTGAACGAGCTTTTAAG       360
ValTyrAspTyrPheArgAlaValLeuGlnArgAspGluArgSerGluArgAlaPheLys        118
```

FIG. 23A

```
CTAACCCGGGATGCTATTGAGTTAAATGCAGCCAATTATACAGTGTGGCATTTCCGGAGA         420
LeuThrArgAspAlaIleGluLeuAsnAlaAlaAsnTyrThrValTrpHisPheArgArg         138

GTTCTTTTGAAGTCACTTCAGAAGGATCTACATGAGGAAATGAACTACATCACTGCAATA         480
ValLeuLeu[Lys]SerLeuGlnLysAspLeu[His]GluMetAsnTyrIle[Thr]AlaIle       158
         Arg                  Gln                    Ile

ATTGAGGAGCAGCCCAAAAACTATCAAGTTTGGCATCATAGGCGAGTATTAGTGGAATGG         540
IleGluGluGlnProLysAsnTyrGlnValTrpHisHisArgArgValLeuValGluTrp         178

CTAAGAGATCCATCTCAGGAGCTTGAATTTATTGCTGATATTCTTAATCAGGATGCAAAG         600
Leu[Arg]AspProSerGlnGluLeuGluPheIleAlaAspIleLeuAsnGlnAspAlaLys       198
    Lys

AATTATCATGCCTGGCAGCATCGACAATGGGTTATTCAGGAATTTAAACTTTGGGATAAT         660
AsnTyrHisAlaTrpGlnHisArgGlnTrpValIleGlnGluPhe[Lys]LeuTrpAspAsn       218
                                              Arg

GAGCTGCAGTATGTGGACCAACTTCTGAAAGAGGATGTGAGAAATAACTCTGTCTGGAAC         720
GluLeuGlnTyrValAspGlnLeuLeuLysGluAspValArgAsnAsnSerValTrpAsn         238

CAAAGATACTTCGTTATTCTAACACCACTGGCTACAATGATCGTGCTGTATTGGAGAGA         780
GlnArg[Tyr]PheValIleSerAsnThrThrGlyTyr[Asn]AspArgAlaValLeuGluArg     258
       His                              Ser
```

FIG. 23B

```
GAAGTCCAATACACTCTGGAAATGATTAAACTAGTACCACATAATGAAAGTGCATGGAAC      840
GluValGlnTyrThrLeuGluMetIleLysLeuValProHisAsnGluSerAlaTrpAsn      278

TATTGAAAGGGATTTTGCAGGATCGTGGTCTTTCCAAATATCCTAATCTGTTAAATCAA       900
TyrLeuLysGlyIleLeuGlnAspArgGlyLeuSer[Lys]TyrProAsnLeuLeuAsnGln    298
                                   [Arg]

TTACTTGATTTACAACCAAGTCATAGTTCCCCTACTAATTGCCTTTCTTGTGGATATC        960
LeuLeuAspLeuGlnProSerHisSerSerProTyrLeuIleAlaPheLeuValAspIle      318

TATGAAGACATGCTAGAAAATCAGTGTGACAATAAGGAAGACATTCTTAATAAAGCATTA    1020
TyrGluAspMetLeuGluAsnGlnCysAspAsnLysGluAspIleLeuAsnLysAlaLeu     338

GAGTTATGTGAAATCCTAGCTAAAGAAAAGGACACTATAAGAAAGGAATATTGGAGATAC   1080
GluLeuCysGluIleLeuAlaLysGluLysAspThrIleArgLysGluTyrTrpArgTyr     358

ATTGGAAGATCCCTTCAAAGCAAACACAGACACCAGAAAATGACTCACCAACAAATGTACAG 1140
IleGlyArgSerLeuGlnSerLysHisSer[Thr]Glu[Asn]AspSerPro[Thr]AsnVal[Gln]  378
                              [Arg]    [Ser]   [Ile]   [Ala]Ser[End]

CAATAACACCATCCAGAAGAACTTGATGGAATGCTTTATTTTTATTTAAGGGACCCTGC    1200
Gln(SEQ. ID NO:3)                                                379
```

FIG. 23C

```
AGGAGTTTCACACGAGAGTGGTCCTTCCCTTGCCTGTGGTGTAAAAGTGCATCACACAG        1260

GTATTGCTTTTAACAAGAACTGATGCTCCTTGGGTGCTGCTGCTACTCAGACTAGCTCT        1320

AAGTAATGTGATTCTTCTAAAGCAAAGTCATTGGATGGGAGGAGGAAGAAAAAGTCCAT        1380

AAAGGAACTTTTGTAGTCTTATCAACATATAATCCCTTAGCATCAGTCCTCCCT             1440

CAGTGGTACATGCGTCAAGATTTGTAGCAGTAATAACTGCAGGTCACTTGTATGTAATGG      1500

ATGTGAGGTAGCCGAAGTTTGGTTCAGTAAGCAGGAATACAGTCGTTCCATCAGAGCTG       1560

GTCTGCACACTCACATTATCTTGCTATCACTGTAACCAACTAATGCCAAAGAACGGTTT       1620

TGTAATAAAATTATAGCTGTATCTAAAAAAAAAAAAAAAAAAAAA (SEQ. ID NO:6)      1670
```

FIG. 23D

```
GTAGAAGAAAAGATCCAAGAGGTCTTCAGTTCTTACAAGTTCAACCACCTTGTACCAAGG  60
ValGluGluLysIleGlnGluValPheSerSerTyrLysPheAsnHisLeuValProArg  20

CTTGTTTTGCAGAGGGAGAAGCACTTCCATTATCTGAAAAGAGGCCTTCGACAACTGACA  120
LeuValLeuGlnArgGluLysHisPheHisTyrLeuLysArgGlyLeuArgGlnLeuThr  40

GATGCCTATGAGTGTCTGGATGCCAGCCGCCCATGGCTCTGCTATTGGATCCTGCACAGC  180
AspAlaTyrGluCysLeuAspAlaSerArgProTrpLeuCysTyrTrpIleLeuHisSer  60

TTGGAACTGCTAGATGAACCCATCCCCCAGATAGTGGCTACAGATGTGTCAGTTCCTG  240
LeuGluLeuAspGluProIleProGlnIleValAlaThrAspValCysGlnPheLeu  80

GAGCTGTGTCAGAGCCCAGAAGGTGGCTTTGGAGGAGACCCGGTCAGTATCCACACCTT  300
GluLeuCysGlnSerProGluGlyGlyPheGlyGlyGlyProGlyGlnTyrProHisLeu  100
                     Asp

GCACCCACATATGCAGCAGTCAATGCATTGTGCATCATTGGCACCGAGAGGCCTATGAC  360
AlaProThrTyrAlaAlaValAsnAlaLeuCysIleIleGlyThrGluAlaTyrAspAsn  120
                                                        Asn

ATCATTAACAGAGAGAAGCTTCTTCAGTATTTGTACTCCCTGAAGCAACCTGACGGCTCC  420
IleIleAsnArgGluLysLeuLeuGlnTyrLeuTyrSerLeuLysGlnProAspGlySer  140
Val
```

FIG. 24A

```
TTTCTCATGTCGGAGGTGAGGTGGATGTGAGAAGCGCATACTGTGCTGCCTCCGTA                480
PheLeuMetHisValGlyGlyGluValAspValArgSerAlaTyrCysAlaAlaSerVal            160

GCCTGCTGACCAACATCATCACTCCAGACCTCTTTGAGGGCACTGCTGAATGGATAGCA            540
AlaSerLeuThrAsnIleIleThrProAspLeuPheGluGlyThrAlaGluTrpIleAla            180

AGGTGTCAGAACTGGGAAGGTGGCATTGGCGGGGTACCAGGGATGGAAGCCCATGGTGGC            600
ArgCysGlnAsnTrpGluGlyGlyIleGlyGlyValProGlyMetGluAlaHisGlyGly            200

TATACCTTCTGTGGCCTGGCCCGCTGGTAATCCTCAAGAGGGAACGTTCCTTGAACTTG            660
TyrThrPheCysGlyLeuAlaAlaLeuValIleLeuLysArgGluArgSerLeuAsnLeu            220
                                         Lys

AAGAGCTTATTACAATGGGTGACAAGCCGGACAGATGCTATTTGAAGGAGGATTTCAGGGC          720
LysSerLeuLeuGlnTrpValThrSerArgGlnMetLeuPheGluGlyGlyPheGlnGly            240
                                    Arg

CGGCTGCAACAAGCTGGTGGTGGATGGCTGCTACTCCTTCTGGCAGGCGGGGCTCCTGCCCCTG       780
ArgCysAsnLysLeuValAspGlyCysTyrSerPheTrpGlnAlaGlyLeuLeuProLeu            260

CTCCACCGGCACTGCACGCCCAAGGTGACCCTTAGCACATGAGCCACTGGATGTTC                840
LeuHisArgAlaLeuHisAlaGlnGlyAspProAlaLeuSerMetSerHisTrpMetPhe            280
```

FIG. 24B

```
CATCAGCAGGCCCTGCAGGAGTACATCCTGATGTGCTGCCAGTGCCTGCGGGGGGCTT     900
HisGlnGlnAlaLeuGlnGluTyrIleLeuMetCysCysGlnCysProAlaGlyGlyLeu   300

CTGGATAAACCTGGCCAAGTGCGGTGATTTCTACCACACCTGCTACTGCCTGAGCGGCCTG  960
LeuAspLysProGlyLysSerArgAspPheTyrHisThrCysTyrCysLeuSerGlyLeu   320

TCCATAGCCCAGCACTTCGGCAGCGGAGCCATGTTGCATGATGTGGTCCTGGGTGTGCCC   1020
SerIleAlaGlnHisPheGlySerGlyAlaMetLeuHisAspValVal LeuGlyValPro  340
                                                 Met

GAAAACGCTCTGCAGCCCACTCACCCAGTGTACAACATTGGACCAGACAAGGTGATCCAG   1080
GluAsn AlaLeuGlnProThrHisProValTyrAsnIleGlyProAspLysValIleGln 360
       Val

GCCACTACATACTTTCTACAGAAGCCAGTCCCAGGTTTTGAGGAGCTTAAGGATGAGACA   1140
AlaThrThr TyrPheLeuGlnLysProValProGlyPheGluGluLeuLysAspGluThr 380
          His                                CysGlu  AlaVal

TCGGCAGAGCCTGCAACCGACTAGAGGAGGACCTGGGTCCCGGCAGCTCTTTGCTCACCCATC  1200
SerAlaGluProAlaThrAsp    (SEQ. ID NO:7)                         387
ThrSerAsp

TCCCCAGTCAGACAAGGTTTATAGGTTTCAATACATACTGCATTCTGT    (SEQ. ID NO:8)  1248
```

FIG. 24C

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 18 amino acids
      (B) TYPE: amino acid
      (C) STRANDEDNESS: single
      (D) TOPOLOGY: linear (xi) SEQUENCE DESCRIPTION: SEQ ID NO:1:

```
Glu Trp Ser Pro Cys Ser Val Thr Cys Gly Asn Gly Ile Gln Val Arg
1               5                   10                  15

Ile Lys
```

(2) INFORMATION FOR SEQ ID NO:2:

(i) SEQUENCE CHARACTERISTICS:
      (A) LENGTH: 23 amino acids
      (B) TYPE: amino acid
      (C) STRANDEDNESS: single
      (D) TOPOLOGY: linear (xi) SEQUENCE DESCRIPTION: SEQ ID NO:2:

Glu Trp Ser Pro Cys Ser Val Thr Cys Gly Asn Gly Ile Gln Val Arg
1               5                   10                  15

Ile Lys Pro Gly Ser Ala Asn
            20

(2) INFORMATION FOR SEQ ID NO:3:

(i) SEQUENCE CHARACTERISTICS:
      (A) LENGTH: 23 amino acids
      (B) TYPE: amino acid
      (C) STRANDEDNESS: single
      (D) TOPOLOGY: linear (xi) SEQUENCE DESCRIPTION: SEQ ID NO:3:

Gly Asn Glu Ile Glu Pro Gly Asn Asn Ala Tyr Gly Ser Gln Ser Asp
1               5                   10                  15

Thr Asp Ala Ser Glu Leu Thr
            20

(2) INFORMATION FOR SEQ ID NO:4:

(i) SEQUENCE CHARACTERISTICS:
      (A) LENGTH: 126 amino acids
      (B) TYPE: amino acid
      (C) STRANDEDNESS:
      (D) TOPOLOGY: linear (xi) SEQUENCE DESCRIPTION: SEQ ID NO:4:

Asn Ala Asn Pro Asn Val Asp Pro Asn Ala Asn Pro Asn Val Asp Pro
1               5                   10                  15

Asn Ala Asn Pro Asn Val Asp Pro Asn Ala Asn Pro Asn Ala Asn Pro
            20                  25                  30

Asn Ala Asn Pro Asn Ala Asn Pro Asn Ala Asn Pro Asn Ala Asn Pro
        35                  40                  45

Asn Ala Asn Pro Asn Ala Asn Pro Asn Ala Asn Pro Asn Ala Asn Pro
    50                  55                  60

Asn Ala Asn Pro Asn Ala Asn Pro Asn Ala Asn Pro Asn Ala Asn Pro
65              70                  75                  80

Asn Ala Asn Pro Asn Ala Asn Pro Asn Ala Asn Pro Asn Ala Asn Pro
            85                  90                  95

Asn Ala Asn Pro Asn Ala Asn Pro Asn Ala Asn Pro Glu Trp Ser Pro
                100                 105                 110

Cys Ser Val Thr Cys Gly Asn Gly Ile Gln Val Arg Ile Lys
            115                 120                 125

(2) INFORMATION FOR SEQ ID NO:5:

(i) SEQUENCE CHARACTERISTICS:
      (A) LENGTH: 46 amino acids
      (B) TYPE: amino acid
      (C) STRANDEDNESS:
      (D) TOPOLOGY: linear (xi) SEQUENCE DESCRIPTION: SEQ ID NO:5:

Asn Ala Asn Pro Asn Val Asp Pro Asn Ala Asn Pro Asn Val Asp Pro
1               5                   10                  15

Asn Ala Asn Pro Asn Val Asp Pro Asn Ala Asn Pro Glu Trp Ser Pro
            20                  25                  30

Cys Ser Val Thr Cys Gly Asn Gly Ile Gln Val Arg Ile Lys
        35                  40                  45

METHODS AND COMPOSITIONS FOR THE IDENTIFICATION, CHARACTERIZATION, AND INHIBITION OF FARNESYL PROTEIN TRANSFERASE

This application is a continuation-in-part of U.S. Ser. No. 07/822,011, filed Jan. 16, 1992, now abandoned; which was a continuation-in-part of copending PCT application, US 91/02650, filed Apr. 18, 1991; which was a continuation-in-part of U.S. Ser. No. 07/615,715, filed Nov. 20, 1990, now U.S. Pat. No. 5,141,851; which was a continuation-in-part of U.S. Ser. No. 07/510,706, filed Apr. 18, 1990, now abandoned.

The government owns certain rights in the present invention pursuant to NIH grant numbers 5-PO1-HL20948, HL20948, HG00298 and T32 GM08404.

BACKGROUND OF THE INVENTION

1. Field of the Invention

This invention relates to the molecular cloning, purification, characterization and inhibition of farnesyl:protein transferase, an enzyme involved in expression of the cancer phenotype, for example, in the transfer of farnesyl groups to oncogenic ras proteins. In particular aspects, the invention relates to nucleic acid segments encoding mammalian enzyme subunits which can be used as probes for the selection of related sequences or in the production of the holoenzyme or subunit polypeptides thereof, to the purification of the native or recombinant enzyme, as well as to assay methods for the identification of candidate substances which will inhibit the activity of the enzyme.

2. Description of the Related Art

In recent years, some progress has been made in the elucidation of cellular events lending to the development or progression of various types of cancers. A great amount of research has centered on identifying genes which are altered or mutated in cancer relative to normal cells. In fact, genetic research has led to the identification of a variety of gene families in which mutations can lead to the development of a wide variety of tumors. The ras gene family is a family of closely related genes that frequently contain mutations involved in many human tumors, including tumors of virtually every tumor group (see, e.g., Bos, 1989). In fact, altered ras genes are the most frequently identified oncogenes in human tumors (Barbacid, 1987).

The ras gene family comprises three genes, H-ras, K-ras and N-ras, which encode similar proteins with molecular weights of about 21,000 (Barbacid, 1987). These proteins, often termed $p21^{ras}$, comprise a family of GTP-binding and hydrolyzing proteins that regulate cell growth when bound to the inner surface of the plasma membrane (Hancock, et al., 1989; Scheler et al., 1989). Overproduction of $P21^{ras}$ proteins or mutations that abolish their GTP-ase activity lead to uncontrolled cell division (Gibbs et al., 1989). However, the transforming activity of ras is dependent on the localization of the protein to membranes, a property thought to be conferred by the addition of farnesyl groups (Hancock et al., 1989; Casey et al., 1989).

A precedent for the covalent isoprenylation of proteins had been established about a decade ago when peptide mating factors secreted by several fungi were shown to contain a farnesyl group attached in thioether linkage to the C-terminal cysteine (Kamiya et al., 1978; 1979; Sakagami et al., 1981). Subsequent studies with the mating a-factor from *Saccharomyces cerevisiae* and farnesylated proteins from animal cells have clarified the mechanism of farnesylation. In each of these proteins the farnesylated cysteine is initially the fourth residue from the C terminus (Hancock, et al., 1989; Scheler et al., 1989; Gutierrez et al., 1989). Immediately after translation, in a sequence of events whose order is not yet totally established, a farnesyl group is attached to this cysteine, the protein is cleaved on the C-terminal side of this residue, and the free COOH group of the cysteine is methylated (Hancock et al., 1989; Gutierrez et al., 1989; Lowry et al., 1989; Clarke et al., 1988). All of these reactions are required for the secretion of active a-factor in Saccharomyces (Scheler et al., 1989).

Most, if not all, of the known $p21^{ras}$ proteins contain the cysteine prerequisite, which is processed by farnesylation, proteolysis and COOH-methylation, just as with the yeast mating factor (Hancock et al., 1989; Scheler et al., 1989; Gutierrez et al., 1989; Lowry et al., 1989; Clarke et al., 1988). The farnesylated $p21^{ras}$ binds loosely to the plasma membrane, from which most of it can be released with salt (Hancock, et al., 1989). After binding to the membrane, some $P21^{ras}$ proteins are further modified by the addition of palmitate in thioester linkage to cysteines near the farnesylated C-terminal cysteine (Hancock et al., 1989). Palmitylation renders the protein even more hydrophobic and anchors it more tightly to the plasma membrane.

However, although it appears to be clear that farnesylation is a key event in ras-related cancer development, prior to now, the nature of this event has remained obscure. Nothing has been known previously, for example, of the nature of the enzyme or enzymes which may be involved in ras tumorigenesis or required by the tumor cell to achieve farnesylation. If the mechanisms that underlie farnesylation of cancer-related proteins such as $P21^{ras}$ could be elucidated, then procedures and perhaps even pharmacologic agents could be developed in an attempt to control or inhibit expression of the oncogenic phenotype in a wide variety of cancers. It goes without saying that such discoveries would be of pioneering proportions in cancer therapy.

SUMMARY OF THE INVENTION

The present invention addresses one or more shortcomings in the prior art through the identification and characterization of an enzyme, termed farnesyl:protein transferase or CAAX farnesyltransferase, involved in the oncogenic process through the transfer of farnesyl groups to various proteins including oncogenic ras proteins. The invention relates particularly to the molecular cloning of mammalian farnesyl:protein transferase subunits, to the purification of the native or recombinant enzyme, to protein and peptide substances that are capable of inhibiting the enzyme, and to assay methods for the identification of further inhibitory compounds.

A certain object of the present invention is therefore to provide ready means for obtaining farnesyl transferase enzymes, by purification of the native enzyme from tissues of choice, or by purification of the recombinant enzyme from host cells that express the constituent subunits, which methods are proposed to be generally applicable to the purification of all such farnesyl protein transferases.

It is an additional object of the invention to provide means for obtaining these enzymes in a relatively purified form, allowing their use in predictive assays for identifying compounds having the ability to reduce the activity of or inhibit the farnesyl transferase activity, particularly in the context of p21$^{ras}$ proteins.

It is a still further object of the invention to identify classes of compounds which demonstrate farnesyl transferase inhibiting activity, along with a potential application of these compounds in the treatment of cancer, particularly ras-related cancers.

Farnesyl:Protein Transferase Characterization

Accordingly, in certain embodiments, the present invention relates to compositions which include a purified farnesyl protein transferase (CAAX farnesyltransferase) enzyme, characterized as follows:

a) capable of catalyzing the transfer of farnesyl to a protein or peptide having a farnesyl acceptor moiety;

b) capable of binding to an affinity chromatography medium comprised of TKCVIM (seq id no:9) coupled to a suitable matrix;

c) exhibiting a molecular weight of between about 70,000 and about 100,000 upon gel filtration chromatography; and d) having a farnesyl transferase activity that is capable of being inhibited by one of the following peptides:
   i) TKCVIM (seq id no:9);
   ii) CVIM (seq id no:10); or
   iii) KKSKTKCVIM (seq id no:11).

As used herein, the phrase "capable of catalyzing the transfer of farnesol to a protein or peptide having a farnesyl acceptor moiety," is intended to refer to the functional attributes of farnesyl transferase enzymes of the present invention, which catalyze the transfer of farnesol, typically in the form of all-trans farnesol, from all-trans farnesyl pyrophosphate to proteins which have a sequence recognized by the enzyme for attachment of the farnesyl moieties. Thus, the term "farnesyl acceptor moiety" is intended to refer to any sequence, typically a short amino acid recognition sequence, which is recognized by the enzyme and to which a farnesyl group will be attached by such an enzyme.

Farnesyl acceptor moieties have been characterized by others in various proteins as a four amino acid sequence found at the carboxy terminus of target proteins. This four amino acid sequence has been characterized as -C-A-A-X (seq id no:12), wherein "C" is a cysteine residue, "A" refers to any aliphatic amino acid, and "X" refers to any amino acid. Of course, the term "aliphatic amino acid" is well-known in the art to mean any amino acid having an aliphatic side chain, such as, for example, leucine, isoleucine, alanine, methionine, valine, etc. While the most preferred aliphatic amino acids, for the purposes of the present invention include valine and isoleucine, it is believed that virtually any aliphatic amino acids in the designated position can be recognized within the farnesyl acceptor moiety. In addition, the enzyme has been shown to recognize a peptide containing a hydroxylated amino acid (serine) in place of an aliphatic amino acid (CSIM; seq id no:13). Of course, principal examples of proteins or peptides having a farnesyl acceptor moiety, for the purposes of the present invention, will be the p21$^{ras}$ proteins, including p21$^{H-ras}$, p21$^{K-rasA}$, p21$^{K-rasB}$ and p21$^{N-ras}$. Thus, in light of the present disclosure, a wide variety of peptidyl sequences having a farnesyl acceptor moiety will become apparent.

As outlined above, the inventors have discovered that the farnesyl transferase enzyme is capable of binding to an affinity chromatography medium comprised of the peptide TKCVIM (seq id no:9), coupled to a suitable matrix. This feature of the farnesyl transferase enzyme was discovered by the present inventors in developing techniques for its isolation. Surprisingly, it has been found that the coupling of a peptide such as one which includes CVIM (seq id no:10), as does TKCVIM (seq id no:9), to a suitable chromatography matrix allows for the purification of the protein to a significant degree, presumably through interaction and binding of the enzyme to the peptidyl sequence. A basis for this interaction could be posited as due to the apparent presence of a farnesyl acceptor moiety within this peptide.

The phrase "capable of binding to an affinity chromatography medium comprised of TKCVIM coupled to a suitable matrix," is intended to refer to the ability of the protein to bind to such a medium under conditions as specified herein below. There will, of course, be conditions, such as when the pH is below 6.0, wherein the farnesyl transferase enzyme will not bind effectively to such a matrix. However, through practice of the techniques disclosed herein, one will be enabled to achieve this important objective.

There are numerous chromatography matrixes which are known in the art that can be applied to the practice of this invention. The inventors prefer to use activated CH-Sepharose 4B, to which peptides such as TKCVIM (seq id no:9), or which incorporate the CVIM (seq id no:10) structure, can be readily attached and washed with little difficulty. However, the present invention is by no means limited to the use of CH-Sepharose 4B, and includes within its intended scope the use of any suitable matrix for performing affinity chromatography known in the art. Examples include solid matrices with covalently bound linkers, and the like, as well as matrices that contain covalently associated avidin, which can be used to bind peptides that contain biotin.

Farnesyl transferase enzymes of the present invention have typically been found to exhibit a molecular weight of between about 70,000 and about 100,000 upon gel filtration chromatography. For comparison purposes, this molecular weight was identified for farnesyl protein transferase through the use of a Superose 12 column, using a column size, sample load and parameters as described herein below.

It is quite possible, depending on the conditions employed, that different chromatographic techniques may demonstrate a farnesyl transferase protein that has an apparent molecular weight somewhat different than that identified using the preferred techniques set forth in the examples. It is intended therefore, that the molecular weight determination and range identified for farnesyl transferase in the examples which follow, are designated only with respect to the precise techniques disclosed herein.

It has been determined that the farnesyl:protein transferase can be characterized as including two subunits, each having a molecular weight of about 45 to 50 kDa, as estimated by SDS polyacrylamide gel electrophoresis (SDS/PAGE). These subunits have been designated as α and β, with the α subunit migrating slightly higher than the β subunit, which suggests that the α subunit may be slightly larger. From tryptic peptide sequence analyses and molecular cloning the nature of the α and β subunits as distinct proteins, encoded by separate genes, has been confirmed. Peptide sequences obtained from the rat brain subunits were subsequently found to be consistent with the amino acid sequences predicted by the DNA coding sequences:

TABLE I

Rat Farnesyl: Protein Transferase Peptide Sequences

α subunit:

```
                                              *
1)  * R A E W A D I P V P Q N D G P S P V V Q I I Y S K
      D                                               E

2)  D A I E L N A A N Y T V W H F R

* * *
3)  H F V I S N T T G Y S D H R R
                        R A V

4)  V L V E W L K

5)  L V P H N E S A W N Y L K

* *
6)  L W D N E L Q Y V D Q L L K
```

β subunit:

```
7)  * A Y C A A S V A S L T N I I T P D L F E G V K E
      S                                       T A

8)  * L L Q W V T S R G
      S               Q

9)  * I Q A T T H F L Q K P V P G F E E C E D A V T * D P
      V                                             S

10) I Q E V F S S Y K

11) F E G G F Q G R

12) F N H L V P P R
              P
```

The sequences shown in Table I were obtained from HPLC-purified tryptic peptides isolated from the α- or β- subunit of purified rat farnesyltransferase (Reiss et al ., 1991). Each peptide represents a pure species from a single HPLC peak. Asterisks denote ambiguous residues from amino acid sequencing. The amino acid sequences of all 6 peptides of each subunit (shown above) are found within continuous segments of the amino acid sequence predicted from the respective cDNA clones (seq id no:1; seq id no:3), except for the differences indicated below certain of the peptide sequences.

The inventors have found that the holoenzyme forms a stable complex with all-trans [$^3$H]farnesyl pyrophosphate (FPP) that can be isolated by gel electrophoresis. The [$^3$H]FFP is not covalently bound to the enzyme, and is released unaltered when the enzyme is denatured. When incubated with an acceptor such as p21$_{H-ras}$, the complex transfers [$^3$H]farnesyl from the bound [$^3$H]FFP to the ras protein. Furthermore, crosslinking studies have shown that p21$^{H-ras}$ binds to the β subunit, raising the possibility that the [$^3$H]FFP binds to the α subunit. If this is the case, it would invoke a reaction mechanism in which the α subunit act as a prenyl pyrophosphate carrier that delivers FPP to p21$^{H-ras}$, which is bound to the β subunit. Interestingly, the inventors have recently discovered that the α subunit is shared with another prenyltransferase, geranylgeranyltransferase, that attaches 20-carbon geranylgeranyl to Ras-related proteins.

An additional property discovered for farnesyl transferase enzymes is that they can be inhibited by peptides or proteins, particularly short peptides, which include certain structural features, related in some degree to the farnesyl acceptor moiety discussed above. As used herein, the word "inhibited" refers to any degree of inhibition and is not limited for these purposes to only total inhibition. Thus, any degree of partial inhibition or relative reduction in farnesyl transferase activity is intended to be included within the scope of the term "inhibited." Inhibition in this context includes the phenomenon by which a chemical constitutes an alternate substrate for the enzyme, and is therefore farnesylated in preference to the ras protein, as well as inhibition where the compound does not act as an alternate substrate for the enzyme.

Preparation of Farnesyl:Protein Transferase

The present invention is also concerned with techniques for the identification and isolation of farnesyl transferase enzymes, and particularly mammalian farnesyl transferases (CAAX farnesyltransferases). Techniques are herein disclosed for the isolation of farnesyl transferase which are believed to be applicable to the purification of the native protein, or alternatively, to the purification of the recombinant enzyme following the molecular cloning and co-expression of the constituent subunits.

An important feature of the purification scheme disclosed herein involves the use of short peptide sequences which the inventors have discovered will bind the enzyme, allowing their attachment to chromatography matrices, such matrices may, in turn, be used in connection with affinity chromatography to purify the enzyme to a relative degree. Thus, in certain embodiments, the present invention is concerned with a method of preparing a farnesyl transferase enzyme which includes the steps of:

(a) preparing a cellular extract which includes the enzyme;

(b) subjecting the extract to affinity chromatography on an affinity chromatography medium to bind the enzyme thereto, the medium comprised of a farnesyl transferase binding peptide coupled to a suitable matrix;

(c) washing the medium to remove impurities; and (d) eluting the enzyme from the washed medium.

Thus, the first step of the purification protocol involves simply preparing a cellular extract which includes the enzyme. The inventors have discovered that the enzyme is soluble in buffers such as low-salt buffers, and it is proposed that virtually any buffer of this type can be employed for initial extraction of the protein from the tissue of choice or from recombinant cells in which the constituent subunits of the enzyme are expressed. The inventors prefer a 50 mM Tris-chloride, pH 7.5, buffer which includes a divalent chelator (e.g., 1 mM EDTA, 1 mM EGTA), as well as protease inhibitors such as phenylmethylsulphonyl fluoride (PMSF) and/or leupeptin. Of course, those of skill in the art will recognize that a variety of other types of buffers may be employed as extractants where desired, so long as the enzyme is extractable in such a buffer and its subsequent activity is not adversely affected to a significant degree.

In embodiments concerning the purification of the native enzyme, the choice of tissue from which one will seek to obtain the farnesyl transferase enzyme is not believed to be of crucial importance. In fact, it is believed that farnesyl transferases are components of virtually all living cells. Therefore, the tissue of choice will typically be that which is most readily available to the practitioner. In that farnesyl transferase action appears to proceed similarly in most systems studied, including, cultured hamster cells, rat brain, and even yeast, it is believed that this enzyme will exhibit similar qualities, regardless of its source of isolation.

In preferred embodiments, the inventors have isolated the native enzyme from rat brains in that this source is readily available. However, numerous other sources are contemplated to be directly applicable for isolation of the native enzyme, especially mammalian tissues such as liver, and human placenta, and also reticulocytes, or even yeast. Those of skill in the art, in light of the present disclosure, should appreciate that the techniques disclosed herein will be generally applicable to all such farnesyl transferases.

It will also be appreciated that the enzyme may be purified from recombinant cells prepared in accordance with the present invention. The techniques disclosed for the isolation of native farnesyl transferase are believed to be equally applicable to the purification of the protein from recombinant host cells, whether bacterial or eukaryotic, in which DNA segments encoding the selected constituent subunit has been expressed or co-expressed.

After the cell extract is prepared the enzyme is preferably subjected to two partial purification steps prior to affinity chromatography. These steps comprise preliminary treatment with 30% saturated ammonium sulfate which removes certain contaminants by precipitation. This is followed by treatment with 50% saturated ammonium sulfate, which precipitates the farnesyl transferase. The pelleted enzyme is then dissolved in a suitable buffer, such as 20 mM Tris-chloride (pH 7.5) containing 1 mM DTT and 20 $\mu$M $ZnCl_2$, dialyzed against the same buffer, and then subjected to further purification steps.

In preferred embodiments, the dialyzed solution containing the enzyme is applied to a column containing an ion exchange resin such as Mono Q. After washing of the column to remove contaminants, the enzyme is eluted with a gradient of 0.25–2.0M NaCl in the same buffer. The enzyme activity in each fraction is assayed as described below, and the fractions containing active enzyme are pooled and applied to the affinity column described below.

It is, of course, recognized that the preliminary purification steps described above are preferred laboratory procedures that might readily be replaced with other procedures of equivalent effect such as ion exchange chromatography on other resins or gel filtration chromatography. Indeed, it is possible that these steps could even be omitted and the crude cell extract might be carried directly to affinity chromatography.

After the preliminary purification steps, the extract may be subjected to affinity chromatography on an affinity chromatography medium which includes a farnesyl transferase binding peptide coupled to a suitable matrix. Typically, preferred farnesyl transferase binding peptides will comprise a peptide of at least 4 amino acids in length and will include a carboxy terminal sequence of -C-A-A-X, wherein:

C = cysteine;

A = an aliphatic or hydroxy amino acid; and

X = any amino acid.

Preferred binding peptides of the present invention which fall within the above general formula include structures such as -C-V-I-M (seq id no:10), -C-S-I-M (seq id no:13) and -C-A-I-M (seq id no:14), all of which structures are found to naturally occur in proteins which are believed to be acted upon by farnesyl protein transferases in nature. Particularly preferred are relatively short peptides, such as on the order of about 4 to about 10 amino acids in length which incorporate one of the foregoing binding sequences. Of particular preference is the peptide T-K-C-V-I-M (seq id no:9), which has been effectively employed by the inventors in the isolation of farnesyl protein transferase.

The next step in the overall general purification scheme involves simply washing the medium to remove impurities. That is, after subjecting the extract to affinity chromatography on the affinity matrix, one will desire to wash the matrix in a manner that will remove the impurities while leaving the farnesyl transferase enzyme relatively intact on the medium. A variety of techniques are known in the art for washing matrices such as the one employed herein, and all such washing techniques are intended to be included within the scope of this invention. Of course, for washing purposes, one will not desire to employ buffers that will release or otherwise alter or denature the enzyme. Thus, one will typically want to employ buffers which contain non-denaturing detergents such as octylglucoside buffers, but will want to avoid buffers containing, e.g., chaotropic reagents which serve to denature proteins, as well as buffers of low pH (e.g., less than 7), or of high ionic strength (e.g., greater than 1.0M), as these buffers tend to elute the bound enzyme from the affinity matrix.

After the matrix-bound enzyme has been sufficiently washed, for example in a medium-ionic strength buffer at essentially neutral pH, the specifically bound material can be eluted from the column by using a similar buffer but of reduced pH (for example, a pH of between about 4 and 5.5). At this pH, the enzyme will typically be found to elute from the preferred affinity matrices disclosed in more detail hereinbelow.

While it is believed that advantages in accordance with the invention can be realized simply through affinity chromatography techniques, additional benefits will be achieved through the application of additional purification techniques, such as gel filtration techniques. For example, the inventors have discovered that Sephacryl S-200 high resolution gel columns can be employed with significant benefit in terms of protein purification. However, the present disclosure is by no means limited to the use of Sephacryl S-200, and it is believed that virtually any type of gel filtration arrangement can be employed with some degree of benefit. For example, one may wish to use techniques such as gel filtration, employing media such as Superose, Agarose, or even Sephadex.

Through the application of various of the foregoing approaches, the inventors have successfully achieved farnesyl transferase enzyme compositions of relatively high specific activity, measured in terms of ability to transfer farnesol from all-trans farnesyl pyrophosphate. For the purposes of the present invention, one unit of activity is defined as the amount of enzyme that transfers 1 pmol of farnesol from all-trans farnesyl pyrophosphate (FPP) into acid-precipitable $p21^{H-ras}$ per hour under the conditions set forth in the Examples. Thus, in preferred embodiments the present invention is concerned with compositions of farnesyl transferase which include a specific activity of between about 5 and about 10 units/mg of protein. In more preferred embodiments, the present invention is concerned with compositions which exhibit a farnesyl transferase specific activity of between about 500 and about 600,000 units/mg of protein. Thus, in terms of the unit definition set forth above, the inventors have been able to achieve compositions having a specific activity of up to about 600,000 units/mg using techniques disclosed herein.

Cloning of Farnesyl:Protein Transferase Subunits

Important aspects of the present invention concern isolated DNA segments and recombinant vectors encoding the α and β subunits of mammalian farnesyl:protein transferases (CAAX farnesyltransferases), and the creation of recombinant host cells through the application of DNA technology, which express one, or preferably both, of these polypeptides.

As used herein, the term "DNA segment" in intended to refer to a DNA molecule which has been isolated free of total genomic DNA of a particular species. Therefore, a DNA segment encoding α subunit of farnesyl:protein transferase is intended to refer to a DNA segment which contains such coding sequences yet is isolated away from total genomic DNA of the species from which the DNA is obtained. Included within the term "DNA segment", are DNA segments which may be employed in the preparation of vectors, as well as the vectors themselves, including, for example, plasmids, cosmids, phage, viruses, and the like.

In particular embodiments, the invention concerns isolated DNA segments and recombinant vectors incorporating DNA sequences which encode a farnesyl:protein transferase subunit that includes within its amino acid sequence the amino acid sequence of seq id no:1 or seq id no:3, corresponding to rat brain farnesyl transferase subunits α and β, respectively. Moreover, in other particular embodiments, the invention concerns isolated DNA segments and recombinant vectors incorporating DNA sequences which encode a farnesyl:protein transferase subunit that includes within its amino acid sequence the amino acid sequence of seq id no:5 or seq id no:7, corresponding to human farnesyl transferase subunits α and β, respectively. Recombinant vectors and isolated segments may therefore variously include the α or β subunit coding regions themselves, coding regions bearing selected alterations or modifications in the basic coding region or may encode larger polypeptides which nevertheless include sequences which will confer farnesyl transferase activity when said polypeptide is combined with the alternate subunit.

However, it will be understood that this aspect of the invention is not limited to the particular nucleic acid and amino acid sequences of seq id no:1 and no:2 and seq id no:5 and no:6 (α subunit) or seq id no:3 and no:4 and seq id no:7 and 8 (β subunit). Accordingly, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

The recombinant cloning of cDNAs encoding the farnesyl transferase α and β subunits was achieved through the use of the peptide sequence information set forth above which was used in the preparation of subunit-specific oligonucleotides. Such oligonucleotides could be employed in the direct hybridization screening of a clone bank. However, the inventors preferred to use the peptide sequences in the preparation of primers for use in PCR amplification and partial sequencing of the selected subunit gene to confirm the underlying DNA sequence, and to prepare longer and more specific probes for use in clone bank screening.

In screening for the farnesyl transferase subunit-specific sequences, the inventors chose to use a cDNA clone bank prepared from poly $A^+$ RNA. However, it is believed that the type of clone bank used is not crucial and that, if desired, one could employ a genomic clone bank. Similarly, in that the farnesyl transferase enzyme appears to be fairly ubiquitous in nature, it is believed that virtually any eukaryotic cell source may be employed for the preparation of RNA from which the clone bank is to be generated. One may mention by way of example, yeast, mammalian, plant, eukaryotic parasites and even viral-infected types of cells as the source of starting poly $A^+$ RNA.

As the protein was initially purified from a mammalian source (rat), it is contemplated that particular advantages may be found in the use of mammalian cells, such as rat or human cell lines, as an RNA source. One may, of course, wish to first test such a cell line to ensure that relatively high levels of the farnesyl transferase enzyme are being produced by the selected cells. Rat brain, PC12 (a rat adrenal tumor cell line) and KNRK (a newborn rat kidney cell line) were preferred by the present inventors as they exhibited high levels of endogenous farnesyl:protein transferase activity.

The type of cDNA clone bank used in the screening procedure is not believed to be particularly critical. However, one will likely find particular benefit through the preparation and use of a phage-based bank, such as λgt10 or λgt11, preferably using a particle packaging system. Phage-based cDNA banks are preferred because of the large numbers of recombinants that may be prepared and screened will relative ease. The manner in which the cDNA itself is prepared is again not believed to be particularly crucial. However, the inventors successfully employed both oligo dT and randomly primed cDNA, from a consideration of the difficulties which may arise in the reverse transcription of a large mRNA molecule.

Once a clone bank has been prepared, it may be screened in a number of fashions. For example, as mentioned above, one could employ the subunit peptide sequences set forth above for the preparation of nucleotide probes with which to directly screen the clone bank. A more preferable approach was found to be to use such sequences in the preparation of primers which may were used in PCR-based reactions to amplify and then sequence portions of the selected subunit gene, to thereby confirm the actual underlying DNA sequence, and to prepare longer and more specific probes for further screening. These primers may also be employed for the preparation of cDNA clone banks which are enriched for 3' and/or 5' sequences. This may be important, e.g., where less than a full length clone is obtained through the initially prepared bank.

If a less than full length clone was obtained on initial screening, the entire sequence could be subsequently obtained through the application of 5' and/or 3' extension technology, as required. The techniques for obtaining an extended farnesyl transferase subunit clone will be known to those of skill in the art in light of the present disclosure. The procedures used are those described in Frohman et al. (1988), involving a combination of reverse transcription, tailing with terminal deoxytransferase and, finally, PCR.

It is proposed that the DNA segments of the present invention may be employed for a variety of applications. For example, a particularly useful application concerns the recombinant production of the individual subunits or proteins or peptides whose structure is derived from that of the subunits, or in the recombinant production of the holoenzyme following co-expression of the two subunits. Additionally, the farnesyl transferase-encoding DNA segments of the present invention can also be used in the preparation of nucleic acid probes or primers, which can, for example, be used in the identification and cloning of farnesyl transferase genes or related genomic sequences, or in the study of subunit(s) expression, and the like.

Expression of Farnesyl:Protein Transferase Subunits

Turning firstly to the expression of the cloned subunits. Once a suitable (full length if desired) clone or clones have been obtained, whether they be cDNA based or genomic, one may proceed to prepare an expression system for the recombinant preparation of one, or preferably both, of the subunits. The engineering of DNA segment(s) for expression in a prokaryotic or eukaryotic system may be performed by techniques generally known to those of skill in recombinant expression. It is believed that virtually any expression system may be employed in the expression of either or both subunits. Both subunits of the enzyme have been successfully co-expressed in eukaryotic expression systems with the production of active enzyme, but it is envisioned that bacterial expression systems may ultimately be preferred for the preparation of farnesyl transferase for all purposes. The cDNAs for both subunits have been separately expressed in bacterial systems, with the encoded proteins being expressed as fusions with *Schistosoma japonicum* glutathione S-transferase. It is believed that bacterial expression will ultimately have numerous advantages over eukaryotic expression in terms of ease of use and quantity of materials obtained thereby. Furthermore, it is proposed that co-transformation of host cells with DNA segments encoding both the α and β subunits will provide a convenient means for obtaining active enzyme. However, separate expression followed by reconstitution is also certainly within the scope of the invention. Both cDNA and genomic sequences are suitable for eukaryotic expression, as the host cell will, of course, process the genomic transcripts to yield functional mRNA for translation into protein.

It is similarly believed that almost any eukaryotic expression system may be utilized for the expression of either, or preferably, both of the farnesyl transferase subunits, e.g., baculovirus-based, glutamine synthase-based or dihydrofolate reductase-based systems could be employed. However, in preferred embodiments, it is contemplated that plasmid vectors incorporating an origin of replication and an efficient eukaryotic promoter, as exemplified by the eukaryotic vectors of the pCMV series, such as pCMV5, will be of most use. For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes the enzyme, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

As noted above, it is proposed that in embodiments concerning the production of farnesyl transferase enzyme, the α and β subunits may be co-expressed in the same cell. This may be achieved by co-transfecting the cell with two distinct recombinant vectors, each bearing a copy of either the α- or β-encoding DNA. Alternatively, a single recombinant vector may be constructed to include the coding regions for both of the subunits, which could then be expressed in cells transfected with the single vector. In either event, the term "co-expression" herein refers to the expression of both the α and β subunits of farnesyl transferase in the same recombinant cell.

It is contemplated that virtually any of the commonly employed host cells can be used in connection with the expression of one, or preferably both, of the farnesyl transferase subunits in accordance herewith. Examples include cell lines typically employed for eukaryotic expression such as 239, AtT-20, HepG2, VERO, HeLa, CHO, WI 38, BHK, COS-7, RIN and MDCK cell lines. A preferred line for use in eukaryotic expression embodiments of the present invention has been found to be the human embryonic kidney cell line, 293.

In accordance with the general guidelines described above, a preferred method for expressing farnesyl transferase DNA has been found to be the transfection of human embryonic kidney 293 cells with expression vectors termed pFT-α or pFT-β. The pFT expression vectors are constructed from pCMV5, a plasmid that contains the promoter-enhancer region of the major immediate early gene of human cytomegalovirus (Andersson et al., 1989).

Nucleic Acid Hybridization

The DNA sequences disclosed herein will also find utility as probes or primers in nucleic acid hybridization embodiments. As such, it is contemplated that oligonucleotide fragments corresponding to the sequences of seq id no:2, seq id no:4, seq id no:6 and seq id no:8 for stretches of between about 10 nucleotides to about 30 nucleotides will find particular utility, with even longer sequences, e.g., 40, 50, 60, even up to full length, being even more particularly preferred. The ability of such nucleic acid probes to specifically hybridize to farnesyl transferase subunit-encoding sequences will enable them to be of use in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of farnesyl transferase genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and\or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating farnesyl transferase genes.

Of course, for some applications, for example, where one desires to prepare mutants employing a mutant primer strand hybridized to an underlying template or where one seeks to isolate farnesyl transferase-encoding sequences for related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one will likely desire to employ an enzyme tag such a urease, alkaline phosphatase or peroxidase, instead of radioactive or other environmental undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Biological Functional Equivalent Amino Acids

As mentioned above, modification and changes may be made in the structure of the farnesyl transferase (CAAX farnesyltransferase) subunits and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even counterveiling properties (e.g., antagonistic v. agonistic). It is thus contemplated by the inventors that various changes may be made in the sequence of the peptides (or underlying DNA) without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982). It is known that certain amino acids may be substituted for other amino acids having a similar hydropathic index or score and still result in a protein with similar biological activity. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (-0.4); threonine (-0.7); serine (—0.8); tryptophan (-0.9); tyrosine (-1.3); proline (-1.6); histidine (—3.2); glutamate (-3.5); glutamine (-3.5); aspartate (-3.5); asparagine (-3.5); lysine (-3.9); and arginine (-4.5).

As the relative hydropathic character of the amino acids determines the secondary structure of the resultant protein, which in turn defines the interaction of the protein with other molecules, for example, enzymes, substrates, inhibitors, receptors, antibodies, antigens, and the like. It is known in the art that an amino acid may be substituted by another amino acid having a similar hydropathic index and still obtain a biological functionally equivalent protein. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the side-chain substituents, for example, size, electrophilic character, charge, and the like. Exemplary substitutions which take various of the foregoing characteristics into consideration are well known to those of skill in the art and include: alanine, glycine and serine; arginine and lysine; glutamate and aspartate; serine and threonine; and valine, leucine and isoleucine.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Inhibitors of Farnesyl:Protein Transferase

Of principal importance to the present invention is the discovery that proteins or peptides which incorporate a farnesyl acceptor sequence, such as one of the farnesyl acceptor sequences discussed above, function as inhibitors of farnesyl:protein transferase, and therefore may serve as a basis for anticancer therapy. In particular, it has been found that farnesyl acceptor peptides can successfully function both as false substrates that serve to inhibit the farnesylation of natural substrates such as $p21^{ras}$, and as direct inhibitors which are not themselves farnesylated. Compounds falling into the latter category are particularly important in that these compounds are "pure" inhibitors that are not consumed by the inhibition reaction and can continue to function as inhibitors. Both types of compounds constitute an extremely important aspect of the invention in that they provide a means for blocking farnesylation of $p21^{ras}$ proteins, for example, in an affected cell system.

The farnesyl transferase inhibitor embodiments of the present invention concern in a broad sense a peptide or protein other than $p21^{ras}$ proteins, lamin a or lamin b, or yeast mating factor a, which peptide or protein includes a farnesyl acceptor sequence within its structure and is further capable of inhibiting the farnesylation of $p21^{ras}$ by farnesyl transferase.

In preferred embodiments, the farnesyl transferase inhibitor of the present invention will include a farnesyl acceptor or inhibitory amino acid sequence having the amino acids -C-A-A-X (seq id no:12), wherein:

C =cysteine;

A =any aliphatic, aromatic or hydroxy amino acid; and

X =any amino acid.

Typically, the farnesyl acceptor or inhibitory amino acid sequence will be positioned at the carboxy terminus of the protein or peptide such that the cysteine residue is in the fourth position from the carboxy terminus.

In preferred embodiments, the inhibitor will be a relatively short peptide such as a peptide from about 4 to about 10 amino acids in length. To date, the most preferred inhibitor tested is a tetrapeptide which incorporates the above-mentioned C-A-A-X (seq id no:12) recognition structure. It is possible that even shorter peptides will ultimately be preferred for practice of the invention in that the shorter the peptide, the greater the uptake by such peptide by biological systems, and the reduced likelihood that such a peptide will be destroyed or otherwise rendered biologically ineffective prior to effecting inhibition. However, numerous suitable inhibitory peptides have been prepared and tested by the present inventors, and shown to inhibit enzymatic activities virtually completely, at reasonable concentrations, e.g., between about 1 and 3 $\mu$M (with 50% inhibitions on the order of 0.1 to 0.5 $\mu$M).

While, broadly speaking, it is believed that compounds exhibiting an $IC_{50}$ of between about 0.01 $\mu$M and 10 $\mu$M will have some utility as farnesyl transferase inhibitors, the more preferred compounds will exhibit an $IC_{50}$ of between 0.01 $\mu$M and 1 $\mu$M. The most preferred compounds will generally have an $IC_{50}$ of between about 0.01 $\mu$M and 0.3 $\mu$M.

Exemplary peptides which have been prepared, tested and shown to inhibit farnesyl transferase at an $IC_{50}$ of between 0.01 and 10 $\mu$M include CVIM (seq id no:10); KKSKTKCVIM (seq id no:11); TKCVIM (seq id no:9); RASNRSCAIM (seq id no:15); TQSPQNCSIM (seq id no:16); and the following tetrapeptides:

CIIM (seq id no:17); CVVM (seq id no:18); CVLS (seq id no:19); CVLM (seq id no:20); CAIM (seq id no:14); CSIM (seq id no:13); CCVQ (seq id no:21); CIIC (seq id no:22); CIIS (seq id no:23); CVIS (seq id no:24); CVIA (seq id no:25); CVIL (seq id no:26); CLIL (seq id no:27); CLLL (seq id no:28); CTVA (seq id no:29); CVAM (seq id no:30); CKIM (seq id no:31); CLIM (seq id no:32); CFIM (seq id no:33); CVFM (seq id no:34); CVIF (seq id no:35); CEIM (seq id no:36); CGIM (seq id no:37); CPIM (seq id no:38); CVYM (seq id no:39); CVTM (seq id no:40); CVPM (seq id no:41); CVSM (seq id no:42); CVIV (seq id no:43); CVIP (seq id no:44); CVII (seq id no:45); CVWM (seq id no:46); CIFM (seq id no:47).

A variety of peptides have been synthesized and tested such that now the inventors can point out peptide sequences having particularly high inhibitory activity, i.e., wherein relatively lower concentrations of the peptides will exhibit an equivalent inhibitory activity ($IC_{50}$). Interestingly, it has been found that slight changes in the sequence of the acceptor site can result in loss of inhibitory activity. Thus, when TKCVIM is changed to TKVCIM, the inhibitory activity of the peptide is reversed. Similarly, when a glycine is substituted for one of the aliphatic amino acids in CAAX, a decrease in inhibitory activity is observed. However, it is proposed that as long as the general formula as discussed above is observed, one will achieve a structure that is inhibitory to farnesyl transferase.

A particularly important discovery is the finding that the incorporation of an aromatic residue such as phenylalanine, tyrosine or tryptophan into the third position of the CAAX (seq id no:12) sequence will result in a "pure" inhibitor. As used herein, a "pure" farnesyl:protein transferase inhibitor is intended to refer to one which does not in itself act as a substrate for farnesylation by the enzyme. This is particularly important in that the inhibitor is not consumed by the inhibition process, leaving the inhibitor to continue its inhibitory function unabated. Exemplary compounds which have been tested and found to act as pure inhibitors include CVFM (seq id no:34), CVWM (seq id no:46), CVYM (seq id no:39), CIFM (seq id no:47), CV(pCl-F)M, L-penicillamine-VFM, and L-penicillamine-VIM. Pure inhibitors will therefore incorporate an inhibitory amino acid sequence rather than an acceptor sequence, with the inhibitory sequence characterized generally as having an aromatic moiety associated with the penultimate carboxy terminal amino acid, whether it be an aromatic amino acid or another amino acid which has been modified to incorporate an aromatic structure (Goldstein et al., 1991).

Importantly, the pure inhibitor CVFM (seq id no:34) is the best inhibitor identified to date by the inventors. It should be noted that the related peptide, CFIM (seq id no:33) is not a "pure" inhibitor; its inhibitory activity is due to its action as a substrate for farnesylation.

The potency of CVFM peptides as inhibitors of the enzyme may be enhanced by attaching substituents such as fluoro, chloro or nitro derivatives to the phenyl ring. An example is parachlorophenylalanine, which has been tested and found to have "pure" inhibitory activity. It may also be possible to substitute more complex hydrophobic substances for the phenyl group of phenylalanine. These would include naphthyl ring systems.

The present inventors propose that additional improvements can be made in pharmaceutical embodiments of the inhibitor by including within their structure moieties which will improve their hydrophobicity, which it is proposed will improve the uptake of peptidyl structures by cells. Thus, in certain embodiments, it is proposed to add fatty acid or polyisoprenoid side chains to the inhibitor which, it is believed, will improve their lipophilic nature and enhance their cellular uptake.

Other possible structural modifications include the addition of benzyl, phenyl or acyl groups to the amino acid structures, preferably at a position sufficiently removed from the farnesyl acceptor site, such as at the amino terminus of the peptides. It is proposed that such structures will serve to improve lipophilicity. In this regard, the inventors have found that N-acetylated and N-octylated peptides such as modified CVIM retain much of their inhibitory activity, whereas S-acetoamidated CVIM appears to lose much of its inhibitory activity.

The invention also contemplates that modifications can be made in the structure of inhibitory proteins or peptides to increase their stability within the body, such as modifications that will reduce or eliminate their susceptibility to degradation, e.g., by proteases. For example, the inventors contemplate that useful structural modifications will include the use of amino acids which are less likely to be recognized and cleaved by proteases, such as the incorporation of D-amino acids, or amino acids not normally found in proteins such as ornithine or taurine. Other possible modifications include the cyclization of the peptide, derivatization of the NH groups of the peptide bonds with acyl groups, etc.

Assays For Farnesyl:Protein Transferase

In still further embodiments, the invention concerns a method for assaying farnesyl transferase (CAAX farnesyltransferase) activity in a composition. This is an important aspect of the invention in that such an assay system provides one with not only the ability to follow the isolation and purification of native or recombinant farnesyl transferase enzymes, but it also forms the basis for developing a screening assay for candidate inhibitors of the enzyme, discussed in more detail below. The assay method generally includes determining the ability of a composition suspected of having farnesyl transferase activity to catalyze the transfer of farnesol to an acceptor protein or peptide. As noted above, a farnesyl acceptor protein or peptide is generally defined as a protein or peptide which will act as a substrate for farnesyl transferase and which includes a recognition site such as -C-A-A-X, as defined above.

Typically, the assay protocol is carried out using all-trans farnesyl pyrophosphate as the farnesol donor in the reaction. Thus, one will find particular benefit in constructing an assay wherein a label is present on the farnesyl moiety of all-trans farnesyl pyrophosphate, in that one can measure the appearance of such a label, for example, a radioactive label, in the farnesyl acceptor protein or peptide.

As with the characterization of the enzyme discussed above, the farnesyl acceptor sequence which are employed in connection with the assay can be generally defined by -C-A-A-X (seq id no:12), with preferred embodiments including sequences such as C-V-I-M (seq id no:10), -C-S-I-M (seq id no:13), -C-A-I-M (seq id no:14), etc., all of which have been found to serve as useful enzyme substrates. It is believed that most proteins or peptides that include a carboxy terminal sequence of -C-A-A-X (seq id no:12) can be successfully employed in farnesyl protein transferase assays. For use in the assay a preferred farnesyl acceptor protein or peptide will be a $p21^{ras}$ protein. This is particularly true where one seeks to identify inhibitor substances, as discussed in more detail below, which function either as "false acceptors" in that they divert farnesylation away from natural substrates by acting as substrates in and or themselves, or as "pure" inhibitors which are not in themselves farnesylated. The advantage of employing a natural substrate such as $p21^{ras}$ is several fold, but includes the ability to separate the natural substrate from the false substrate to analyze the relative degrees of farnesylation.

However, for the purposes of simply assaying enzyme specific activity, e.g., assays which do not necessarily involve differential labeling or inhibition studies, one can readily employ short peptides as a farnesyl acceptor in such protocols, such as peptides from about 4 to about 10 amino acids in length which incorporate the recognition signal at their carboxy terminus. Exemplary farnesyl acceptor protein or peptides include but are not limited to CVIM (seq id no:10); KKSKTKCVIM (seq id no:11); TKCVIM (seq id no:9); RASNRSCAIM (seq id no:15); TQSPQNCSIM (seq id no:16); CIIM (seq id no:17); CVVM (seq id no:18); and CVLS (seq id no:19).

Assays for Candidate Substances

In still further embodiments, the present invention concerns a method for identifying new farnesyl transferase inhibitory compounds, which may be termed as "candidate substances." It is contemplated that this screening technique will prove useful in the general identification of any compound that will serve the purpose of inhibiting farnesyl transferase. It is further contemplated that useful compounds in this regard will in no way be limited to proteinaceous or peptidyl compounds. In fact, it may prove to be the case that the most useful pharmacologic compounds for identification through application of the screening assay will be non-peptidyl in nature and, e.g., which will be recognized and bound by the enzyme, and serve to inactivate the enzyme through a tight binding or other chemical interaction.

Thus, in these embodiments, the present invention is directed to a method for determining the ability of a candidate substance to inhibit a farnesyl transferase enzyme, the method including generally the steps of:

(a) obtaining an enzyme composition comprising a farnesyl transferase enzyme that is capable of transferring a farnesyl moiety to a farnesyl acceptor substance;

(b) admixing a candidate substance with the enzyme composition; and (c) determining the ability of the farnesyl transferase enzyme to transfer a farnesyl moiety to a farnesyl acceptor substrate in the presence of the candidate substance.

An important aspect of the candidate substance screening assay hereof is the ability to prepare a native or recombinant farnesyl transferase enzyme composition in a relative purified form, for example, in a manner as discussed above. This is an important aspect of the candidate substance screening assay in that without at least a relatively purified preparation, one will not be able to assay specifically for enzyme inhibition, as opposed to the effects of the inhibition upon other substances in the extract which then might affect the enzyme. In any event, the successful isolation of the farnesyl transferase enzyme now allows for the first time the ability to identify new compounds which can be used for inhibiting this cancer-related enzyme.

The candidate screening assay is quite simple to set up and perform, and is related in many ways to the assay discussed above for determining enzyme activity. Thus, after obtaining a relatively purified preparation of the enzyme, either from native or recombinant sources, one will desire to simply admix a candidate substance with the enzyme preparation, preferably under conditions which would allow the enzyme to perform its farnesyl transferase function but for inclusion of a inhibitory substance. Thus, for example, one will typically desire to include within the admixture an amount of a known farnesyl acceptor substrate such as a $p21^{ras}$ protein. In this fashion, one can measure the ability of the candidate substance to reduce farnesylation of the farnesyl acceptor substrate relatively in the presence of the candidate substance.

Accordingly, one will desire to measure or otherwise determine the activity of the relatively purified enzyme in the absence of the added candidate substance relative to the activity in the presence of the candidate substance in order to assess the relative inhibitory capability of the candidate substance.

Methods of Inhibiting Farnesyl:protein Transferase

In still further embodiments, the present invention is concerned with a method of inhibiting a farnesyl transferase enzyme which includes subjecting the enzyme to an effective concentration of a farnesyl transferase inhibitor such as one of the family of peptidyl compounds discussed above, or with a candidate substance identified in accordance with the candidate screening assay embodiments. This is, of course, an important aspect of the invention in that it is believed that by inhibiting the farnesyl transferase enzyme, one will be enabled to treat various aspects of cancers, such as ras-related cancers. It is believed that the use of such inhibitors to block the attachment of farnesyl groups to ras proteins in malignant cells of patients suffering with cancer or precancerous states will serve to treat or palliate the cancer, and may be useful by themselves or in conjunction with other cancer therapies, including chemotherapy, resection, radiation therapy, and the like.

BRIEF DESCRIPTION OF THE DRAWINGS

FIG. 16A and FIG. 16B cDNA Probes Generated from a Knowledge of the Amino Acid Sequences of Peptides Derived from Rat Farnesyl Transferase α and β Subunits. Panel A: Primer a1 (seq id no:57) and Primer α2 (seq id no:58) were used in PCR with rat genomic DNA to obtain the nucleotide sequence encoding the amino acid sequence of the peptide shown (seq id no:59), as described in Example III. The nucleotide sequence 5'-ATIGAGTTAAACGCA-GCCAACTATACGGTCTGGCACTT-3' (a specific example in accordance with residues 6–54 of seq id no:64), was used as a probe to screen a rat brain cDNA library. Panel B(upper): Primer β1 (seq id no:60) and primer β2 (seq id no:61) were used in PCR with rat genomic DNA to generate the nucleotide sequence encoding the amino acid sequence of the peptide shown (seq id no:63), as described in Example III. Panel B(lower): Nucleotide sequence encoding the peptide as derived from the above PCR (seq id no:62). Primer β3 and primer β4, the sequences of which are contained entirely within seq id no:62, were synthesized and used as the primers for 3'-end amplification of the cDNA, as described in Example III.

FIG. 17 Identification of the Amino Acids Within the Sequence of Rat Farnesyl Transferase α Subunit (FT-α) (seq id no:1) which are Identical with those within the Sequence of Yeast RAM2. Amino acid residues are numbered on the left. Identical amino acids are boxed. The sequence of yeast RAM2 has been reported by He et al. (1991), and the non-identical residues are not shown.

FIG. 18 Identification of the Amino Acid Within the Sequence of Rat Farnesyl Transferase β-Subunit (FT-β) (seq id no:3) which are Identical with those within the Sequence of Yeast DPR1/RAM1. Amino acid residues are numbered on the left. Identical amino acids are boxed. The sequence of yeast DPR1/RAM1 has been reported by Goodman et al. (1988), and the non-identical residues are not shown.

FIG. 19A, FIG. 19B, FIG. 19C and FIG. 19D Distribution of Rat Farnesyl Transferase α and β subunit mRNA in Tissues (A & C) and Cultured Cells (B & D). Panels A & C: Total RNA was isolated from the indicated rat tissues, and an aliquot (30 μg) was subjected to electrophoresis on a 1.5% agarose gel and blotted onto a nylon membrane for blot analysis. Hybridization was carried out at 42° C. for 20 hours with a mixture of two single-stranded uniformly ³²P-labeled cDNA probes, specific for either the α subunit (A) or β subunit (B) of rat farnesyl transferase. Each probe was ~500 nucleotides in length and was used at 2×10⁶ cpm/ml. The filters were washed in 0.2× SSC containing 0.2% (w/v) SDS at 68° C. for 1 hour, then exposed to Kodak XAR-5 film for 2–4 days at −70° C. The positions of RNA standards run in adjacent lanes are indicated on the left. As a loading control, the same filter was reprobed initially with a ³²P-labeled 49-mer oligonucleotide corresponding to rat cyclophilin cDNA (2×10⁶ cpm/ml) and subsequently with a uniformly ³²P-labeled cDNA (~1.2 kb) for rat glyceraldehyde-3-phosphate dehydrogenase (GAPDH) (4×10⁶cpm/ml). After each washing, the reprobed filter was exposed for 12 hours at −70° C. Panels B & D: Expression of the α (C) and β (D) farnesyl transferase subunit mRNA in rat brain, KNRK cells, and PC12 pheochromocytoma cells. An aliquot of poly(A)+RNA from each sample (10 μg) was subjected to blot analysis as described in A & B, and exposed for 12 h at −70° C. The same filter was subsequently reprobed with a ³²P-oligonucleotide derived from the rat cyclophilin cDNA sequence as described in A & B, and the filter was exposed to XAR-5 film for 12 h at −70° C.

FIG. 23A, FIG. 23B, FIG. 23C and FIG. 23D Nucleotide Sequence (seq id no:6) and Deduced Amino Acid Sequence (nucleic acids 1 through 1638 of seq id no:5) of a Full Length cDNA Encoding the Human Farnesyl Transferase α Subunit, and Comparison with the Amino Acid Sequence of the Rat α Subunit. Amino acids are numbered on the left. Amino acid residue 1 is the putative initiator methionine. The translated 379 amino acid sequence of the human farnesyl transferase α subunit protein (seq id no:5) is shown beneath the nucleotide sequence (seq id no:6). Amino acid residues that differ from the rat protein are boxed and the corresponding amino acids in the rat sequence are shown below the human sequence.

FIG. 24A, FIG. 24B and 24C Nucleotide (seq id no:8) and Deduced Amino Acid Sequence (seq id no:7) of a Partial cDNA Encoding the Human Farnesyl Transferase β Subunit, and Comparison with the Amino Acid Sequence of the Rat β Subunit. Nucleotides are numbered on the right. Amino acids are numbered on the left with the number in parentheses indicating the corresponding residue in the rat protein. The translated 387 amino acid sequence (seq id no:7) of the partial human farnesyltransferase β subunit cDNA is shown beneath the nucleotide sequence. Amino acids that differ from the rat protein are boxed and the differences are shown below the human sequence.

DETAILED DESCRIPTION OF THE PREFERRED EMBODIMENTS

Figure 1A:
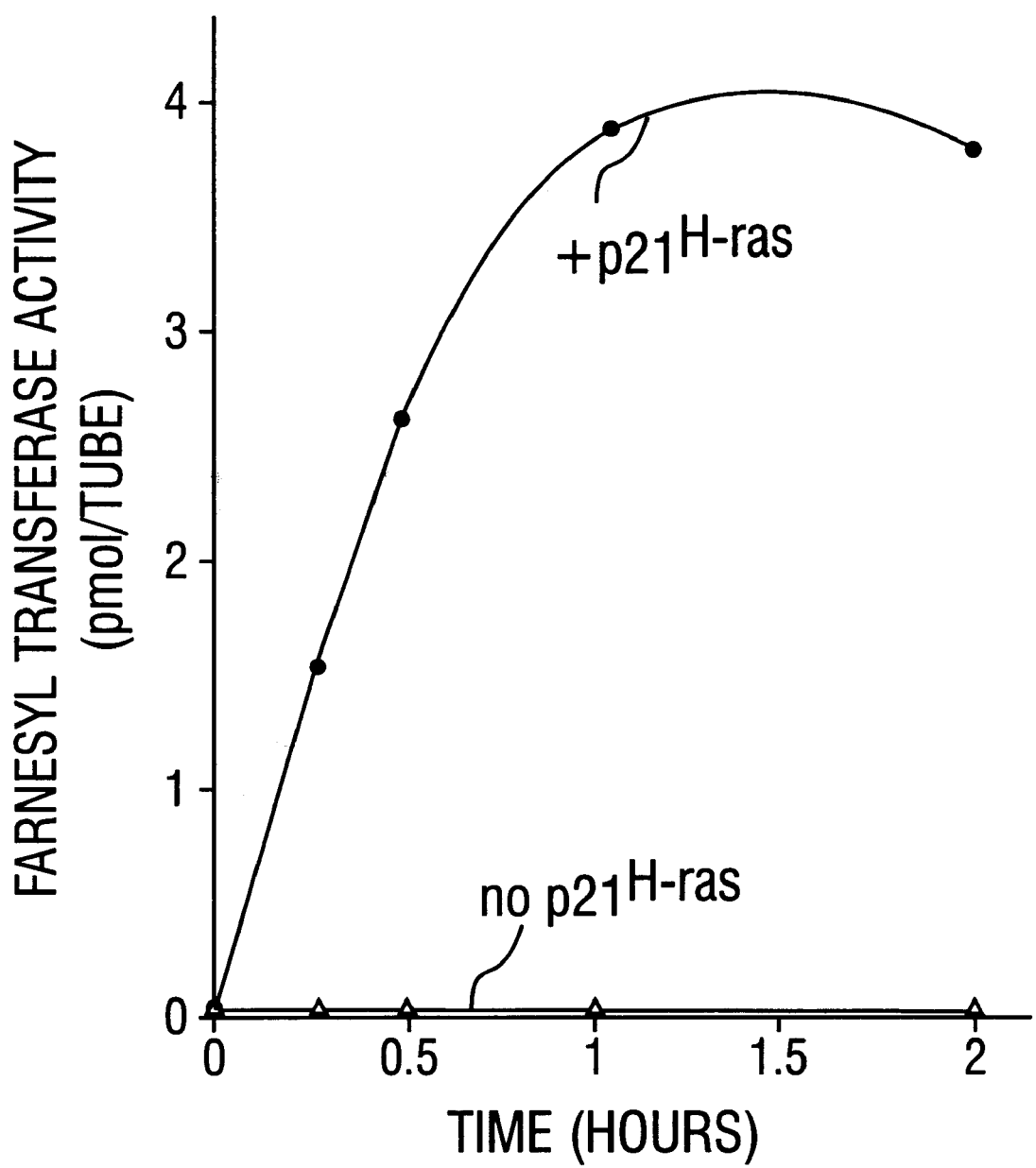
FIG. 1A and FIG. 1B Transfer of Farnesol from [$^3$H]FPP to $p21^{H-ras}$ by Partially Purified Rat Brain Farnesyl:Protein Transferase. Each standard assay mixture contained 10 pmoles of [$^3$H]FPP and 3.5 $\mu$g of partially purified farnesyl transferase in the absence (▲) or presence (●) of 40 $\mu$M $p21^{H-ras}$. Duplicate samples were incubated for the indicated time at 37° C., and TCA-precipitable radioactivity was measured as described in the Examples. The inset shows the migration on a 12% SDS polyacrylamide gel of an aliquot from a reaction carried out for 1 h in the absence or presence of $p21^{H-ras}$. The gel was treated with Entensify solution (DuPont), dried, and exposed to XAR film for 2 days at −70° C.

The following examples illustrate techniques discovered by the inventors for the identification and purification of mammalian farnesyl protein transferase enzymes, as well as techniques for their assay and for the screening of new compounds which may be employed to inhibit such enzymes. These studies also demonstrate a variety of peptidyl compounds which themselves can be employed to inhibit these enzymes. It should be appreciated by those of skill in the art that the techniques disclosed in the examples which follow represent laboratory techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Preparation and Characterization of Farnesyl:protein Transferase

1. Materials

Peptides were obtained from Peninsula Laboratories or otherwise synthesized by standard techniques. All peptides were purified on HPLC, and their identity was confirmed by amino acid analysis. Just prior to use, each peptide was dissolved at a concentration of 0.8 mM in 10 mM dithiothreitol (DTT), and all dilutions were made in 10 mM DTT. Unlabeled all-trans farnesyl pyrophosphate (FPP) was synthesized by the method of Davisson, et al. (1986). [1-$^3$H] Farnesyl pyrophosphate (20 Ci/mmol) was custom synthesized by New England Nuclear. Geraniol and farnesol (both all-trans) were obtained from Aldrich Chemical. All-trans geranylgeraniol was obtained from R. Coates (University of Illinois).

Recombinant wild type human p21$^{H\text{-}ras}$ protein was produced in a bacterial expression system with pAT-rasH (provided by Channing J. Der, La Jolla Cancer Research Foundation, La Jolla, Calif.), an expression vector based on PXVR (Feig et al., 1986). The plasmid was transformed into E. coli JM105, and the recombinant p21$^{H\text{-}ras}$ protein was purified at 4° C. from a high speed supernatant of the bacterial extracts by sequential chromatography on DEAE-Sephacel and Sephadex G-75. Purity was ~90% as judged by Coomassie blue staining of SDS gels. Purified p21$^{H\text{-}ras}$ was concentrated to 15 mg/ml in 10 mM Tris-chloride (pH 7.5) containing 1 mM DTT, 1 mM EDTA, 3 mM MgCl$_2$, and 30 $\mu$M GDP and stored in multiple aliquots at −70° C.

2. Assay for Farnesyl:Protein Transferase Activity

Farnesyl:protein transferase activity was determined by measuring the amount of $^3$H-farnesol transferred from all-trans $^3$H]farnesyl pyrophosphate ([$^3$H]FPP) to p21$^{H\text{-}ras}$ protein. The standard reaction mixture contained the following concentrations of components in a final volume of 25 $\mu$l: 50 mM Tris-chloride (pH 7.5), 50 $\mu$M ZnCl$_2$, 20 mM KCl, 1 mM DTT, and 40 $\mu$M p21$^{H\text{-}ras}$. The mixture also contained 10 pmoles of [$^3$H]FPP (~30,000 dpm/pmol) and 1.8–3.5 $\mu$g of partially purified farnesyl:protein transferase (see below). After incubation for 1 hour at 37° C. in 12×75-mm borosilicate tubes, the reaction was stopped by addition of 0.5 ml of 4% SDS and then 0.5 ml of 30% trichloroacetic acid (TCA).

The tubes were vortexed and left on ice for 45–60 min, after which 2 ml of a 6% TCA/2% SDS solution were added. The mixture was filtered on a 2.5-cm glass fiber filter with a Hoefer filtration unit (FH 225). The tubes were rinsed twice with 2 ml of the same solution, and each filter was washed five times with 2 ml of 6% TCA, dried, and counted in a scintillation counter. One unit of activity is defined as the amount of enzyme that transfers lpmol of [$^3$H]farnesol from [$^3$H]FPP into acid-precipitable p21$^{H\text{-}ras}$ per hour under the standard conditions.

3. Purification of Farnesyl:Protein Transferase

All steps were carried out at 4° C. except where indicated:
Step 1—Ammonium Sulfate Fractionation Brains from 50 male Sprague-Dawley rats (100–150 g) were homogenized in 100 ml of ice-cold buffer containing 50 mM Tris-chloride (pH 7.5), 1 mM EDTA, 1 mM EGTA, 0.2 mM phenylmethylsulfonyl fluoride (PMSF), and 0.1 mM leupeptin, and the extract was spun at 60,000× g for 70 min. The supernatant was brought to 30% saturation with solid ammonium sulfate, stirred for 30 min on ice, and centrifuged at 12,000× g for 10 min to remove precipitated proteins. The resulting supernatant was adjusted to 50% saturation with ammonium sulfate, and the resulting pellet was dissolved in ~20 ml of 20 mM Tris-chloride (pH 7.5) containing 1 mM DTT and 20 $\mu$M ZnCl$_2$ and dialyzed for 4 hours against 4 liters of the same buffer and then 4 liters of fresh buffer of the same composition for 12 hours. The dialyzed material was divided into multiple aliquots and stored at −70° C.

Step 2—Ion-exchange Chromatography

A portion of the 30–50% ammonium sulfate fraction (200 mg protein) was chromatographed on a Mono Q 10/10 column using an FPLC system (Pharmacia LKB Biotechnology). The column was run as described in the legend to FIG. 5. Fractions eluting between 0.3 and 0.4M NaCl contained the majority of the transferase activity. These fractions were pooled, divided into multiple aliquots, and stored at −70° C.

Step 3—Affinity Chromatography

An affinity column containing a peptide corresponding to the COOH-terminal six amino acids of p21$^{K\text{-}ras\text{-}B}$ protein was prepared as follows. Fifteen mg of the peptide TKCVIM (seq id no:9) were coupled to 1 g of activated CH-Sepharose 4B (Pharmacia LKB Biotechnology) according to the manufacturer's instructions. The resulting 2.5-ml slurry was poured into a column, and excess uncoupled peptide was removed by 10 cycles of alternating washes, each consisting of 40 column volumes of 0.1M sodium acetate (pH 4.0) and then 0.1M Tris-chloride (pH 8.0). Both buffers contained 1M NaCl and 10 mM DTT. The column was stored at 4° C. in 20 mM Tris-chloride (pH 7.2) and 0.02% sodium azide. Fifteen mg of Mono Q-purified material in 10ml were applied to a 1-ml peptide column equilibrated in 50 mM Tris-chloride (pH 7.5) containing 0.1M NaCl and 1 mM DTT (Buffer A). The enzyme-containing solution was cycled through the column three times at room temperature. The column was washed with 20 ml of Buffer A containing 0.2% (w/v) octyl-β-D-glucopyranoside (Buffer B). The enzyme was eluted with 20 ml of 50 mM Tris-succinate (pH 5.0) containing 1 mM DTT, 0.1M NaCl, and 0.2% octyl-β-D-glucopyranoside. The pH 5 eluate was concentrated and washed twice with a 10-fold excess of Buffer B in a CF25 Centriflo ultrafiltration cone (Amicon) and brought to 1 ml (10-fold concentration relative to the starting material).

Step 4—Gel Filtration

Affinity-purified farnesyl transferase (~1 $\mu$g) was chromatographed on a Superose 12 column as described in the legend to FIG. 7.

In the enzyme characterization experiments of FIG. 1A, FIG. 1B, FIG. 2A, FIG. 2B, FIG. 3, FIG. 4A, FIG. 4B, FIG. 8, and FIG. 9, a partially purified fraction of farnesyl:protein transferase was used. This enzyme was prepared by Steps 1 and 2 as described above, after which 6 mg of the Mono Q-purified material was concentrated to 2 ml and then loaded onto a 1.6×50-cm Sephacryl S-200 high resolution gel filtration column (Pharmacia LKB Biotechnology). The column was equilibrated with 50 mM Tris-chloride (pH 7.5) containing 1 mM DTT, 0.2M NaCl, 20 μM $ZnCl_2$, and 0.2% octyl-β-glucopyranoside and eluted with the same buffer at a flow rate of 15 ml/hour. Only the peak fraction, containing 1 mg protein and 40% of initial activity, was used for studies.

4. Identification of $^3$H-Isoprenoid Transferred from [$^3$]FPP

A modification of the procedure described by Casey et al. (Casey et al., 1989) was employed as follows: Briefly, two standard transferase reactions of 25-μl each were conducted for 1 hour at 37° C. The mixtures were then pooled, and a 25-μl aliquot from the 50-μl pooled sample was diluted to 250 μl with 2% (w/v) SDS. This mixture was precipitated with an equal volume of 30% TCA, filtered through nitrocellulose, (7 mm disc), washed twice with 250 μl 6% TCA/2% SDS followed by five washes with 5% TCA, digested with 8 μg trypsin, and subjected to cleavage with methyl iodide. The released $^3$H-isoprenoids were extracted into chloroform/methanol and chromatographed on a reverse-phase HPLC system as described in the legend to FIG. 4A and FIG. 4B.

5. Other Methods

SDS polyacrylamide gel electrophoresis was carried out as described by Laemmli (Laemmli, 1970). Gels were calibrated with high range SDS-PAGE standards (Bio-Rad). Protein content of extracts was measured by the method of Lowry, et al. (Lowry et al., 1951) except for that of the affinity-purified material, which was estimated by comparison to the bovine serum albumin marker ($M_r$ 66,000) following SDS gel electrophoresis and Coomassie staining.

6. Results and Discussion

Figure 1B:
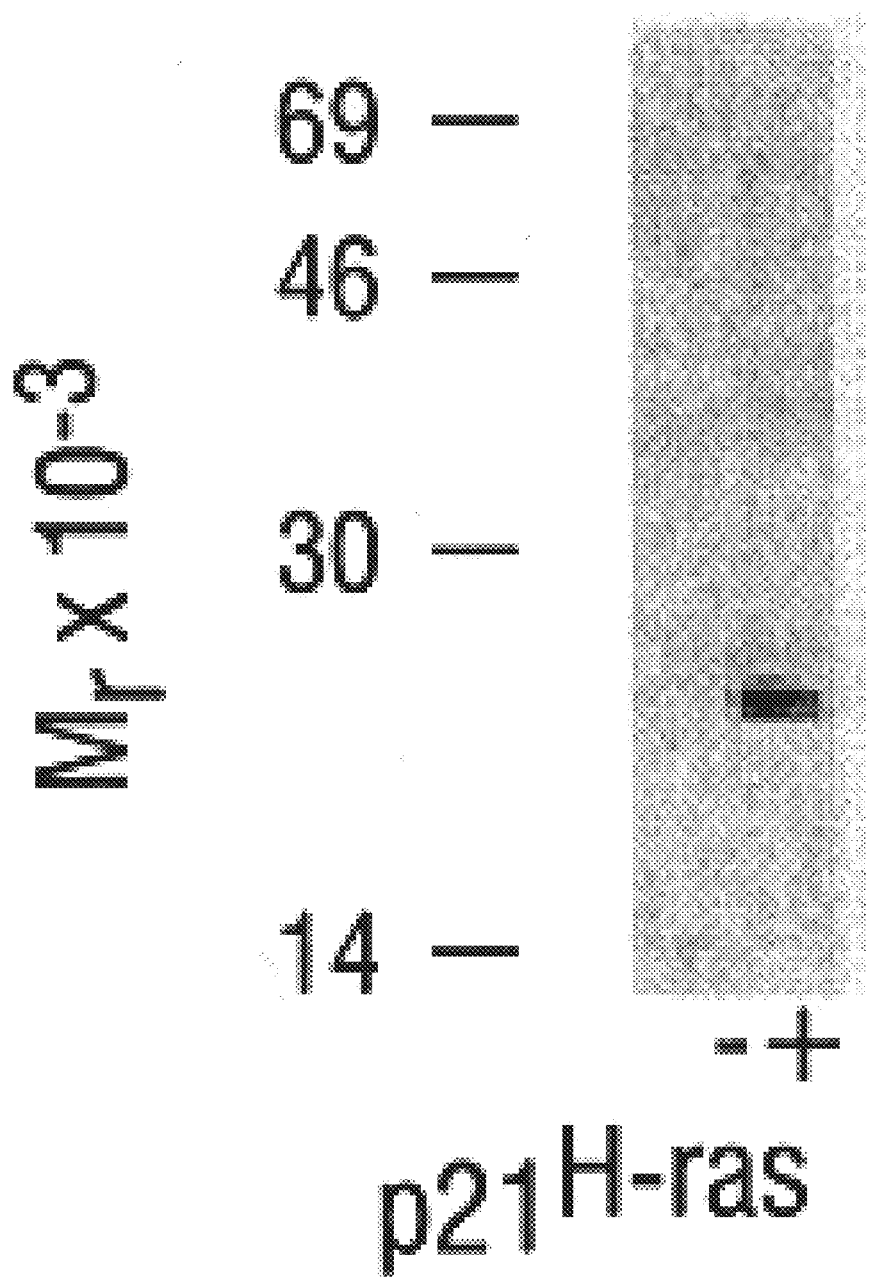
Figure 2A:
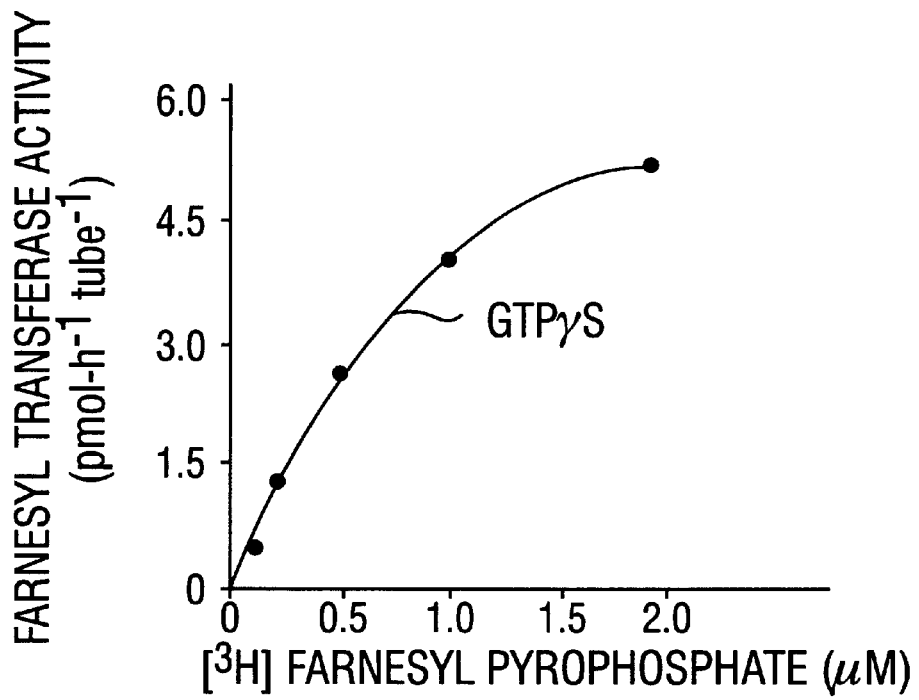
FIG. 2A and FIG. 2B Substrate Saturation Curves for Farnesyl:Protein Transferase. Panel A: each standard reaction mixture contained 1.8 $\mu$g of partially purified farnesyl transferase, 40 $\mu$g $p21^{H-ras}$, [$^3$H]FPP (250,000 dpm); and varying amounts of unlabeled FPP to give the indicated final concentration of [$^3$H]FPP. Panel B: each standard reaction mixture contained 3.2 $\mu$g partially purified farnesyl transferase, 10 pmol [$^3$H]FPP, and the indicated concentration of $p21^{H-ras}$ that had been incubated with 50 $\mu$M of the indicated nucleotide for 45 min at 30° C. and then passed through a G-50 Sephadex gel filtration column at room temperature in buffer containing 10 mM Tris-chloride (pH 7.7), 1 mM EDTA, 1 mM DTT, and 3 mM $MgCl_2$. For both panels, assays were carried out in duplicate for 1 hour at 37° C., and TCA-precipitable radioactivity was measured as described in the Example.
Figure 2B:
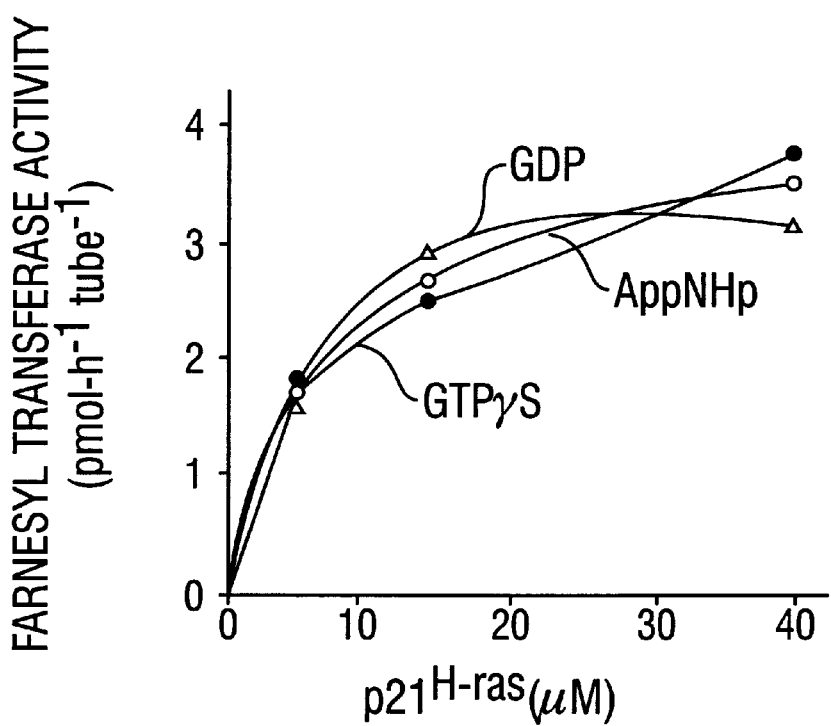

As an initial attempt to identify a farnesyl protein transferase enzyme, rat brain cytosol was fractionated with ammonium sulfate and the active fraction subjected to ion exchange chromatography on a Mono Q column followed by gel filtration on Sephacryl S-200. FIG. 1A and FIG. 1B show that the active fraction from this column incorporated radioactivity from [$^3$H]farnesol into trichloroacetic acid precipitable $p21^{H-ras}$ in a time-dependent fashion at 37° C. The incorporated radioactivity could be visualized as a band of the expected molecular weight of ~21 kDa on SDS polyacrylamide gels (inset). The concentration of [$^3$H]farnesyl pyrophosphate that gave half-maximal reaction velocity was approximately 0.5 μM (FIG. 2A). The half-maximal concentration for $p21^{H-ras}$ was approximately 5 μM, and there was no difference when the $p21^{H-ras}$ was equilibrated with a nonhydrolyzable GTP or ATP analogue or with GDP (FIG. 2B).

Figure 3:
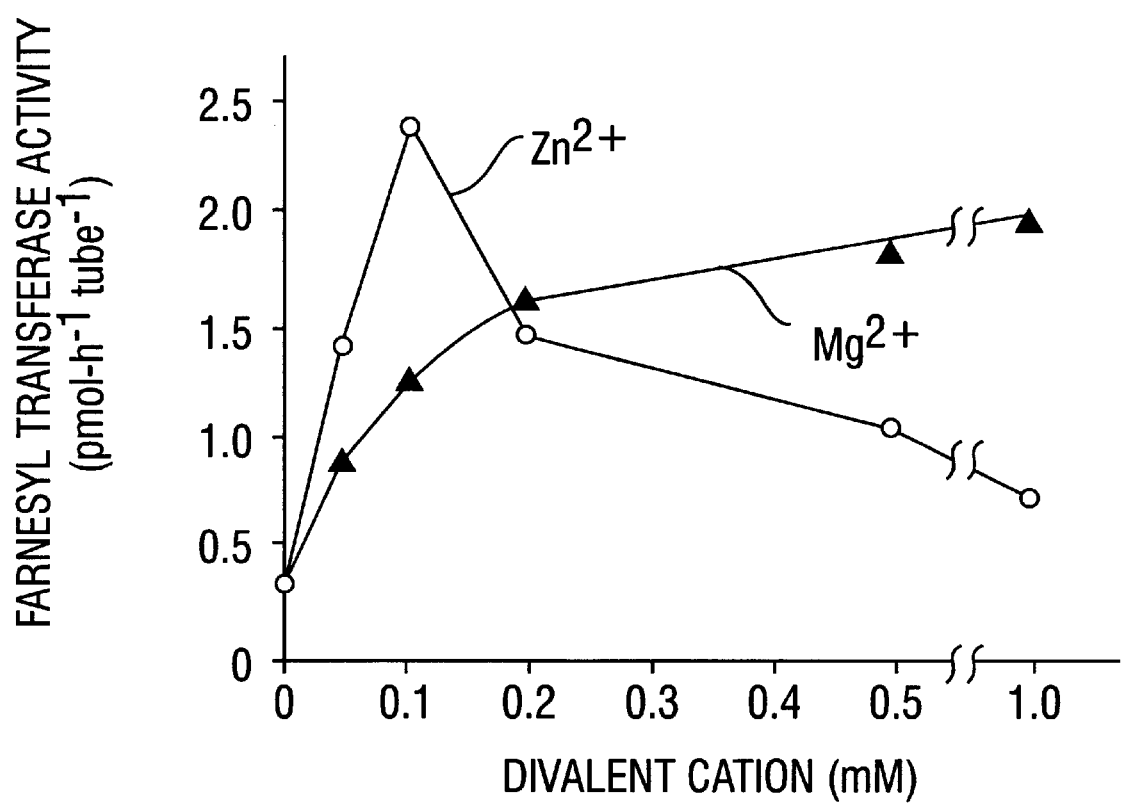
FIG. 3 Divalent Cation Requirement for Farnesyl:Protein Transferase. Each standard reaction mixture contained 10 pmol [$^3$H]FPP, 2.5 $\mu$g of partially purified farnesyl transferase, 40 $\mu$M $p21^{H-ras}$, 0.15 mM EDTA, and the indicated concentrations of either $ZnCl_2$ (●) or $MgCl_2$ (▲). Incubations were carried out in duplicate for 1 hour at 37° C., and TCA-precipitable radioactivity was measured as described in the Examples.

With $p21^{H-ras}$ as a substrate, the transferase reaction was inhibited by 0.15 mM EDTA, and this inhibition was reversed by 0.1 to 1.0 mM concentrations of zinc or magnesium chloride (FIG. 3). At higher concentrations of zinc chloride, inhibition was observed.

Figure 4A:
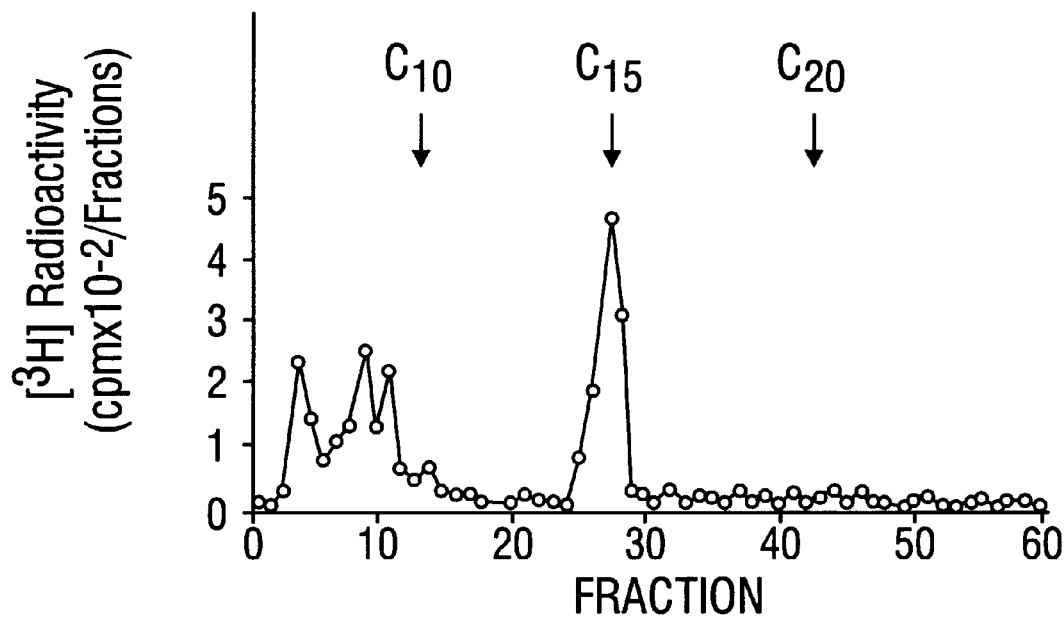
FIG. 4A and FIG. 4B Identification of [$^3$H]FPP-derived Radioactive Material Transferred to $p21^{H-ras}$. Panel A: an aliquot from a standard reaction mixture was subjected to cleavage with methyl iodide as described in the Examples. Panel B: another aliquot was treated identically except methyl iodide was omitted. After cleavage, the extracted material was dried under nitrogen, resuspended in 0.4 ml of 50% (v/v) acetonitrile containing 25 mM phosphoric acid and 6 nmoles of each isoprenoid standard as indicated. The mixture was subjected to reverse phase HPLC (C18, Phenomex) as described by Casey, et al. (1989) except that an additional 10-min wash with 100% acetonitrile/phosphoric acid was used. The isoprenoid standards were identified by absorbance at 205 nm: $C_{10}$, all-trans geraniol; $C_{15}$, all-trans farnesol; $C_{20}$, all-trans geranylgeraniol.
Figure 4B:
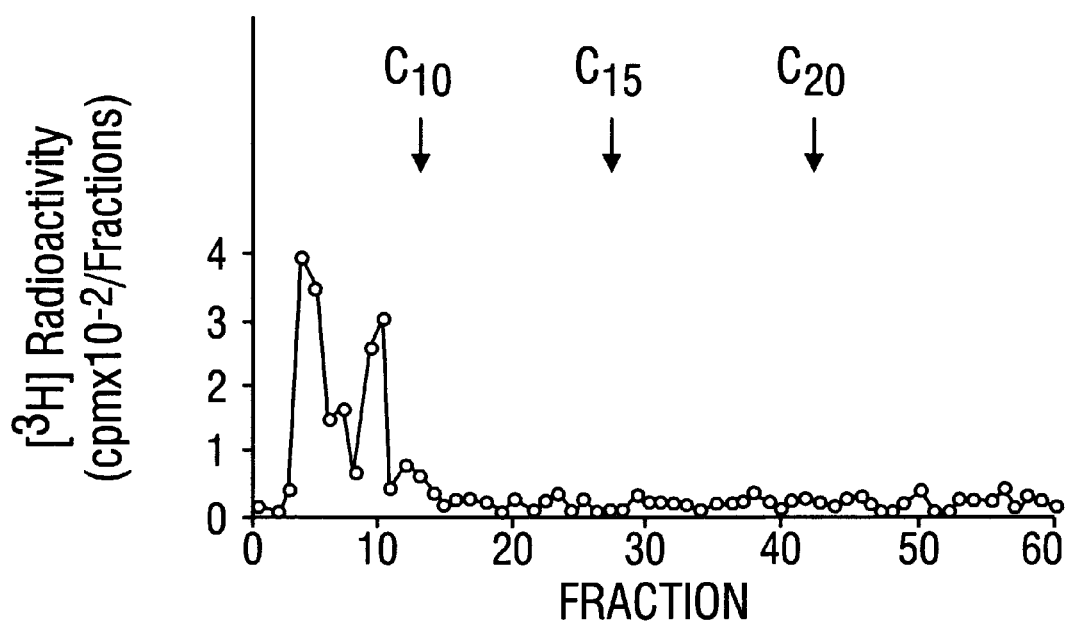

To confirm that the transferred material was [$^3$H]farnesol, the washed trichloracetic acid-precipitated material was digested with trypsin, the radioactivity released with methyl iodide, and the products subjected to reverse-phase HPLC. The methyl iodide-released material co-migrated with an authentic standard of all-trans farnesol ($C_{15}$) (FIG. 4A). Some radioactivity emerged from the column prior to the geraniol standard ($C_{10}$), but this was the same in the presence and absence of methyl iodide treatment. This early-eluting material was believed to represent some tryptic peptides whose radioactivity was not released by methyl iodide.

Figure 5:
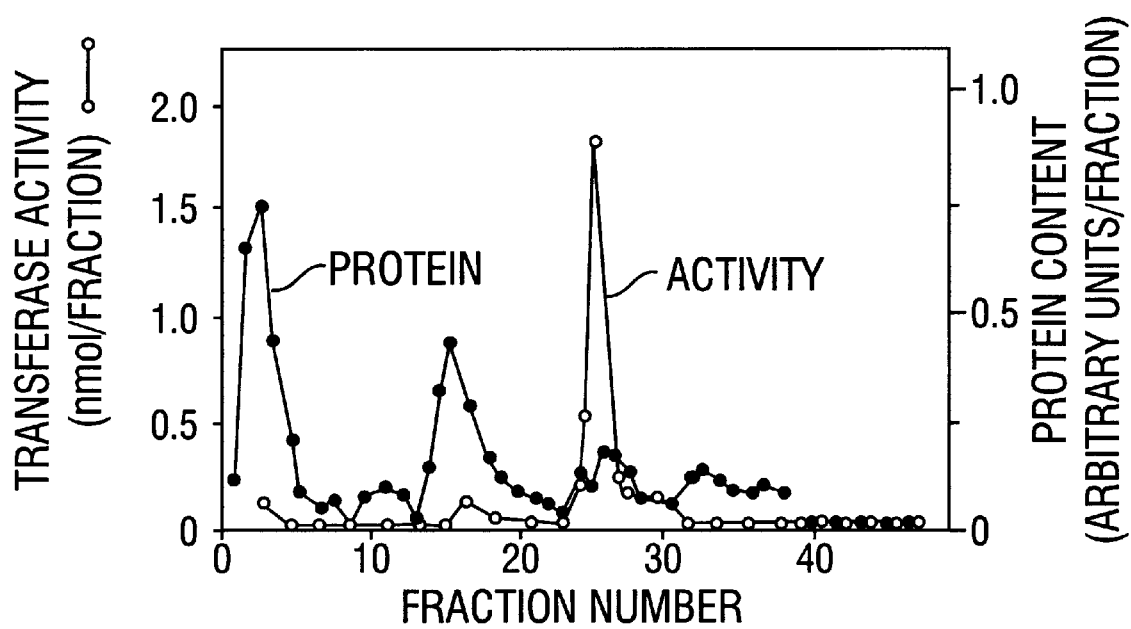
FIG. 5 Chromatography of Farnesyl:Protein Transferase on a Mono Q Column. The 30–50% ammonium sulfate fraction from rat brain (200 mg) was applied to a Mono Q column (10×1-cm) equilibrated in 50 mM Tris-chloride (pH 7.5) containing 1 mM DTT, 20 $\mu$M $ZnCl_2$, and 0.05M NaCl. The column was washed with 24 ml of the same buffer containing 0.05M NaCl, followed by a 24-ml linear gradient from 0.05 to 0.25M NaCl, followed by a second wash with 24 ml of the same buffer containing 0.25M NaCl. The enzyme was then eluted with a 112-ml linear gradient of the same buffer containing 0.25–1.0M NaCl at a flow rate of 1 ml/min. Fractions of 4 ml were collected. An aliquot of each fraction (2 $\mu$l) was assayed for farnesyl:protein transferase activity by the standard method (○). The protein content of each fraction (●) was estimated from the absorbance at 280 mM.

FIG. 5 shows the elution profile of farnesyl transferase activity from a Mono Q column. The activity appeared as a single sharp peak that eluted at approximately 0.35M sodium chloride.

The peak fractions from the Mono Q column were pooled and subjected to affinity chromatography on a column that contained a covalently-bound peptide corresponding to the carboxyl-terminal 6-amino acids of $p21^{K-rasB}$. All of the farnesyl transferase activity was adsorbed to the column, and about 50% of the applied activity was recovered when the column was eluted with a Tris-succinate buffer at pH 5.0.

Table II summarizes the results of a typical purification procedure that started with 50 rat brains. After ammonium sulfate precipitation, mono Q chromatography, and affinity chromatography, the farnesyl transferase was purified approximately 61,000-fold with a yield of 52%. The final specific activity was about 600,000 units/mg.

Figure 6A:
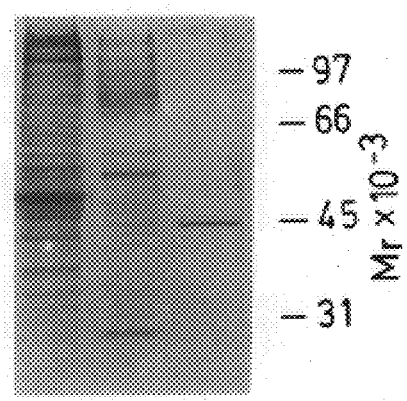
FIG. 6A SDS Polyacrylamide Gel Electrophoresis of Farnesyl:Protein Transferase at Various Stages of Purification. 10 μg of the 30–50% ammonium sulfate fraction (lane 1), 3 μg of the Mono Q fraction (lane 2), and approximately 90 ng of the peptide affinity-column fraction (lane 3) were subjected to SDS-10% polyacrylamide gel electrophoresis, and the protein bands were detected with a silver stain. The farnesyl:protein transferase activity in each sample loaded onto the gel was approximately 0.1, 0.8, and 54 units/lane for lanes 1, 2, and 3, respectively. The molecular weights for marker protein standards are indicated. Conditions of electrophoresis: 10% mini gel run at 30 mA for 1 hour.
Figure 6B:
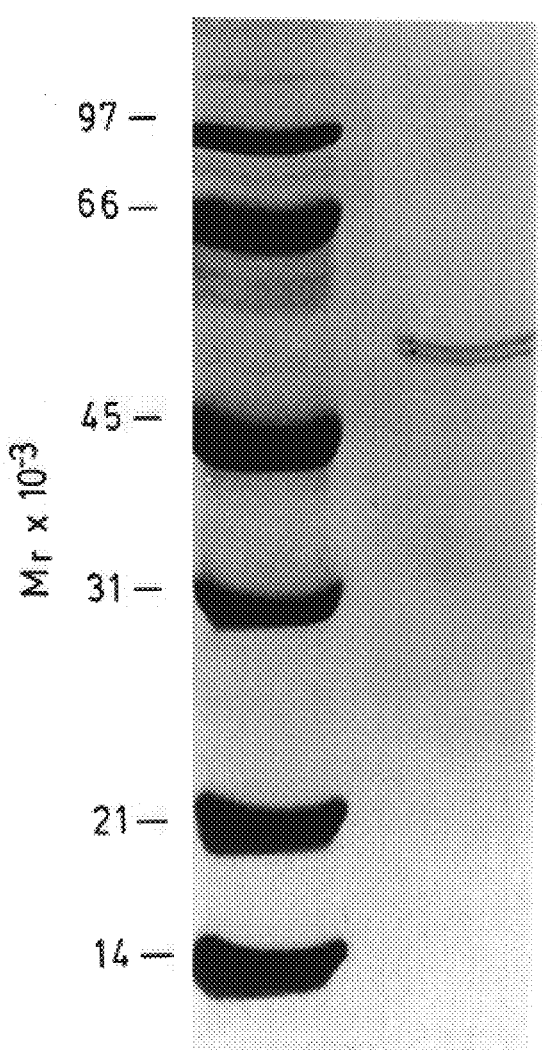
FIG. 6B SDS Polyacrylamide Gel Electrophoresis of Purified Farnesyl:Protein Transferase. 0.7 μg of the peptide affinity-purified-column fraction (right lane) was subjected to SDS-10% polyacrylamide gel electrophoresis, and the protein bands were detected with a Coomassie Blue Stain. The molecular weights for marker protein standards (left lane) are indicated. Conditilank was 3.78 pmol of [$^3$H]FPP p21$^{H-ras}$ formed per hour. Peptides Δ, ○ and ○ correspond to the COOH-terminal 10, 6, and 4 amino acids of wild-type human p21$^{H-ras}$ protein, respectively. Peptides □ and ▲ are control peptides.

FIG. 6A shows the SDS gel electrophoretic profile of the proteins at each stage of this purification as visualized by silver staining. The peptide affinity column yielded a single protein band with an apparent subunit molecular weight of 50,000. When the purified enzyme was subjected to SDS gel electrophoresis under more sensitive conditions, the 50-kDa protein could be resolved into two closely spaced bands that were visualized in approximately equimolar amounts (FIG. 6B).

Figure 7A:
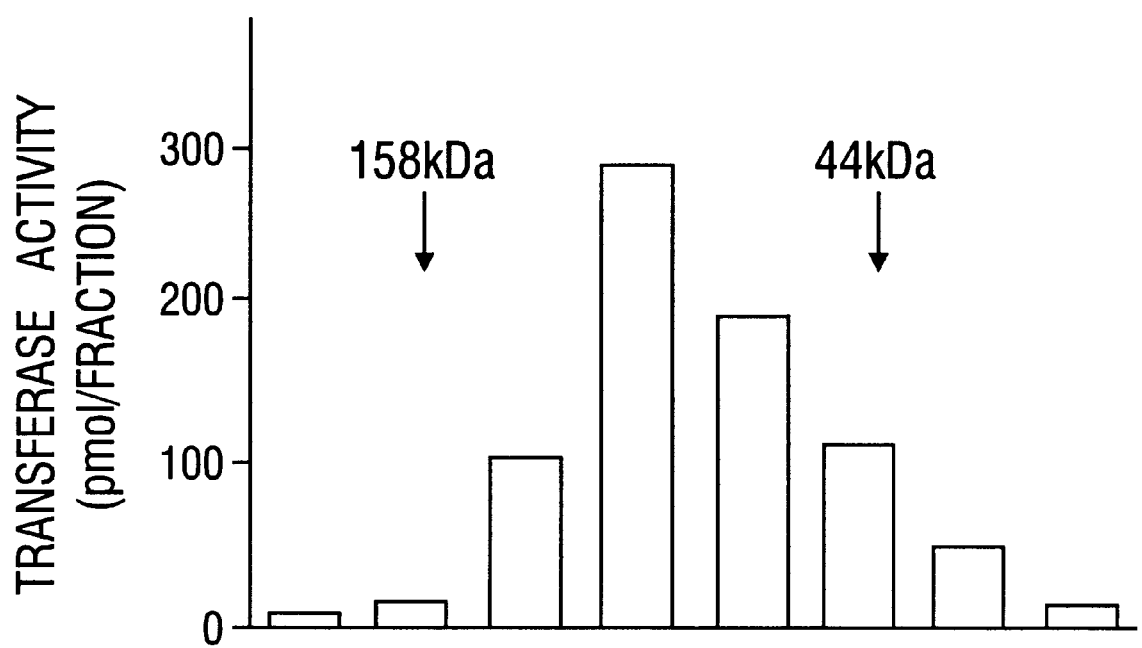
FIG. 7A and FIG. 7B Gel Filtration of Farnesyl:Protein Transferase. Affinity-purified farnesyl transferase (~1 μg protein) was subjected to gel filtration on a Superose-12 column (25×0.5-cm) in 50 mM Tris-chloride (pH 7.5) containing 0.2M NaCl, 1 mM DTT, and 0.2% octyl-β-D-glucopyranoside at a flow rate of 0.2 ml/min. Fractions of 0.5 ml were collected. Panel A, a 6-μl aliquot of each fraction was assayed for farnesyl:protein transferase activity by the standard method except that each reaction mixture contained 0.2% octyl-β-D-glucopyranoside. The column was calibrated with thyroglobulin (670 kDa), γ-globulin (158 kDa), ovalbumin (44 kDa), myoglobin (17 kDa), and vitamin B12 (1.35 kDa). Arrows indicate the elution position of the 158-kDa and 44-kDa markers. Panel B, a 0.42-ml aliquot of each fraction was concentrated to 40 μl with a Centricon 30 Concentrator (Amicon), and 25 μl of this material was then subjected to electrophoresis on an 10% SDS polyacrylamide gel. The gel was stained with silver nitrate and calibrated with marker proteins (far-right lane).
Figure 7B:
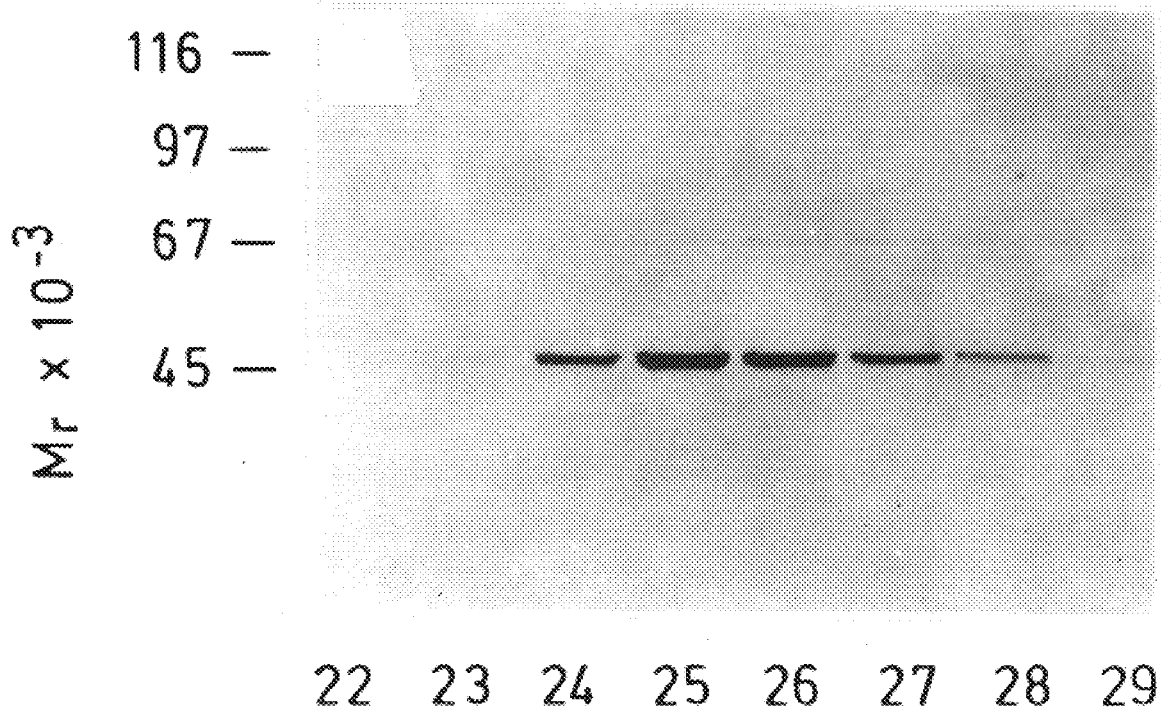
Figure 8:
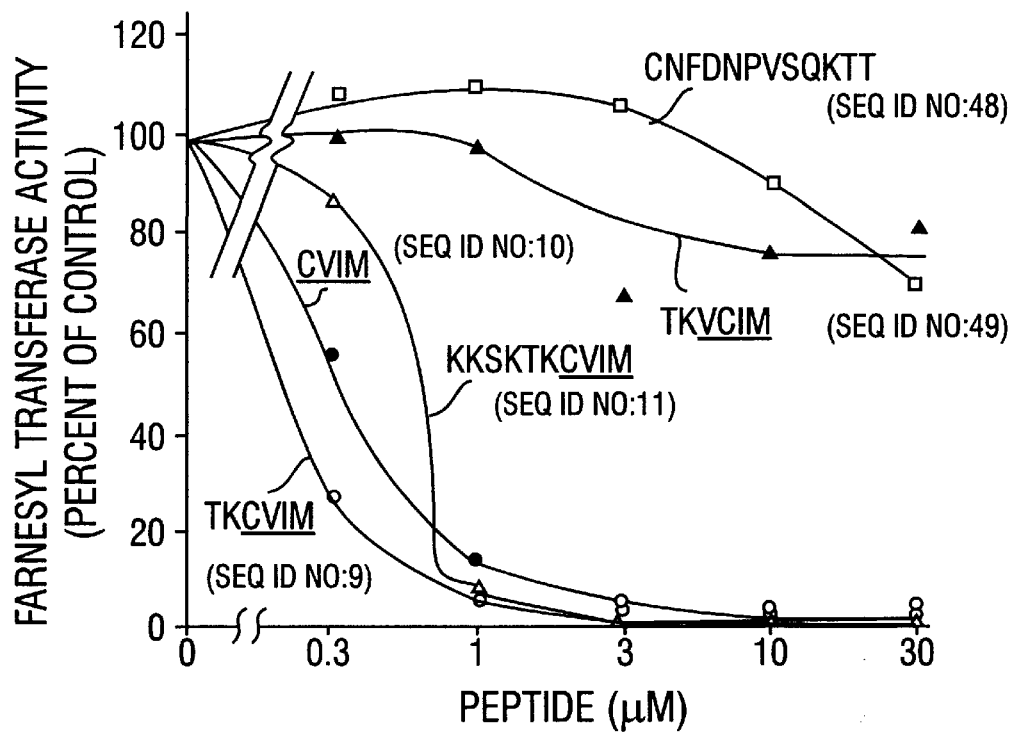
FIG. 8 Inhibition of Farnesyl:Protein Transferase Activity by Peptides. Each standard reaction mixture contained 10 pmol [$^3$H]FPP, 1.8 μg of partially purified farnesyl:protein transferase, 40 μM p21$^{H-ras}$, and the indicated concentration of competitor peptide added in 3 μl of 10 mM DTT. After incubation for 1 h at 37° C., TCA-precipitable radioactivity was measured as described in Experimental Procedures. Each value is the mean of triplicate incubations (no peptide) or a single incubation (+peptide). A blank value of 0.11 pmol/h was determined in a parallel incubation containing 20 mM EDTA. This blank was subtracted from each value before calculating "% of control" values. The "100% of control" value after subtraction of the blank was 3.78 pmol of [$^3$H]FPP p21$^{H-ras}$ formed per h. Peptides A, ○ and ● correspond to the COOH-terminal 10, 6, and 4 amino acids of wild-type human p21$^{H-ras}$ protein (seq id nos:10, 9 and 11), respectively. Peptides □ (CNFDNPVSQKTT; seq id no:48) and A (TKVCIM; seq id no:49) are control peptides.

To confirm that the 50-kDa band was the farnesyl transferase enzyme, the affinity column purified material was subjected to gel filtration. FIG. 7A and FIG. 7B shows that the farnesyl transferase activity and the 50-kDa band co-eluted from this column at a position corresponding to an apparent molecular weight of 70–100 kDa as determined from the behavior of markers of known molecular weight.

TABLE II

PURIFICATION OF FARNESYL:PROTEIN TRANSFERASE FROM RAT BRAIN

| Fraction | Protein mg | Specific Activity units/mg | Total Activity units | Purification -fold | Recovery % |
|---|---|---|---|---|---|
| 30–50% Ammonium Sulfate | 712 | 9.7[a] | 6906 | 1 | 100 |
| Mono Q | 30 | 275 | 8250 | 28 | 119 |
| Affinity Column | ~0.006[b] | 600,000 | 3600 | 61,855 | 52 |

The purification procedure was started with 50 rat brains.
[a]One unit of enzyme activity is the amount of enzyme that transfers 1 pmol of [$^3$H]farnesol from [$^3$H]FPP into acid-precipitable $p21^{H-ras}$ per h under the standard conditions.
[b]Protein concentration was estimated by coomassie blue staining of a SDS polyacrylamide gel using various amounts (0.5 to 2 μg) of bovine serum albumin as a reference standard.

The adherence of the farnesyl transferase to the peptide affinity column suggested that the enzyme was capable of recognizing short peptide sequences. To test for the specificity of this peptide recognition, the ability of various peptides to compete with $p21^{H-ras}$ for the farnesyl transferase activity was measured. The peptide that was used for affinity chromatography corresponded to the carboxyl terminal six amino acids of $P21^{K-rasB}$ (TKCVIM; seq id no:9). As expected, this peptide competitively inhibited farnesylation of $P21^{H-ras}$ (open circles in FIG. 8). The terminal 4-amino acids in this sequence (CVIM; seq id no:10) (closed circles) were sufficient for competition. These two short peptides were no less effective than a peptide that contained the final 10-amino acids of the sequence (KKSKTKCVIM; seq id no:11) (open triangles). The simple transposition of the cysteine from the fourth to the third position from the COOH-terminus of the hexapeptide (TKVCIM; seq id no:9) (closed triangles) severely reduced inhibitory activity. An irrelevant peptide (closed squares) also did not inhibit.

Figure 9:
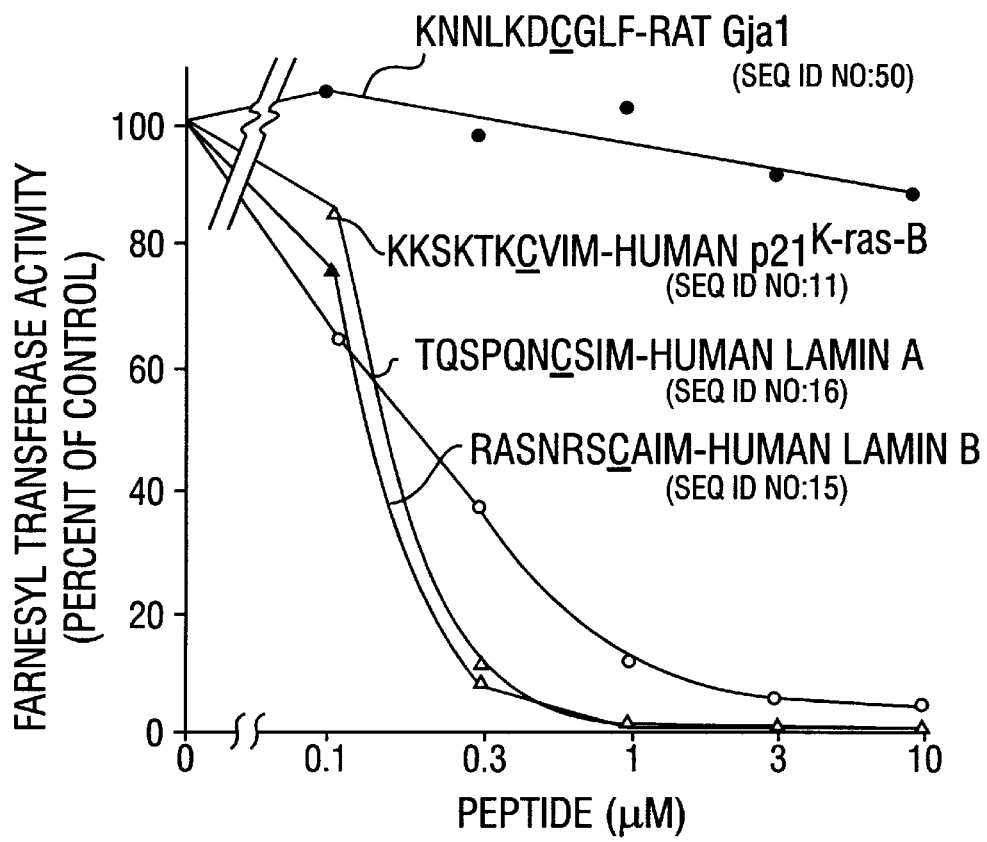
FIG. 9 Inhibition of Farnesyl:Protein Transferase Activity by Peptides. Incubations were carried out exactly as described in the legend to FIG. 8. The "100% of control value" was 2.92 pmol of [$^3$H]farnesyl p21$^{H-ras}$ formed per hour. The blank value was 0.20 pmol/h. Each peptide consisted of the COOH-terminal 10 residues of the indicated protein. Peptide KNNLKDCGLF is seq id no:50; KKSKTKCVIM is seq id no:11; TQSPQNCSIM is seq id no:16; and RASNRSCAIM is seq id no:15.

FIG. 9 compares the inhibitory activities of four peptides of 10-amino acids each, all of which contain a cysteine at the fourth position from the COOH-terminus. The peptides corresponding to the COOH-terminus of human $p21^{K-rasB}$ and human lamin A and lamin B all inhibited farnesylation. All of these peptides are known to be prenylated in vivo (Casey et al., 1989; Farnsworth et al. 1989). On the other hand, the peptide corresponding to the sequence of rat Gial, a 40 kDa G protein that does not appear to be farnesylated in vivo, did not compete for the farnesyl transferase reaction.

In data not shown it was found that the 10-amino acid peptide corresponding to the COOH-terminus of $p21^{H-ras}$ (CVLS seq id no:19), $p21^{N-ras}$ (CVVM; seq id no:18), and $p21^{H-rasA}$ (CIIM; seq id no:17) all competed for the farnesylation reaction.

EXAMPLE II

Further Characterization of Farnesyl:protein Transferase

In the present Example, a series of tetrapeptides were tested for their ability to bind to the rat brain $p21^{H-ras}$ farnesyl:protein transferase as estimated by their ability to compete with $p21^{H-ras}$ in a farnesyl transfer assay. Peptides with the highest affinity had the structure Cys-A1-A2-X, where A1 and A2 are aliphatic amino acids and X is a C-terminal methionine, serine, or phenylalanine. Charged residues reduced affinity slightly at the A1 position and much more drastically at the A2 and X positions. Effective inhibitors included tetrapeptides corresponding to the COOH-termini of all animal cell proteins known to be farnesylated. In contrast, the tetrapeptide CAIL (seq id no:65), which corresponds to the COOH-terminus of the only known examples of geranylgeranylated proteins (neural G protein γ subunits) did not compete in the farnesyl transfer assay, suggesting that the two isoprenes are transferred by different enzymes. A biotinylated hexapeptide corresponding to the COOH-terminus of $p21^{K-rasB}$ was farnesylated, suggesting that at least some of the peptides serve as substrates for the transferase. The data are consistent with a model in which a hydrophobic pocket in the farnesyl:protein transferase recognizes tetrapeptides through interactions with the cysteine and the last two amino acids.

1. Materials and Methods a. Peptides

Peptides were prepared by established procedures of solid-phase synthesis (Stewart et al., 1984) Tetrapeptides were synthesized on the Milligen 9050 Synthesizer using Fmoc chemistry. After deprotection of the last residue, a portion of the resin was used to make the N-acetyl-modified version of CVIM. This was done off-line in a solution of acetic anhydride and dimethylformamide at pH 8 (adjusted with diisopropylethylamine). The acetylated and unacetylated peptides were cleaved with 50 ml of trifluoroacetic acid:phenol (95:5) plus approximately iml of ethanedithiol added as a scavenger. The N-octyl-modified version of CVIM was synthesized on an Applied Biosystems Model 430 Synthesizer using tBoc chemistry. The octyl group was added in an amino acid cycle using octanoic acid. The peptide was cleaved from the resin at 0° C. with a 10:1:1 ratio of HF (mls):resin (g):anisole (ml). The peptides were purified by high pressure liquid chromatography (HPLC) on a Beckman C18 reverse phase column (21.1 cm×15 cm), eluted with a water-acetonitrile gradient containing 0.1% (v/v) trifluouroacetic acid. Identity was confirmed for all peptides by fast atom bombardment (FAB) mass spectrometry. Just prior to use, each peptide was dissolved at a concentration of 0.8 mM in 10 mM dithiothreitol (DTT), and all dilutions were made in 10 mM DTT.

Biotinylated KTSCVIM (seq id no:53) was synthesized on an Applied Biosystems 430A Synthesizer. The biotin group was added after removal of the N-terminal protecting group before cleavage of the peptide from the resin. Specifically, a 4-fold molar excess of biotin 4-nitrophenyl ester was added to the 0.5 g resin in 75 ml dimethylformanide at pH 8 and reacted for 5 hours at room temperature. Cleavage, identification, and purification were carried out as described above.

To synthesize S-acetoamido CVIM (seq id no:10), purified CVIM was dissolved at a final concentration of 1 mM in 0.1 ml of 0.5M Tris-chloride (pH 8.0) containing 15 mM DTT. The tube was flushed with nitrogen for 2 min, sealed, and incubated for 2.5 hours at 37° C. to reduce the cysteine residue, after which iodoacetamide was added to achieve a final concentration of 35 mM. After incubation for 15 min at 37° C., the reaction was stopped by addition of 10 mMDTT. Complete alkylation of CVIM was confirmed by FAB spectrometry and HPLC. The molecular weight of the product corresponded to the expected molecular mass of S-acetoamido CVIM.

b. Assay for Farnesvl:Protein Transferase

The standard assay involved measuring the amount of [$^3$H]farnesyl transferred from all-trans [$^3$H]FPP to recombinant human $p21^{H-ras}$ as described in Example I. Each reaction mixture contained the following concentrations of components in a final volume of 25 µl: 50 mM Tris-chloride (pH 7.5), 50 µM $ZnCl_2$, 30 mM KCl, 1 mM DTT, 30 or 40 µM $p21^{H-ras}$, 15 pmol [$^3$H]FPP (12–23,000 dpm/pmol), 4 to 7.5 µg of partially purified farnesyl:protein transferase (Mono Q fraction, see Example I), and the indicated concentration of competitor peptide added in 3 µl of 10 mM DTT. After incubation for 30–60 min at 37° C., the amount of [$^3$H]farnesyl present in trichloroacetic acid-precipitable $p21^{H-ras}$ was measured by a filter assay as described in Example I. A blank value (<0.6% of input [$^3$H]FPP) was determined in parallel incubations containing no enzyme. This blank value was subtracted before calculating "% of control" values.

c. Transfer of [$^3$H]Farnesyl from [$^3$H]FPP to Biotinylated KTSCVIM Peptide

This assay takes advantage of the fact that peptides containing the Cys-AAX (seq id no:12) motif of ras proteins can serve as substrates for prenylation by farnesyl transferase. A heptapeptide containing the terminal four amino acids of $p21^{K-rasB}$ was chosen as a model substrate since it has a 20 to 40-fold higher affinity for the enzyme than does the COOH-terminal peptide corresponding to p21$^{H-ras}$. A biotinylated peptide is used as substrate so that the reaction product, [$^3$H]farnesylated peptide, can be trapped on a solid support such as streptavidinagarose. The bound [$^3$H] farnesylated peptide can then be washed, separated from unincorporated [$^3$H]FPP, and subjected to scintillation counting.

The biotin-modified KTSCVIM (seq id no:53) is synthesized on an Applied Biosystems 430A Synthesizer using established procedures of solid phase peptide synthesis. The biotin group is added after deprotection of lysine and before cleavage of the peptide from the resin. The identity and purity of the biotinylated peptide is confirmed by quantitative amino acid analysis and fast atom bombardment (FAB) mass spectrometry.

An aliquot of biotinylated KTSCVIM (seq id no:53; 0.4 mg) is dissolved in 0.6 ml of 10 mM sodium acetate (pH 3) buffer containing 1 mM DTT and 50% ethanol to give a final concentration of 0.67 mg/ml or 601 $\mu$M. This solution can be stored at 4° C. for at least 1 month. Immediately prior to use, the peptide solution is diluted with 1 mM DTT to achieve a peptide concentration of 18 $\mu$M. The standard reaction mixture contains the following components in a final volume of 25 $\mu$l: 50 mM Tris-chloride (pH 7.5), 50 $\mu$M ZnCl$_2$, 20 mM KCl, 1 mM DTT, 0.2% (v/v) octyl-$\beta$-glucopryranoside, 10–15 pmol of [$^3$H]FPP (15–50,000 dpm/pmol), 3.6 $\mu$M biotinylated KTSCVIM (seq id no:53), and 2–4 units of enzyme. After incubation at 37° C. for 30–60 min in 0.5-ml siliconized microfuge tubes, the reaction is stopped by addition of 200 $\mu$l of 20 mM Tris-chloride (pH 7.5) buffer containing 2 mg/ml bovine serum albumin, 2% SDS, and 150 mM NaCl. A 25-$\mu$l aliquot of well mixed streptavidin-agarose (Bethesda Research Laboratories, Cat. No. 5942SA) is then added, and the mixture is gently shaken for 30 min at room temperature to allow maximal binding of the [$^3$H]farnesylated peptide to the beads.

The beads are then collected by spinning the mixture for 1 min in a microfuge (12,500 rpm). The supernatant is removed, and the beads are washed three times with 0.5 ml of 20 mM Tris-chloride (pH 7.5) buffer containing 2 mg/ml bovine serum albumin, 4% SDS, and 150 mM NaCl. The pellet is resuspended in 50 $\mu$l of the same buffer and transferred to a scintillation vial using a 200-$\mu$l pipettor in which the tip end has been cut off at an angle. The beads remaining in the tube are collected by rinsing the tube with 25 $\mu$l of the above buffer and adding it plus the pipettor to the vial. A blank value, which consists of the radioactivity adhering to the beads in parallel incubations containing no enzyme, should be less than 0.5% of the input [$^3$H]FPP.

2. Results

Figure 10A:
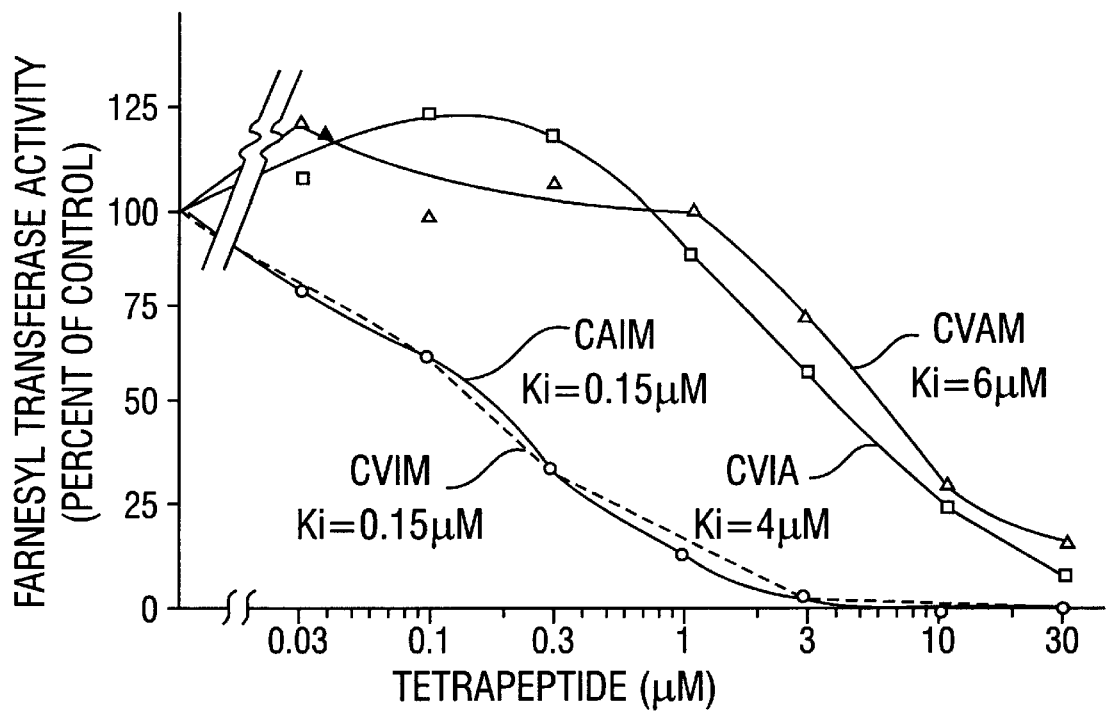
FIG. 10A, FIG. 10B and FIG. 10C Inhibition of Farnesyl:Protein Transferase By Tetrapeptide Analogues of CVIM (seq id no:10). The standard assay mixture contained 15 pmol [$^3$H]FPP, 4 to 7.5 μg partially purified farnesyl transferase, 30 or 40 μM p21$^{H-ras}$, and the indicated concentration of competitor tetrapeptide. After 30 or 60 min, the amount of [$^3$H]farnesyl attached to p21$^{H-ras}$ was measured by trichloracetic acid precipitation as described in the methods section of Example II. Each value is the average of duplicate or triplicate incubations (no peptide) or a single incubation (+peptide). Each tetrapeptide was tested in a separate experiment together with equivalent concentrations of CVIM (seq id no:10). The values for inhibition by CVIM ( . . . ) represent mean values from 21 experiments in which the mean "100% of control" value was 13 pmol min$^{-1}$ mg protein$^{-1}$. $K_i$, concentration of tetrapeptide giving 50% inhibition. Represented are CAIM (seq id no:14); CVIA (seq id no:25); CVAM (seq id no:30); CKIM (seq id no:31); CLIM (seq id no:32); CVLM (seq id no:20); CVIL (seq id no:26); CVKM (seq id no:51); and CVIK (seq id no:52).
Figure 10B:
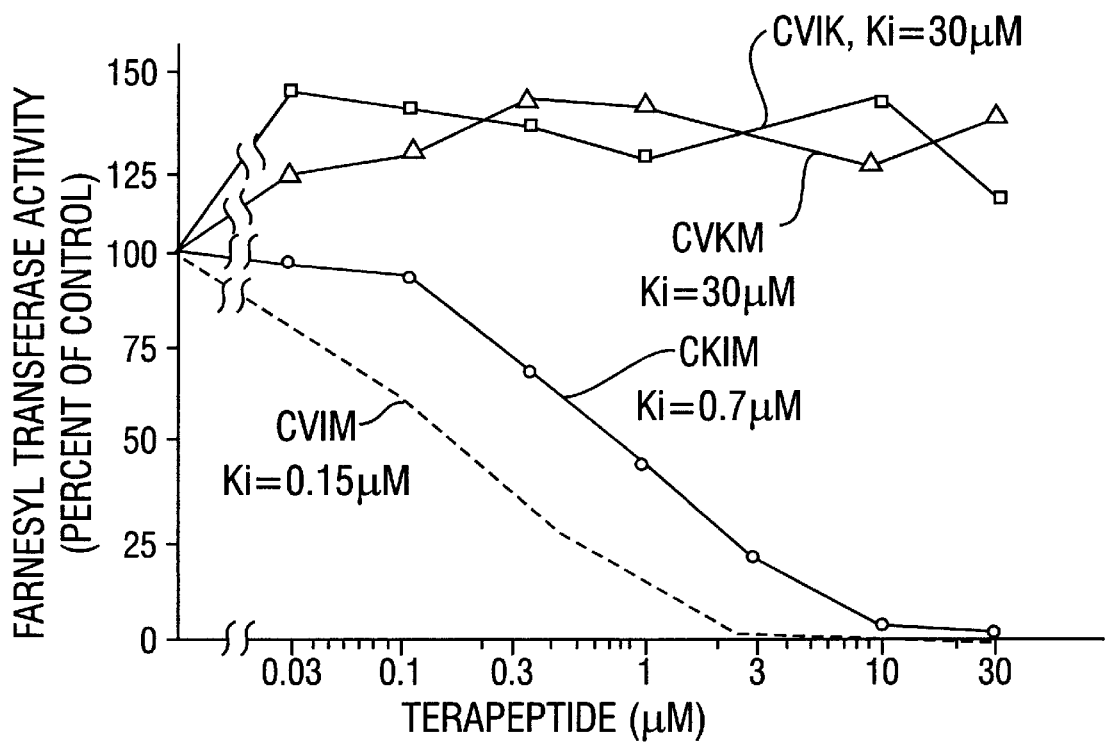
Figure 10C:
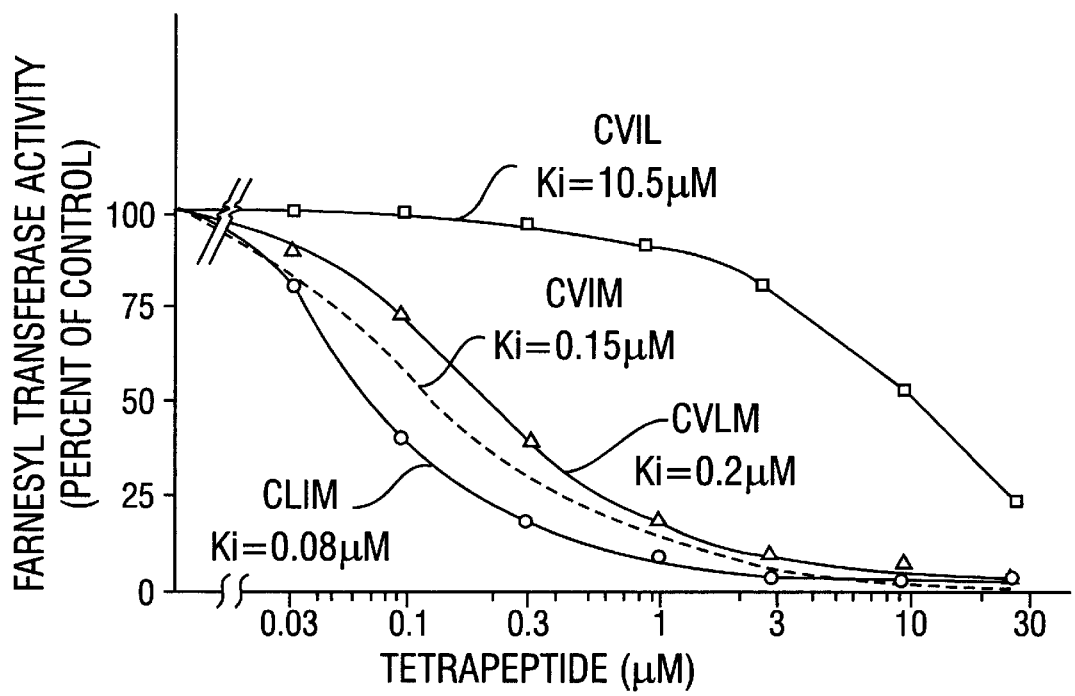

To screen peptides for their affinity for the farnesyl:protein transferase, studies were conducted wherein the ability of the peptides to compete with p21$^{H-ras}$ for acceptance of [$^3$H]farnesyl from [$^3$H]FPP as catalyzed by a partially purified rat brain farnesyl:protein transferase was tested. As a reference point for the peptides, the tetrapeptide CVIM (seq id no:10) corresponding to the COOH-terminal sequence of p21$^{K-rasB}$ was employed. FIG. 10A, FIG. 10B and FIG. 10C show a series of typical experiments in which alanine (Panel A), lysine (Panel B), or leucine (Panel C) was systematically substituted at each of the three positions following cysteine in CVIM (seq id no:10). In each experiment the results were compared with those obtained with CVIM. Alanine and lysine were tolerated only at the A1 position. Insertion of these amino acids at the A2 or X positions decreased the affinity for the enzyme by more than 30-fold as estimated by the concentration required for 50% inhibition. Leucine was tolerated at the A2 position, but it decreased the affinity when inserted at the X position.

Figure 11:
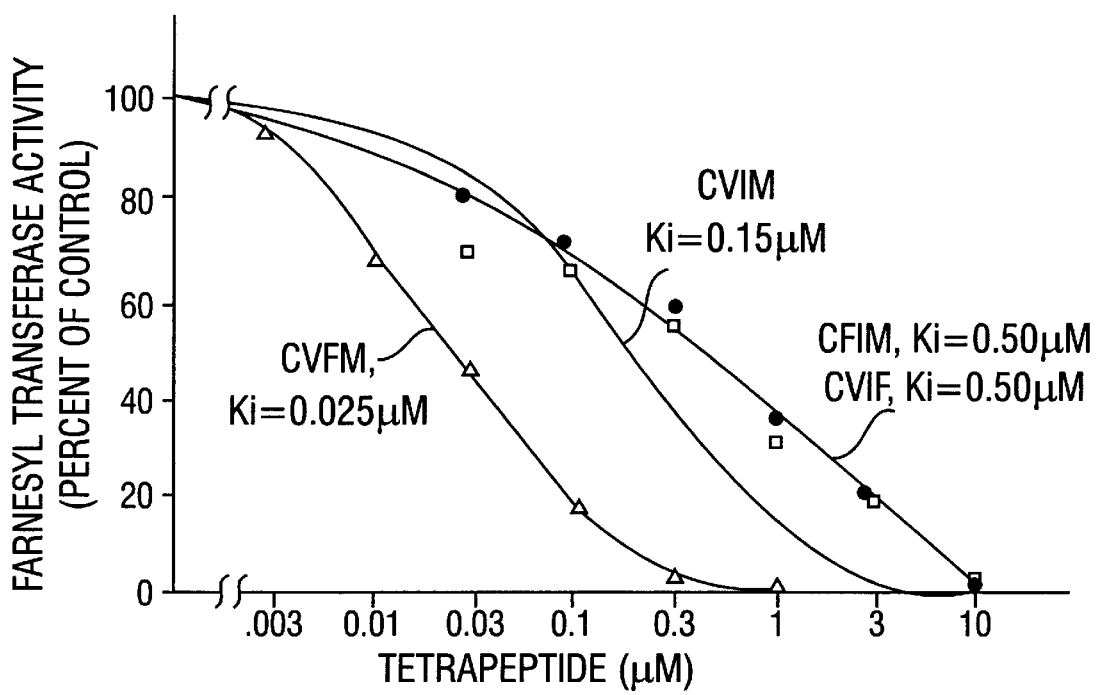
FIG. 11 Inhibition of Farnesyl:Protein Transferase Activity By Phenylalanine-Containing Analogues of CVIM (seq id no:10). Enzyme activity was measured in the presence of the indicated concentration of competitor tetrapeptide as described in the legend to FIG. 10, FIG. 10B and FIG. 10C. Represented are CFIM (seq id no:33); CVFM (seq id no:34); and CVIF (seq id no:35).

The substitution of phenylalanine for isoleucine at the A2 position increased the affinity for the enzyme by 6-fold, with half-maximal inhibition occurring at 25 nM (FIG. 11). No such effect was observed when phenylalanine was inserted at either of the other two positions.

In addition to performing assays with p21$^{H-ras}$ as a substrate, assays were also performed in which the substrate was a biotinylated heptapeptide, KTSCVIM, which contains the COOH-terminal four amino acids of p21$^{H-rasB}$ (Barbacid, 1987). The biotin was attached to the NH$_2$-terminus by coupling to the resin-attached peptide. The [$^3$H]farnesylated product was isolated by allowing it to bind to beads coated with streptavidin as described in section c. above.

Figure 12A:
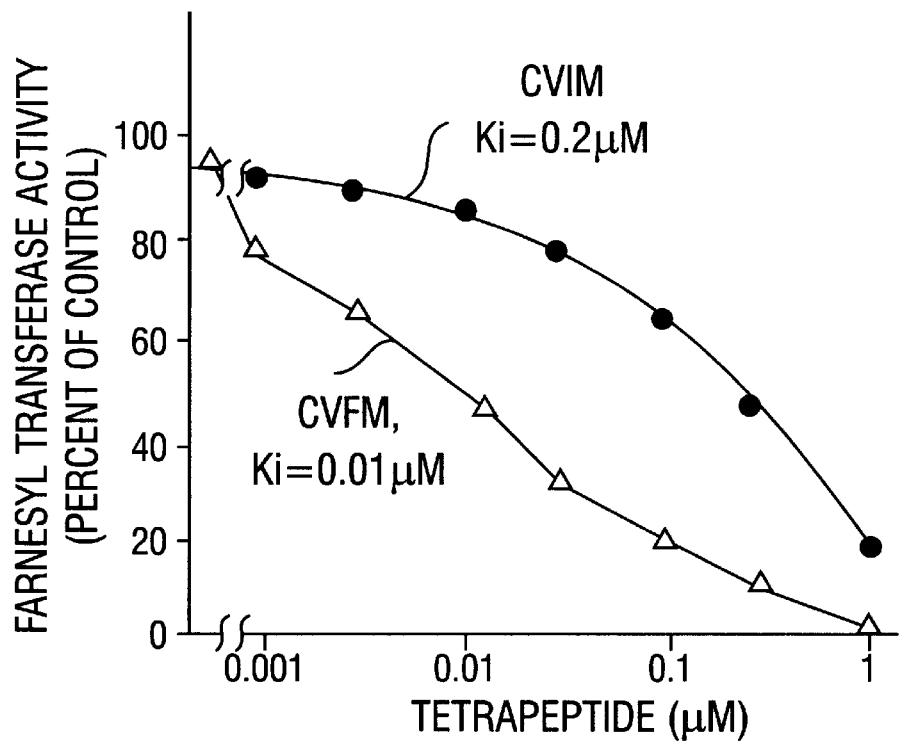
FIG. 12A and FIG. 12B Inhibition of Farnesylation of p21$^{H-ras}$ (A) and Biotinylated KTSCVIM (seq id no:53) (B) By CVFM (seq id no:34). Panel A: Each reaction mixture contained 15 pmol [$^3$H]FPP, 4.5 or 6 ng of purified farnesyl:protein transferase, 40 μM p21$^{H-ras}$, and the indicated concentration of competitor tetrapeptide. After incubation for 30 min at 37° C., the amount of [$^3$H]farnesyl transferred to p21$^{H-ras}$ was measured by the standard filter assay. Values shown are the average of two experiments. The "100% of control" values were 16 and 19 nmol min$^{-1}$ mg protein$^{-1}$, Panel B: Each reaction contained 15 pmol [$^3$H]FPP, 4.5 or 6 ng of purified farnesyl:protein transferase, 3.4 μM biotinylated KTSCVIM (seq id no:53), and the indicated concentration of competitor tetrapeptide. After incubation for 30 min at 37° C., the [$^3$H]farnesyl-labeled peptide was trapped on streptavidin-agarose, washed, separated from the unincorporated [$^3$H]FPP, and subjected to scintillation counting. Values shown are the mean of 3 experiments. The "100% of control" values were 10, 17, and 21 nmol min$^{-1}$ mg protein$^{-1}$. Represented are CVFM (seq id no:34) and CVIM (seq id no:10).
Figure 12B:
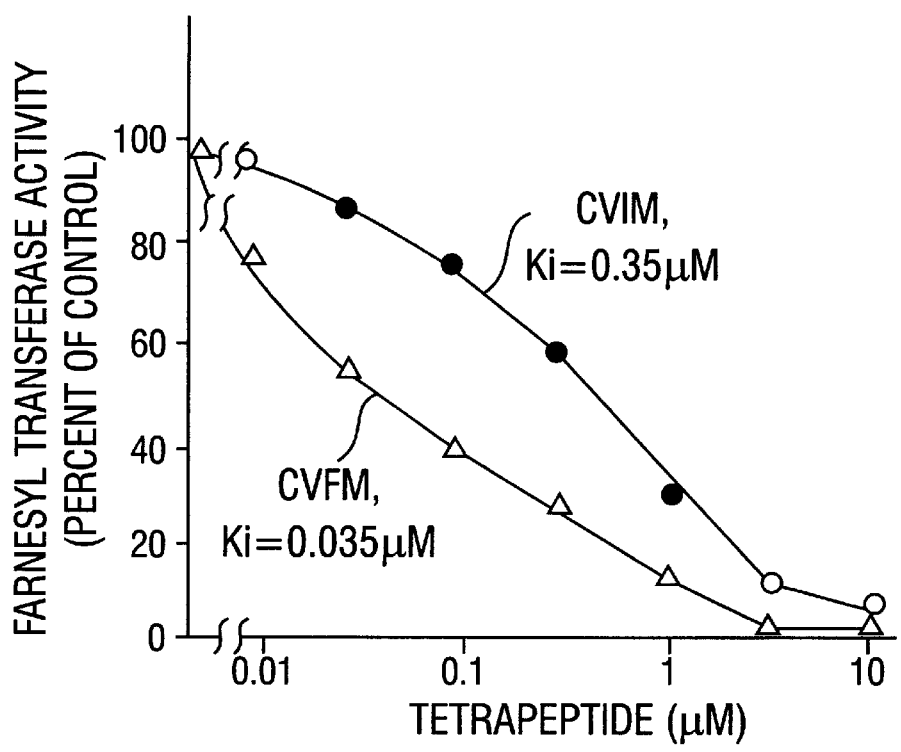

FIG. 12A and FIG. 12B shows that the peptide CVFM (seq id no:34) was more potent than CVIM (seq id no:10) when either p21$^{H-ras}$ or the biotinylated heptapeptide was used as acceptor (Panels A and B, respectively). In contrast to the other studies, which were conducted with a partially purified enzyme, the studies of FIG. 12 were carried out with a homogeneous preparation of affinity-purified farnesyl:protein transferase.

Figure 13A:
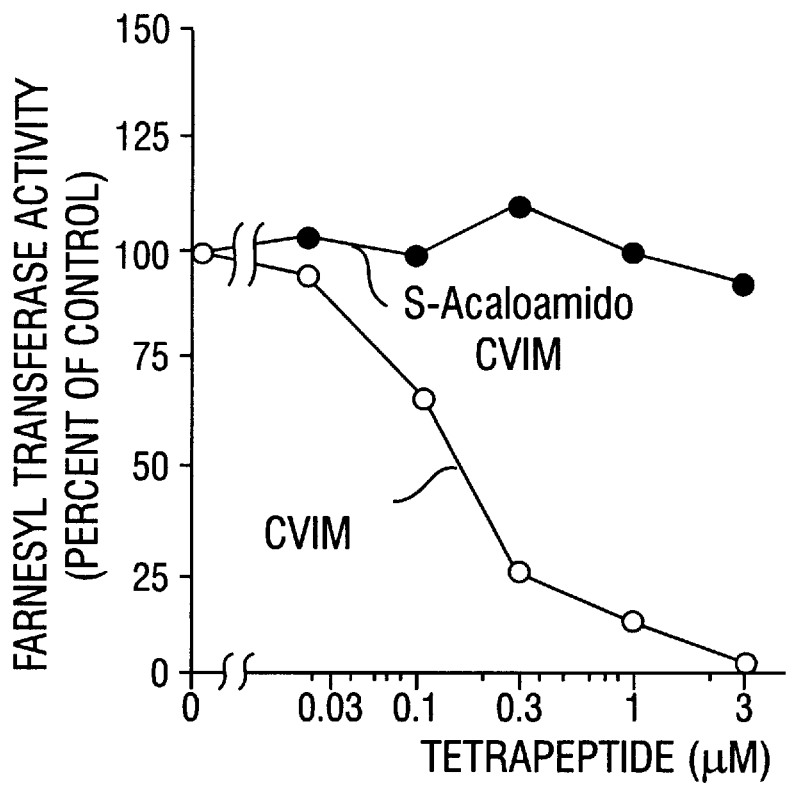
FIG. 13A and FIG. 13B Inhibition of Farnesyl:Protein Transferase By Modified Tetrapeptides. Enzyme activity was measured in the presence of varying concentrations of the indicated tetrapeptide as described in the legend to FIG. 10. The "100% of control" values were 9.3 and 9.2 pmol min$^{-1}$ mg protein$^{-1}$ in Panels A and B, respectively.
Figure 13B:
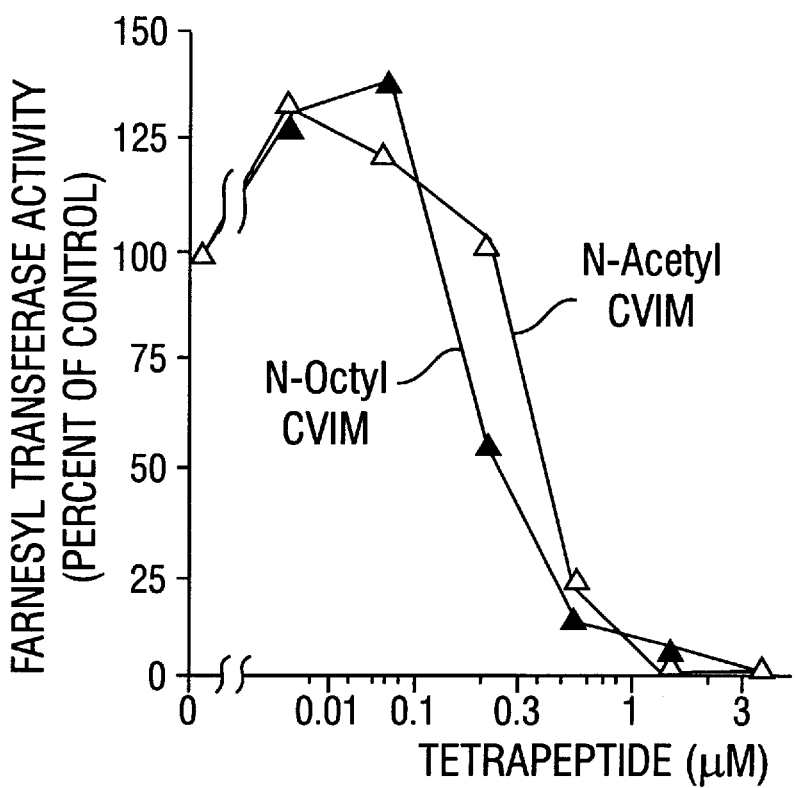

The free sulfhydryl group for the cysteine is likely required for tetrapeptide inhibition, as indicted by the finding that derivitization with iodoacetamide abolished inhibitory activity (FIG. 13A). A blocked NH$_2$-terminus is not required, as indicated by similar inhibitory activity of N-acetyl CVIM and N-octyl CVIM (FIG. 13B) as compared to that of CVIM (FIG. 13A).

Figure 14:
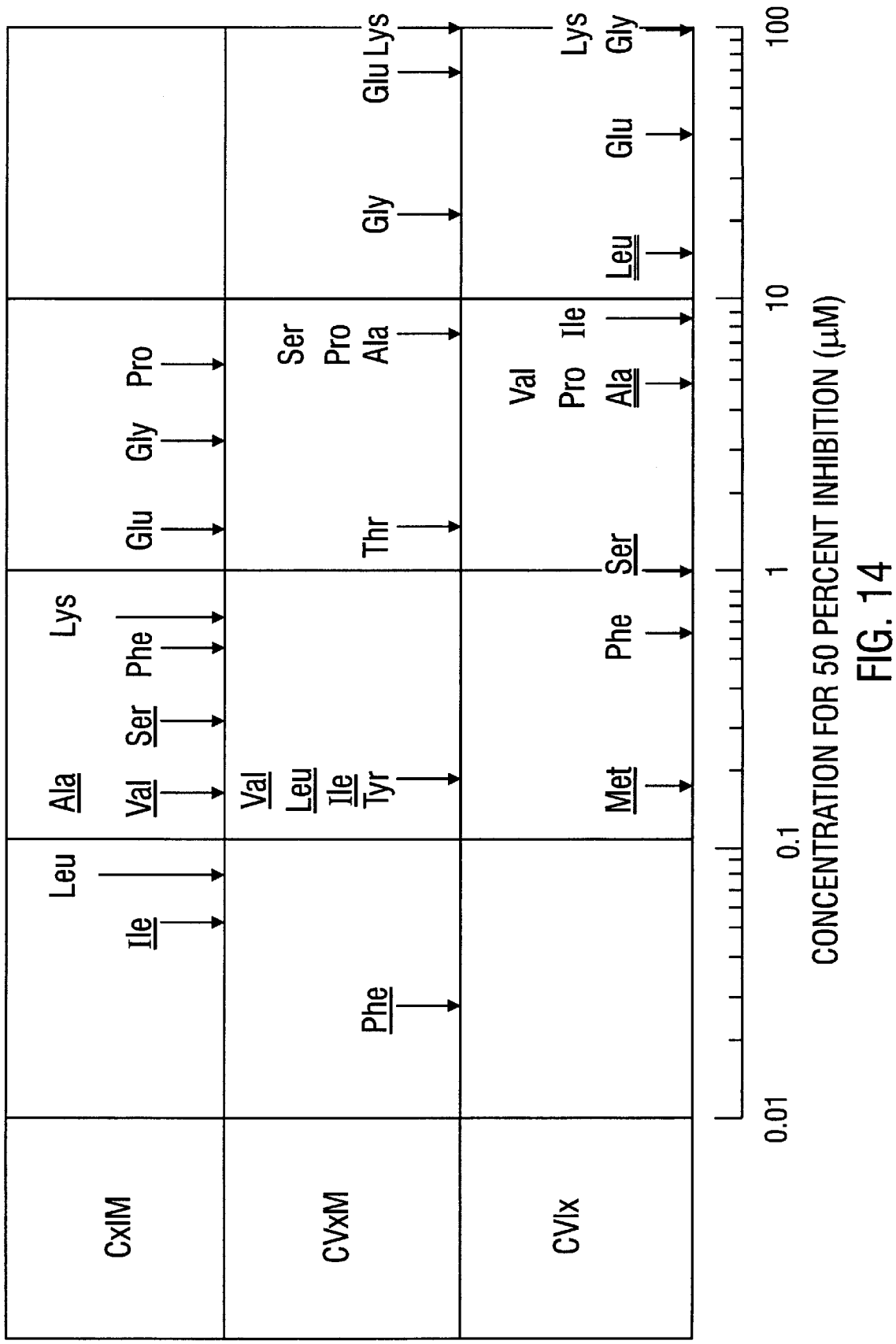
FIG. 14 Inhibition of Farnesyl:Protein Transferase By Tetrapeptides With Single Amino Acid Substitutions in CVIM (seq id no:10). Enzyme activity was measured in the presence of the indicated competitor tetrapeptide as described in the legend to FIG. 10A, FIG. 10B, FIG. 10C and FIG. 11. Each tetrapeptide was tested at seven different concentrations ranging from 0.01 to 100 μM. The concentration of tetrapeptide giving 50% inhibition was calculated from the inhibition curve. The single and double underlines denote tetrapeptides corresponding to the COOH-terminal sequence of mammalian and fungal proteins, respectively, that are candidates for farnesylation (see Table III). CXIM is seq id no:54; CVXM is seq id no:55 and CVIX is seq id no:56.
Figure 15:
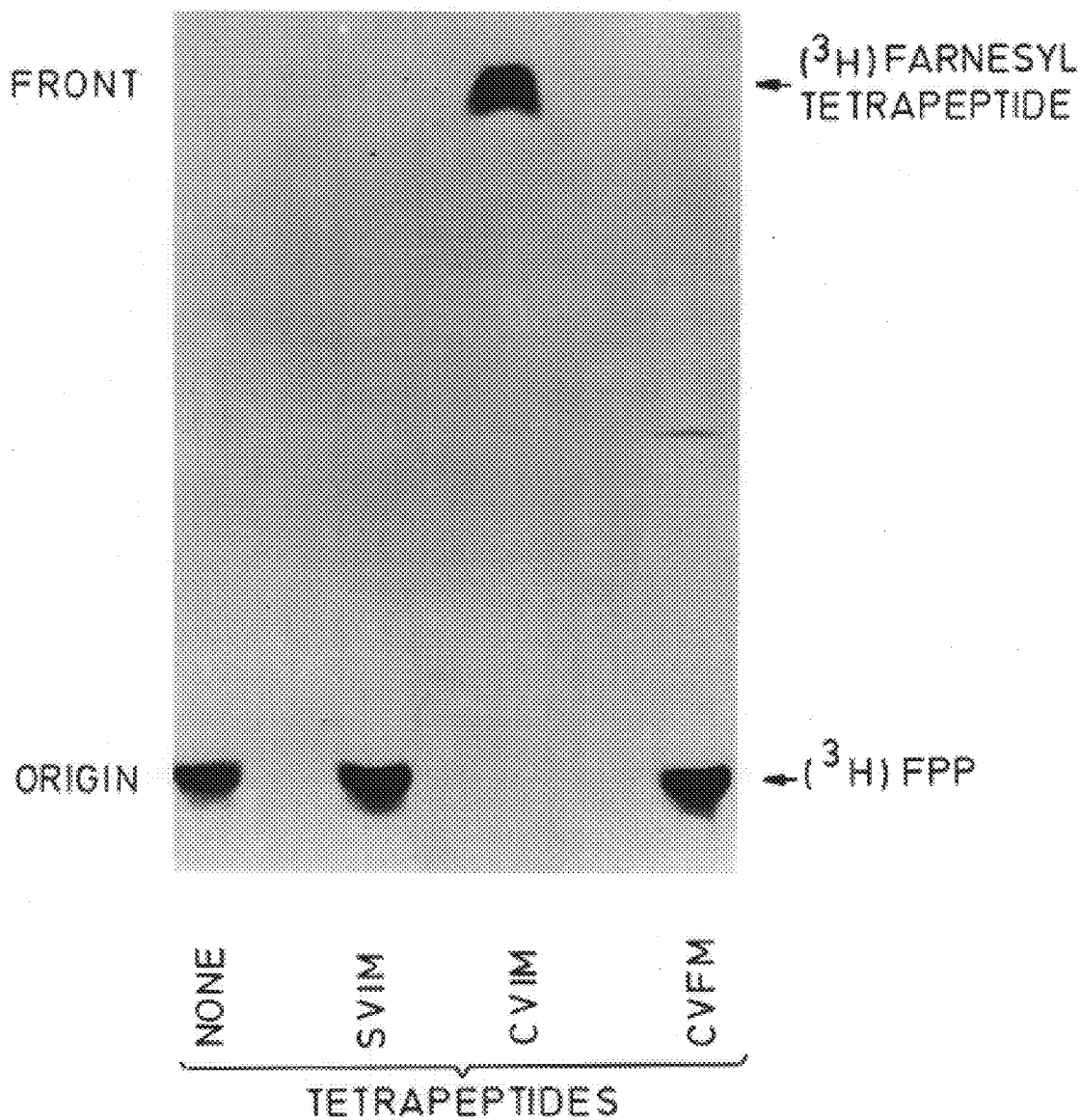
FIG. 15. Farnesylation of CVIM (seq id no:10) but not CVFM (seq id no:34) by Purified Farnesyl:protein Transferase. The standard assay mixture (25 μl) contained 17 pmol [³H]FPP (44,000 dpm/pmol), 5 ng of purified farnesyl:protein transferase, 0.2% (w/v) octyl-β-D-glucoside, and 3.6 μM of the indicated tetrapeptide. After incubation for 15 min at 37° C., the entire reaction mixture was subjected to thin layer chromatography for 4 hours on Polygram SIL G sheet (Brinkmann Instruments) in a solvent system containing N-propanol/concentrated NH₄OH/water (6:3:1). The TLC sheet was then dried, sprayed with ENHANCE Spray (Dupont-New England Nuclear) and exposed to Kodak X-OMAT AR Film XAR-5 for 25 hours at −70° C.

FIG. 14 summarizes the results of all competition assays in which substitutions in the CVIM sequence were made. The results are presented in terms of the peptide concentration required for 50% inhibition. Table III summarizes the results of other experiments in which tetrapeptides corresponding to the COOH-termini of 19 proteins were studied, many of which are known to be farnesylated. The implications of these studies are discussed below in Section 3.

TABLE III

Inhibition of Rat Farnesyl:Protein Transferase by COOH-Terminal Tetrapeptides (Seq id Nos. in parentheses) Corresponding to Known Proteins

| Protein | COOH-Terminal Species | Concentration for 50% Tetrapeptide $\mu$M | Inhibition |
|---|---|---|---|
| *p21$^{K-rasB}$ | Human, mouse | CVIM (10) | 0.15 |
| *p21$^{K-rasA}$ | Human | CIIM (17) | 0.15 |
| p21$^{N-ras}$ | Human | CVVM (18) | 0.15 |
| p21$^{N-ras}$ | Mouse | CVLM (20) | 0.15 |
| *Lamin B | Human, *Xenopus laevis* | CAIM (14) | 0.15 |
| Lamin A | Human, *Xenopus laevis* | CSIM (13) | 0.20 |
| Retinal cGMP phosphodiesterase, $\alpha$ subunit | Bovine | CCVQ (21) | 0.35 |
| *ras1 | *S. cerevisciae* | CIIC (22) | 0.35 |
| *ras2 | *S. cerevisciae* | CIIS (23) | 0.35 |
| *$\gamma$-Subunit of transducin | Bovine | CVIS (24) | 1.0 |
| p21$^{H-ras}$ | Chicken | CVIS (24) | 1.0 |
| p21$^{H-ras}$ | Human, rat | CVLS (19) | 3.0 |
| *a-Mating factor | *S. cerevisciae* | CVIA (25) | 5.0 |
| rap2b | Human | CVIL (26) | 11 |
| Dras | *Dictostelium* | CLIL (27) | 17 |
| rapla/krev1 | Human | CLLL (28) | 22 |
| *Mating factor | *R. Toruloides* | CTVA (29) | 30 |

TABLE III-continued

Inhibition of Rat Farnesyl:Protein Transferase by
COOH-Terminal Tetrapeptides (Seq id Nos. in parentheses)
Corresponding to Known Proteins

| Protein | COOH-Terminal Species | Concentration for 50% Tetrapeptide μM | Inhibition |
|---|---|---|---|
| γ-Subunit of G protein | Bovine | CAIL (65) | 100 |
| HMG CoA reductase-1 | S. cerevisciae | CIKS (66) | >100 |

Enzyme activity was measured in the presence of the indicated tetrapeptide as described in FIG. 10A, FIG. 10B and FIG. 10C. The tetrapeptides, represented by seq id nos: 10*, 13, 14, 17–29, 65 (CAIL) & 66 (CIKS), respectively, were tested at seven different concentrations ranging from 0.03 to 100 μM. The concentration giving 50% inhibition was calculated from the inhibition curve.
*Shown to be farnesylated in vivo.

3. Discussion

The current data extend the observations on the p21$^{ras}$ farnesyl:protein transferase set forth in Example I, and further indicate that the recognition site for this enzyme is restricted to four amino acids of the Cys-A1-A2-X type. As a reference sequence for these studies, the peptide CVIM was used. This peptide inhibited the farnesyl:protein transferase by 50% at a concentration of 0.15 μM. Substitution of various amino acids into this framework yielded peptides that gave 50% inhibitions at a spectrum of concentrations ranging from 0.025 μM (CVFM; seq id no:34) to greater than 50 μM (FIG. 14).

In general, the highest inhibitory activities were achieved when the A1 and A2 positions were occupied with nonpolar aliphatic or aromatic amino acids. This stringency was more severe at the A2 than at the A1 position. Thus, peptides containing lysine or glutamic acid at the A1 position gave 50% inhibition at 0.7 and 1.5 μM, respectively. When these two residues were inserted at the A2 position, the affinity for the enzyme declined by more than 50-fold. Glycine and proline lowered inhibitory activity moderately at the A1 position (50% inhibition at 4 and 8 μM) and somewhat more severely at the A2 position (8 and 20 μM).

The X position showed the highest stringency. In the context of CVIX (seq id no:56), methionine was the preferred residue but phenylalanine and serine were tolerated with only modest losses in activity (0.5 and 1 μM, respectively). Aliphatic resides and proline were disruptive at this position, with 50% inhibitions in the range of 5–11 μM. Glutamic acid, lysine, and glycine were not tolerated at all; 50% inhibition required concentrations above 40 μM.

A study of tetrapeptides corresponding to the COOH-termini of known proteins (Table III) gave results that were generally in keeping with those obtained with the substituted CVIM (seq id no:10) peptides. They provided the additional information that glutamine and cysteine are well tolerated at the X position (CCVQ and CIIC; seq id nos:21 and 22). All of the proteins that are known to be farnesylated in intact cells (indicated by the asterisks in Table III) followed the rules outlined above, and all inhibited farnesylation at relatively low concentrations (5 μM or below) with the exception of the CTVA (seq id no:29) sequence, R. toruloides (Akada et al., 1989). This peptide inhibited the rat brain farnesyl:protein transferase by 50% only at the high concentrations of 30 μM. It is likely that the farnesyl:protein transferase in this fungal species has a different specificity than that of the rat brain.

The peptide CAIL (seq id no:65), which corresponds to the COOH-terminus of the γ-subunit of bovine brain G proteins (Gautam et al., 1989; Robishaw et al., 1989), did not compete efficiently with p21$^{H-ras}$ for farnesylation (Table III). A 50% inhibition at the highest concentration tested (100 μM) was observed. The inhibitory activity was lower than that of CVIL (seq id no:26; 12 μM) or CAIM (seq id no:14; 0.15 μM). Thus, the combination of alanine at the A1 position and leucine at the X position is more detrimental than either single substitution. This finding is particularly relevant since the gamma subunit of G proteins from human brain (Yamane et al., 1990) and rat PC12 cells (Mumby et al., 1990) have been shown to contain a geranylgeranyl rather than a farnesyl. These findings suggest the existence of a separate geranylgeranyl transferase that favors CAIL (seq id no:65) and perhaps other related sequences.

The studies with the biotinyated heptapeptide (FIG. 12B) confirm that at least some of the short peptides act as substrates for the enzyme. The saturation curves relating reaction velocity to the concentration of either p21$^{H-ras}$ or the biotinylated heptapeptide are complex and sigmoidal. The inhibition curves with the various peptides differ from classic competitive inhibition curves. Finally, as mentioned in Example I, the maximal velocity of the purified enzyme is relatively low. These findings suggest that the binding of the peptides to the enzyme is not a simple equilibrium reaction. Rather, there may be a slow binding that requires conformational change.

The observation that the A1 position shows a relaxed amino acid specificity suggests that the residue at this position may not contact the farnesyl transferase directly. Rather, the contacts may involve only the cysteine and the residues at the A2 and X positions. A working model for the active site of the farnesyl:protein transferase places the peptide substrate in an extended conformation with a largely hydrophobic pocket of the enzyme interacting with the X group of the CAAX-containing substrate.

EXAMPLE III

Recombinant Cloning of the Rat Farnesyl:protein Transferase α and β Subunit cDNAs This example demonstrates the recombinant cloning of cDNAs corresponding to both the α and β subunit of rat farnesyl:protein transferase. The method employed by the inventors involved the application of the peptide sequence information, as detailed above, to prepare specific primers for PCR-based sequencing, which sequences were then used for the construction of probes with which to screen cDNA libraries. The cloning of each of these cDNAs by the inventors' laboratory has recently been reported (Chen et al., 1991).

1. Methods a. General Methods

General molecular biological techniques were employed in connection with the cloning reactions described below, as set forth in Sambrook et al., (1989). cDNA clones were subcloned into bacteriophage M13 or plasmid pUC vectors and sequenced by the dideoxy chain termination method (Sanger et al., 1977) using the M13 universal sequencing primer or gene specific internal primers. Sequencing reactions are preferably performed using a modified bacteriophage T7 DNA polymerase (Tabor et al., 1987) with $^{35}$S-labeled nucleotides, or Taq polymerase with fluorescently labeled nucleotides on an Applied Biosystems Model 370A DNA Sequencer.

For the isolation of total cellular RNA from rat tissues, the inventors preferred to employ the guanidinium thiocyanate/

CsCl centrifugation procedure (Glisin et al., 1974). Whereas for the isolation of RNA from cell lines, the guanidinium HCl method was found to be preferable (Chirgwin et al., 1979). The isolation of poly A$^+$ RNA by oligo(dT)-cellulose chromatography was achieved by the methods described in Sambrook et al. (1989) and Aviv et al. (1972). Northern blot hybridization using single-stranded $^{32}$P-labeled probes was carried out as described by Lehrman et al. (1987). A cDNA probe for rat glyceraldehyde-3-phosphate dehydrogenase was obtained from Karl Normington, (University of Texas Southwestern Medical Center at Dallas).

Polyclonal antisera, specific for either the α or β subunit of farnesyl transferase, were prepared by immunizing rabbits with synthetic peptides derived from each specific subunit. Antibody Y533 was raised against a synthetic peptide with the sequence LQSKHSRESDIPASV (seq id no:67), derived from the predicted amino acid sequence of a cDNA clone of the α subunit. Antibody X287 was raised using the synthetic peptide IQATTHFLQKPVPGFEE (seq id no:68), derived from a tryptic digest of the β subunit. Each peptide was coupled to Keyhole Limpet hemocyanin using maleimidobenzoic acid N-hydrosuccinimide ester (Signa Chemical Co.) (Harlow & Lane 1988). For each antibody, three New Zealand White rabbits were immunized with 600 μg of coupled peptide in Freund's complete adjuvant. Immunoblot analysis was performed as described in (Seabra et al., 1991; Chen et al., 1991).

Rat PC12 pheochromocytoma cells, rat KNRK cells (CRL 1569), and human embryonic kidney 293 cells were obtained, respectively, from Thomas Sudhof (University of Texas Southwestern Medical Center at Dallas), the American Type Culture Collection, and Arnold J. Berk (University of California, Los Angeles).

b. PCR and Probe synthesis

Figure 16B:
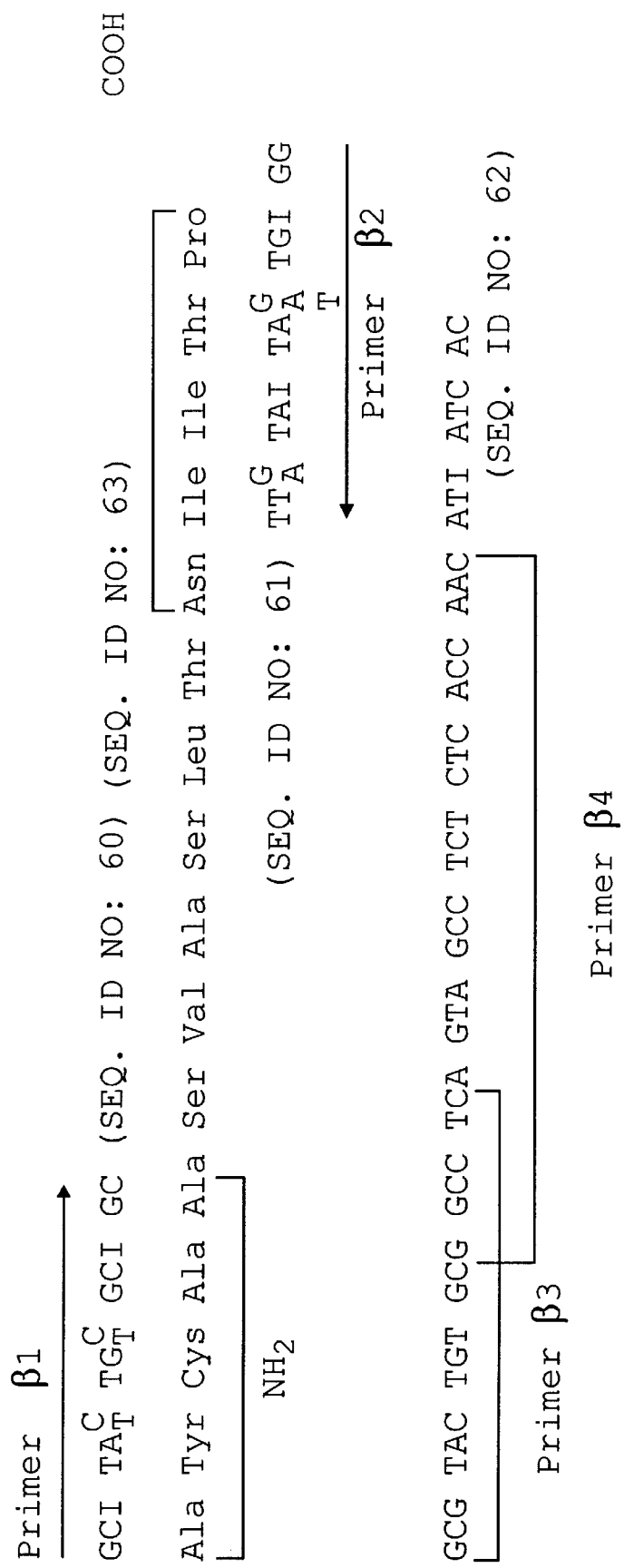

To derive a sequence for constructing an appropriate probe, rat genomic DNA may be used as a template for PCR as described by Saiki et al. (1988) and Lee et al. (1988). The approach used by the inventors was to sequence a portion of the α or β subunit genes through the use of appropriate PCR primers, based on a consideration of the peptide sequences (shown in Table I). Thus, PCR was used to obtain the rat genomic DNA sequences that encoded tryptic peptides derived from either the purified α or β subunits of rat farnesyl transferase (FIG. 16A and FIG. 16B). For the both the α and β sequences, the PCR primers were synthesized based on the NH$_2$-and COOH-terminal sequences of the peptides shown in FIG. 16A and FIG. 16B, and included the degenerate inosine codons indicated (FIG. 16A and FIG. 16B). PCR primers were end-labeled with [γ-$^{32}$P]ATP. Each of the amplified DNA fragments were eluted from 12% acrylamide gels and sequenced by the method of Maxam and Gilbert (Maxam et al., 1980). Translation of the nucleotide sequences between the two primers yielded peptides with amino acid sequences identical to those of the peptides shown (FIG. 16A and FIG. 16B).

Using the DNA sequences of the PCR products, the inventors then synthesized an oligonucleotide probe that would hybridize with the region corresponding to the peptide, for use in the direct screening of the library. For the α subunit, a 38-mer probe with the nucleotide sequence: 5'-ATIGAGTTAAACGCAGCCAACTATACGGTCTGGCA-CTT-3', (a specific example in accordance with residues 6–54 of seq id no:64), was synthesized. Whereas for the β subunit, two primers, designated primer β3 and primer β4 were synthesized with the respective nucleotide sequences: 5'-GCGTACTGTGCGGCCTC-3' (residues 1–17 of seq id no:62) and 5'-GGCCTCAGTAGCCTCTCTCACCAAC-3' (residues 12–36 of seq id no:62).

The primers for the β subunit were used for 3'-end amplification of cDNA as described by Frohman et al. (1988). Poly(A)+RNA from rat KNRK cells was reverse transcribed using a (dT)$_{17}$-adaptor, 5'-GACTCGAGTCGACATCGA(T)$_{17}$-3' (seq id no:69). The 50 μl reaction mixture, containing 4 μg poly(A)+RNA, 2.5 μg (dT)$_{17}$-adaptor, and 100 units of Moloney murine leukemia virus reverse transcriptase (Bethesda Research Laboratories), was incubated at 37° C. for 1 hour. Reverse transcribed cDNA was diluted 50-fold with 10 mM Tris-HCl at pH 8.0, 1 mM EDTA, and subjected to specific PCR amplification as follows. 101 of diluted cDNA, 25 pmol of adaptor primer (5'-GACTCGAGTCGACATCG-3'; residues 1–17 of seq id no:69), and 25 pmol of primer 3 were boiled, after which PCR was carried out for 40 cycles (95° C., 40 sec; 58° C., 1 min; 72° C., 3 min) with TaqI polymerase. Amplified PCR products were subjected to electrophoresis on an agarose gel, transferred to a nylon membrane, and probed with $^{32}$P-labeled primer 4. The hybridizing DNA fragment was eluted, extracted with phenol/chloroform, and used as a template for a second PCR reaction. The reaction using 25 pmol each of adaptor primer and primer 4 was carried out with the same amplification protocol as described above. The reamplified DNA fragment was gel-purified, cleaved with RsaI or TaqI, and subcloned into an M13 vector for DNA sequencing and for subsequent generation of the single-stranded M13 probe that is referred to as Probe B. The DNA sequence of the PCR-derived clone was also used to generate a 50-mer oligonucleotide probe that is designated Probe A. Probes A and B were then used to screen cDNA libraries in order to obtain a full-length β subunit cDNA (see β subunit cloning section, below).

c. cDNA Libraries and Cloning

Rat PC12 cell poly(A$^+$) RNA and oligo (dT)-primed KNRK cell double-stranded cDNA libraries were constructed in bacteriophage λgt10, using a cDNA synthesis kit from Invitrogen. These cells were preferred because the inventors believed them to be rich in farnesyl:protein transferase mRNA. Although numerous convenient methods are known for the construction of cDNA libraries, the inventors utilized the above kit from Invitrogen as they thought it to be a particularly convenient method. The cDNA itself was prepared using both oligo(dT)- and random hexamer-primed cDNA, then ligated to a suitable linker, with the EcoR1/Not1 linker being preferred in this case. cDNAs larger than 1 kb were isolated by size fractionation using a 1% agarose gel and ligated into EcoR1-cleaved λgt10 DNA (Stratagene), in order to complete the construction of the cDNA-containing vectors for library preparation. After in vitro packaging of the recombinant lambda phage with a DNA packaging extract (Stratagene), phage were plated out on host strain *E. coli* C600 hfl$^-$ cells.

α subunit cloning

Approximately 1×10$^6$ plaques of the rat brain library were screened. Duplicate filters were hybridized in 6×SSC (1×SSC=150 mM NaCl/15 mM Na citrate, at pH 7.0) with 1×10$^6$ cpm/ml of $^{32}$P-labeled probe (see above). One positive clone, λRB-17, with an insert of 1.4 kb was identified and plaque purified. Phage DNA from a plate lysate was subcloned into bacteriophage M13 and pBluescript vectors for DNA restriction mapping and sequencing (Sanger et al., 1980).

As the clone first obtained was not a full-length clone, 5'-end amplification was employed to produce the complete sequence, as described in Ref 34. Firstly, an M13 probe corresponding to the 5' end of λRB-17 was used to screen the KNRK cell library. Replicate filters were hybridized in 50% (v/v) formamide containing 1×10⁶ cpm/ml of the probe. Positive clones were analyzed by PCR, and the clone with the longest insert (λKNRK-3) was purified and subcloned for analysis. A 5' Rapid Amplification of cDNA End procedure (5 RACE) (34) was used to extend the 5' end of λKNRK-3. An M13 probe derived from the amplification product (RACE-5') was then used to screen a rat testis library (purchased from Clontech), yielding λRTH, which extended to nucleotide position 53.

To obtain the extreme 5' end of the cDNA, a primer-extension λgt10 library was constructed from rat testis poly(A)⁺ RNA. First stand synthesis was primed with an oligonucleotide corresponding to a sequence near the 5'-end of RACE-5' using Maloney murine leukemia virus reverse transcriptase. After incubation at 37° C. for 1 h, the reaction was heated at 70° C. for 5 min. Five units of Thermostable rTth Transcriptase (Perkin-Elmer) was then added, and the reaction continued at 70° C. for 30 min. After second strand synthesis, the cDNAs were ligated to an EcoRI/NotI linker. Excess linkers were removed by Centricon 100 Microconcentrator (Amicon). Approximately 5×10⁵ plaques were screened with a ³²P-labeled probe corresponding to nucleotides 54–104, which was obtained from the sequence of λRTH. Twenty-five positive clones were identified. Phage DNA was prepared from plate lysates, and the insert from one of the longest clones, λPE-7, was subcloned for sequencing (Sanger et al., 1980).

β subunit cloning

Approximately 5×10⁵ plaques were transferred to replicate filters. One filter was hybridized in 10% (v/v) formamide with 1×10⁶ cpm/ml of a ³²P-labeled 50-mer oligonucleotide probe (Probe A; described above). The other filter was hybridized in 50% formamide with 1×10⁶ cpm/ml of a single-stranded M13 probe (Probe B; described above). One positive clone (λdT-7) with an insert of ~2.3 kb was identified with both probes and plaque purified. Phage DNA isolated from the plate lysate of λdT-7 was subcloned into M13 and pUC vectors for sequencing and restriction mapping.

To obtain the extreme 5' end of the cDNA, an M13 probe corresponding to the 5 end of λdT-7 was used to screen a rat brain "5'-stretch" cDNA library (purchased from Clontech). Replicate filters were hybridized in 50% formamide containing 1×10⁶ cpm/ml of the probe. Of the 5×10⁵ plaques screened, six positive clones were plaque purified and eluted in 0.2 ml buffer containing 100 mM NaCl, 8 mM MgSO$_4$, 50 mM Tris-HCl at pH 7.5, and 0.01% (w/v) gelatin. A primer corresponding to the right arm or left arm of λgt10 sequences flanking the unique EcoR1 cloning site was used in combination with a primer derived from the 5' end of the rat protein farnesyl transferase cDNA (λdT-7) for a PCR reaction. PCR products were analyzed on an agarose gel, and the clone containing the longest extension, λRB-23, was subcloned for further analysis.

d. Expression Vectors

Expression vectors for the α subunit of rat farnesyl transferase were constructed in pCMV5, a plasmid that contains the promoter-enhancer region of the major immediate early gene of human cytomegalovirus (Andersson et al., 1989). A PvuII fragment containing 20 base pairs of the 5' untranslated region and the entire coding region was excised from clone λRTH-B and ligated into SmaI-digested pCMV5 in both orientations. Plasmid λRTH-B is identical to λRTH except for the presence of an intron in the 5'-untranslated region at nucleotide position 39, upstream of the PvuII site at position 37–42. The resulting plasmids designated pFT-α (correct orientation) and pFT-αrev (reverse orientation), were characterized by restriction mapping.

Expression vectors for the β-subunit of rat farnesyl transferase were also constructed in pCMV5 (Andersson et al., 1989). An EcoR1 fragment containing the entire 5' untranslated region and the coding region of farnesyl transferase β subunit cDNA was excised from clone λRB-23 and ligated into EcoR1-digested pCMV5 in both orientations. The resulting plasmids, designated pFT-β1 (correct orientation) and pFT-β1rev (reverse orientation), were characterized by restriction mapping.

e. DNA Transfection

Human embryonic kidney 293 cells were grown in monolayer at 37° C. in medium A (Dulbecco's modified Eagle medium supplemented with 10% (v/v) fetal calf serum, 100 units/ml of penicillin, and 100 μg/ml streptomycin). On day 0, 6×10⁵ cells/100-mm dish were seeded in medium A. On day 1, each dish of cells was transfected with 3 μg of the indicated plasmid plus 1 μg of pVA (a plasmid encoding adenovirus VA RNA$_f$; Akusjä et al., 1987) by the calcium phosphate method (Sambrook et al., 1989). On day 2, the cells received fresh medium A. On day 4, the cells from two dishes were harvested, pooled, and disrupted by repeated aspiration at 4° C. through a 25-gauge needle in 0.4 ml buffer containing 50mM Tris-HCl at pH 7.5, 50 μM ZnCl$_2$, 3 mM MgCl$_2$, 20 mM KCl, 1 mM dithiothreitol, and 0.4% (w/v) octyl-β-glucopyranoside. A cytosolic extract was obtained by centrifugation at 100,000× g for 1 h at 4° C., after which 0.16 to 5.4 μg of the supernatant fraction were assayed for farnesyl transferase activity by measuring the amount of [³H]farnesyl transferred from [³H]farnesyl pyrophosphate to p21$^{H-ras}$ protein as described above.

2. Results a. α subunit Cloning and Sequence Analysis

Degenerate oligonucleotide probes encoding the 5' and 3' ends of a tryptic peptide derived from the farnesyl transferase α subunit were used as primers in a PCR employing rat genomic DNA (FIG. 16A). The sequence of the amplified product was used as a probe to screen a random hexanucleotide-primed rat brain cDNA library cloned in λgt10. This procedure yielded λRB-17, which extended from a poly A tract up to nucleotide position 345 (this position refers to the final sequence of the mRNA, as in nucleic acids 1 through 1680 of seq id no:2).

The 5'-end of the MRNA encoding the α subunit was found to contain a sequence extremely rich in GC basepairs (76% GC from nucleotides 71 to 205 and 90% GC from nucleotides 116 to 145). Multiple attempts to traverse this region by primer extension using reverse transcriptase gave products that terminated prematurely, or that encoded unspliced introns. Therefore, other strategies were employed in order to obtain the 5'-end of the mRNA (see above methods section for detailed protocols). A composite of the cDNA sequences thus obtained was used to generate the overall sequence of the mRNA (seq id no:2).

The mRNA was found to encode a protein of 377 amino acids (seq id no:1) with a calculated molecular weight of 44053. Although the cDNA sequence did not contain a terminator codon upstream of the first methionine codon, it is believed that this methionine represented the true initiator codon. This is supported by transfection studies, in which the recombinant protein produced was observed to have a molecular weight that was indistinguishable on immunoblots from that of the purified rat brain α subunit (see below and FIG. 20). If the cDNA were incomplete, the initiator methionine must be upstream of the 5 end of the sequence obtained, and therefore the protein produced by the cDNA should be at least 2 kDa smaller than the authentic protein. Such a difference should have been detected in gel electrophoresis experiments.

The most remarkable feature of the α subunit cDNA was determined to be a string of 9 consecutive proline residues near the NH$_2$-terminus (in nucleic acids 1 through seq id no:2), whose codons accounted for much of the extreme GC-richness of this region. The mRNA contained sequences corresponding to sequences of the peptides obtained following tryptic digestion of the purified α subunit. Discrepancies only occurred at positions that were assigned tentatively in sequencing trace amounts of protein (see Table I). Some slight homology has been noted between the rat α subunit amino acid sequence and yeast RAM2, the sequence of which is reported in He et al. (1991). The residues of the rat α subunit amino acid sequence (seq id no:1) which are identical to those of the yeast RAM2 sequence are boxed in FIG. 17.

Recently, Kohl et al. have reported the cloning of a partial cDNA clone corresponding to the bovine α subunit of farnesyl transferase (Kohl et al., 1991). The 329 amino acids encoded by this partial clone are 95% identical to the corresponding region in the α subunit of the rat farnesyl transferase. Comparison of the complete amino acid sequence of rat farnesyl transferase α subunit (377 amino acids) with that of the yeast RAM2 gene product (316 amino acids) disclosed by He et al. (1991) reveals that the two proteins are 39% identical in the COOH-terminal 211 residues, suggesting that RAM2 is the yeast counterpart of the α subunit of mammalian farnesyl transferase.

b. β subunit Cloning and Analysis

A unique DNA sequence encoding a portion of the β subunit of the rat farnesyl transferase was obtained by the polymerase chain reaction (PCR) with rat genomic DNA and degenerate oligonucleotide primers (primers β1 and β2; seq id no:60 and 61, respectively) corresponding to potential sequences encoding a tryptic peptide obtained from the purified rat brain enzyme (FIG. 16B). Two unique oligonucleotides (primers B3 and B4, residues 1–17 and 12–36 of seq id no:62, respectively) were synthesized based on the sequence of the amplified product (FIG. 16B). These primers were then used in a 3'-end amplification strategy (Frohman et al., 1988) to obtain an amplified fragment from cDNA prepared from mRNA isolated from cultured rat kidney cells (KNRK cells). This fragment was used to generate probes that identified a bacteriophage containing a near full-length cDNA (λdT-7) from a cDNA library prepared from rat pheochromocytoma PC12 cells. Finally, a fragment from the 5'-end of λdT-7 was used to identify a clone containing a full-length farnesyl transferase β subunit cDNA (λRB-23) from a rat brain cDNA library (seq id no:4).

The cDNA for the rat brain farnesyl transferase β subunit contains 59 base pairs of 5' untranslated region followed by protein-coding region of 1314 base pairs and a 3' untranslated region of 1091 base pairs (seq id no:4). The cDNA encoded a protein of 437 amino acids (seq id no:3) and contained sequences corresponding to sequences of the peptides obtained following tryptic digestion of the purified rat brain farnesyl transferase β subunit. Although certain minor discrepancies in sequence between the protein and the cDNA were apparent, these occurred near the COOH-termini of the peptides and were attributed to ambiguities in sequencing the trace amounts of peptide that were available (see Table I).

The cDNA clones did not contain an inframe terminator codon upstream of the first methionine (amino acid residue 1 in seq id no:3). This is believed to be the initiator methionine as it lies in a good context for initiation according to Kozak's rules (Kozak, 1984) and because the cDNA encodes a protein of the same size as the β-subunit when transfected into animal cells (see below). Although λdT-7 was obtained from an oligo-dT primed cDNA library, the clone did not contain a poly A tract, nor did it contain a consensus polyadenylation sequence. However, RNA blot hybridization experiments and expression studies (see below) suggested that the clone is essentially full-length.

The molecular weight of the β subunit of the rat brain farnesyl transferase was calculated to be 48,679. The amino acid composition did not show any particularly remarkable features and the calculated isoelectric point was 5.99. An analysis of the hydrophobicity plots did not reveal any extensive hydrophobic sequences.

A search of the GenBank and EMBL data banks revealed significant resemblance to two proteins, the DPR1-RAM1 protein of yeast Saccharomyces cerevisiae and a yeast open reading frame of unidentified function (ORF2). Extensive stretches of identity were evident between the β subunit protein sequence and the yeast DPR1-RAM1 gene product (FIG. 18). Sequence conservation was observed throughout the two proteins (overall identity: 37%), but was found to lessen at both ends, and the yeast protein was shorter by six amino acids. The residues of the rat β subunit amino acid sequence (seq id no:3) which are identical to those of the yeast DPR1-RAM1 sequence are boxed in FIG. 18.

In an article by Kohl et al. (1991), in a note added in proof, it is indicated that the β-subunit of bovine farnesyl transferase has been cloned and that it shares 96% homology to the rat β-subunit. However, no actual sequences corresponding to the β-subunit are disclosed by Kohl et al. (1991).

c. Northern Blotting Analyses

Figure 19B:
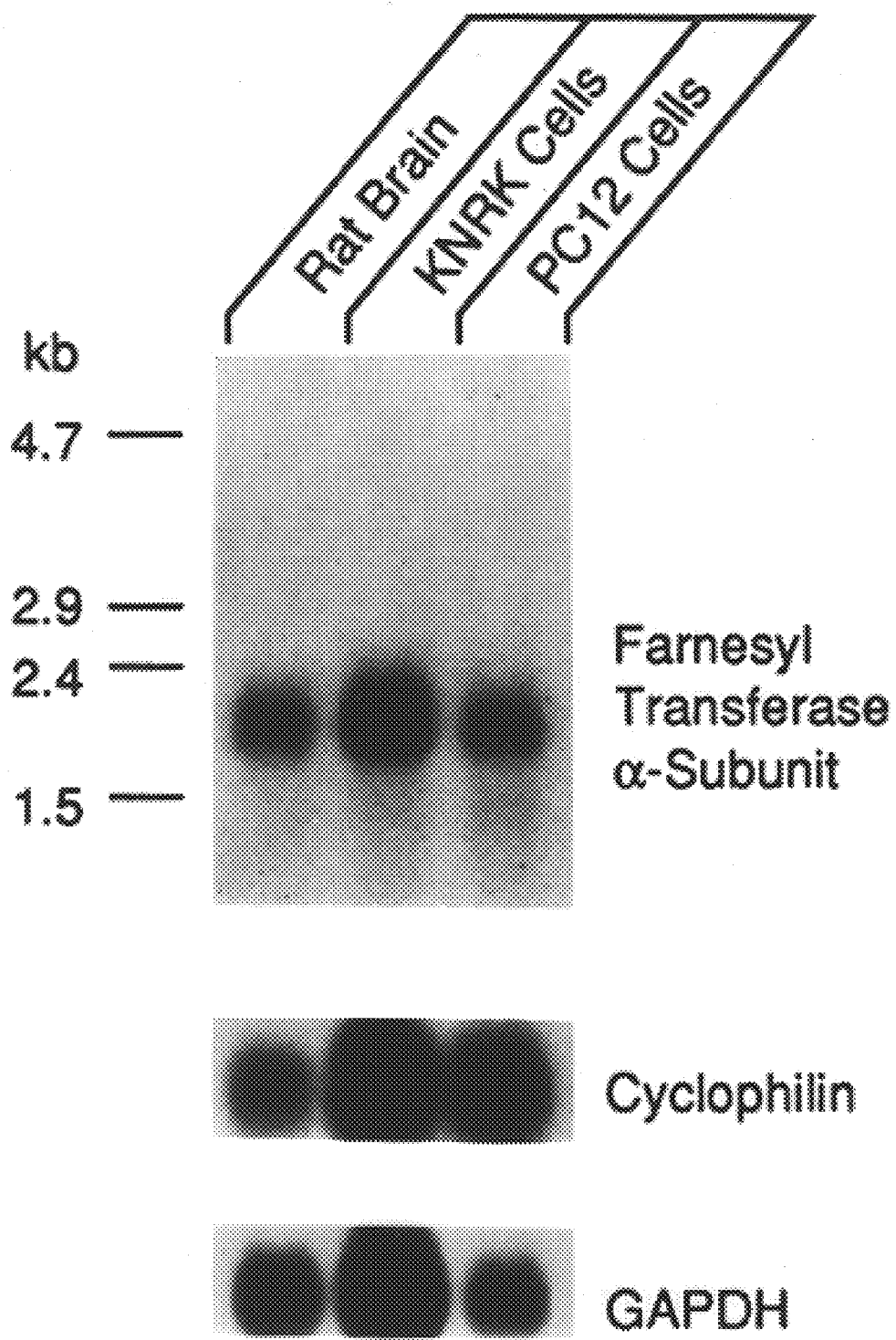

Northern RNA blot analysis with $^{32}$P-labelled probes derived from the α subunit cDNA revealed a single mRNA of ~1.75 kb in multiple rat tissues, including lung, heart, kidney, brain, adrenal, and testis (FIG. 19A). The amount of mRNA in testis was several-fold higher than in any other tissue, an observation that was repeated on several occasions. An MRNA of the same size was also observed in two lines of cultured rat cells derived from kidney (KNRK cells) and adrenal medulla (PC12 cells) (FIG. 19B).

Figure 19C:
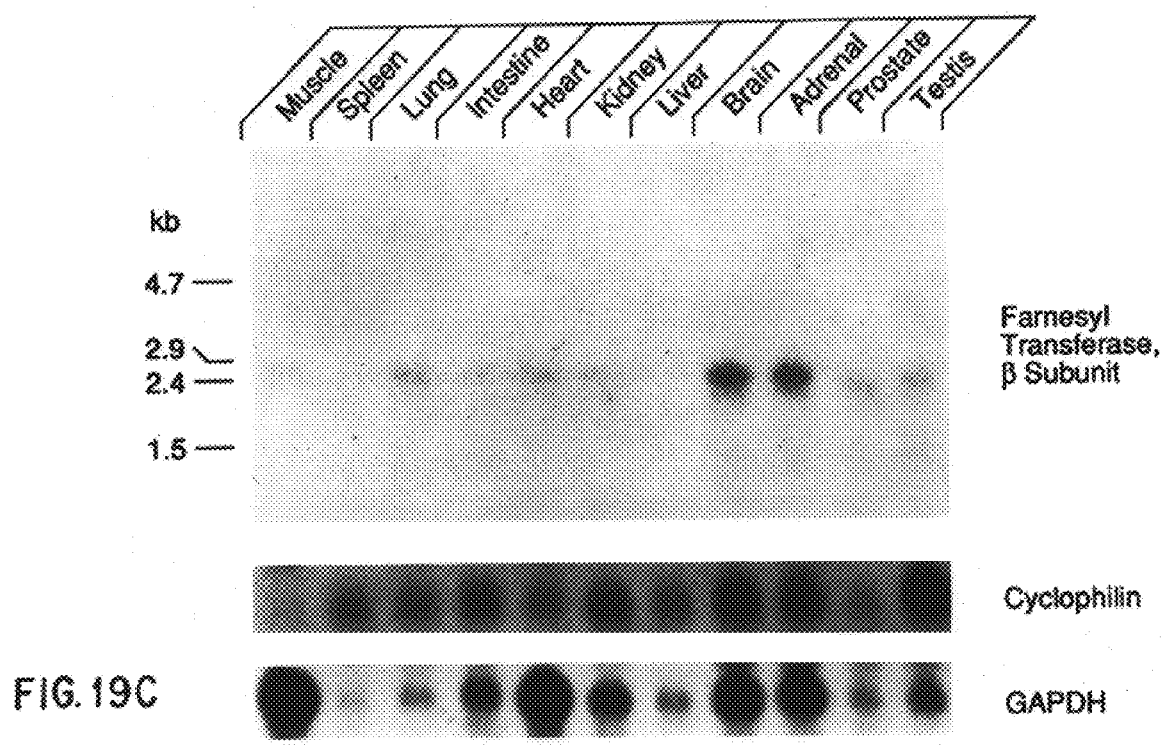

Northern RNA blot analysis with $^{32}$P-labelled probes derived from the β subunit cDNA revealed a hybridizing mRNA of ~2.5 kb in all rat tissues examined except liver and spleen (FIG. 19C). Adequate amounts of mRNA from these tissues were applied to the filter as confirmed by hybridization with control probes for cyclophilin and glyceraldehyde-3-phosphate dehydrogenase. The brain and adrenal gland appeared to have somewhat more mRNA for farnesyl transferase β-subunit than did the other tissues. More quantitative studies will be required to determine whether the variations shown in FIG. 19C are significant.

Figure 19D:
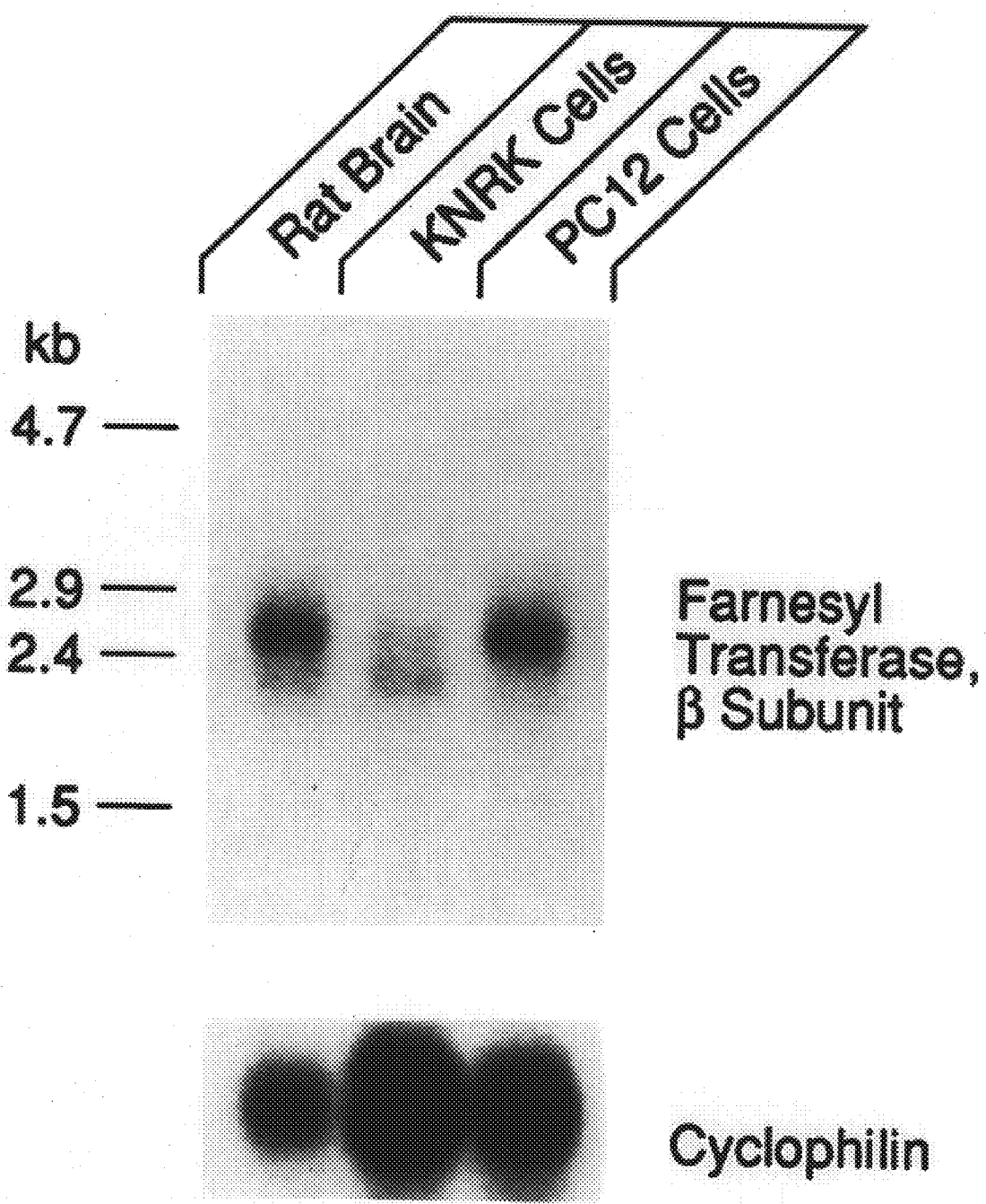

The MRNA for the farnesyl transferase β-subunit was also found in the two cultured rat cell lines from which cDNA sequences had been obtained (FIG. 19D). PC12 cells had the 2.5-kb transcript, whereas the KNRK cells had two transcripts, one of which was smaller than the 2.5-kb MRNA (FIG. 19D). It was not determined whether the smaller transcript represented another gene product that cross-hybridized with the P-subunit probe, or whether this MRNA represented alternative processing of an allelic transcript.

d. Co-Expression and Stability

The cDNA coding regions of both the α and β subunits were cloned into pCMV mammalian expression vectors in either the correct or the reverse orientation. The cDNAs were introduced into human kidney 293 cells by calcium phosphate-mediated transfection, and the proteins were detected by immunoblotting with specific antibodies against the α and β subunits. In both cases, the cDNA directed the expression of proteins with molecular weights that were indistinguishable on immunoblots from those of the purified rat brain farnesyl transferase α and β subunits (FIG. 20).

Figure 20A:
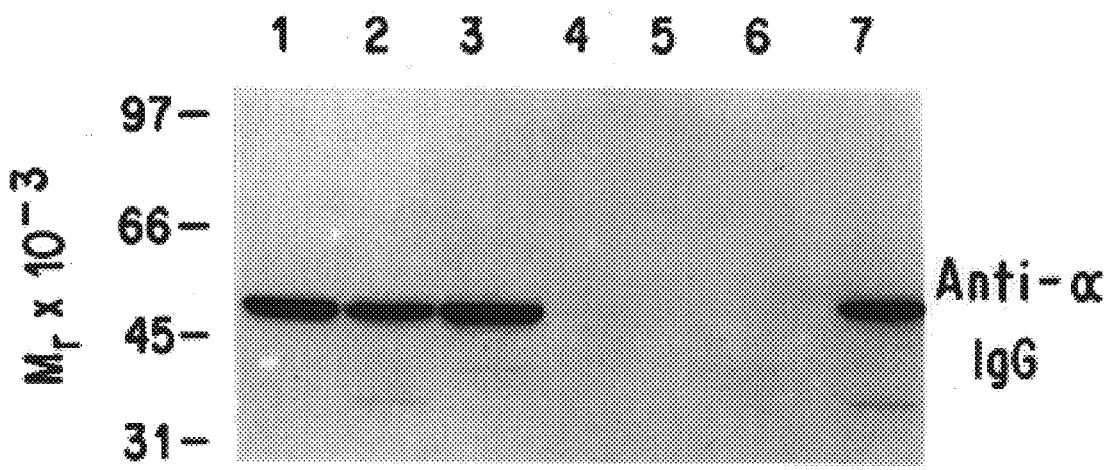
FIG. 20. Immunoblot Analyses of α and β-subunits of Rat Protein Farnesyl Transferase Expressed in Transfected 293 cells. Samples were subjected to SDS/PAGE on 10% gels and transferred to nitrocellulose. The filters were incubated with either 1 μg/ml of rabbit anti α subunit IgG-Y533 (A) or 5 μg/ml of rabbit anti β subunit IgG-X287 (B) followed by incubation with ¹²⁵I-labeled goat anti-rabbit IgG (1×10⁶ cpm/ml). Lanes 1 and 3, 20 μg of partially purified Mono Q fraction of rat brain farnesyl transferase. Lanes 2,4,5,6.7, 20 g of cytosol from 293 cells transfected with the following plasmids: pFT-α plus pFT-β1 (lanes 2 and 7); pFT-α plus pFT-β1rev (lane 4); pFT-αrev plus PFT-β1 (lane 5); pFT-αrev plus pFT-β1rev (lane 6). The filters were exposed to Kodak XAR-5 film for 48 h (A) or 16 h (B) at −700° C. Molecular weight markers are indicated. Plasmids pFT-αrev and pFT-β1rev contain cDNAs inserted in the reverse (noncoding) orientation.
Figure 20B:
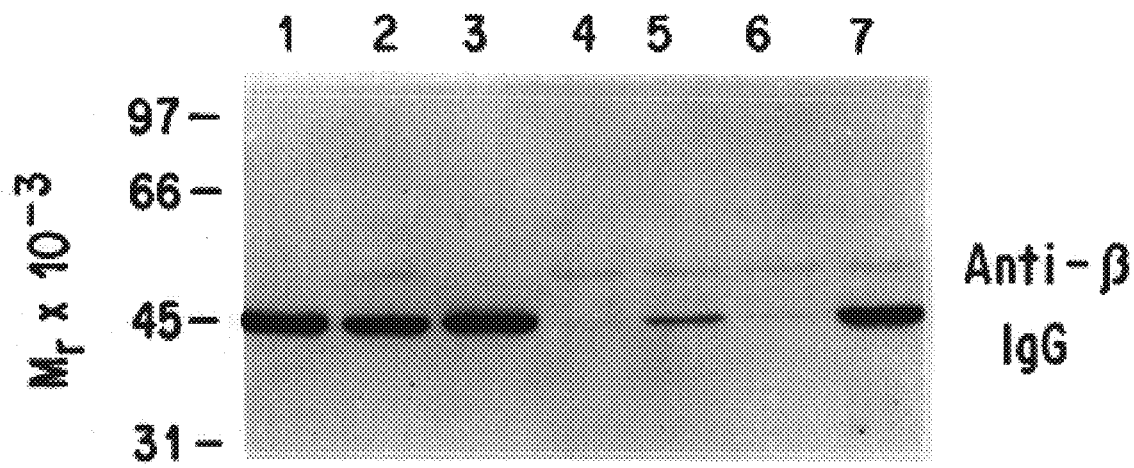
Figure 21:
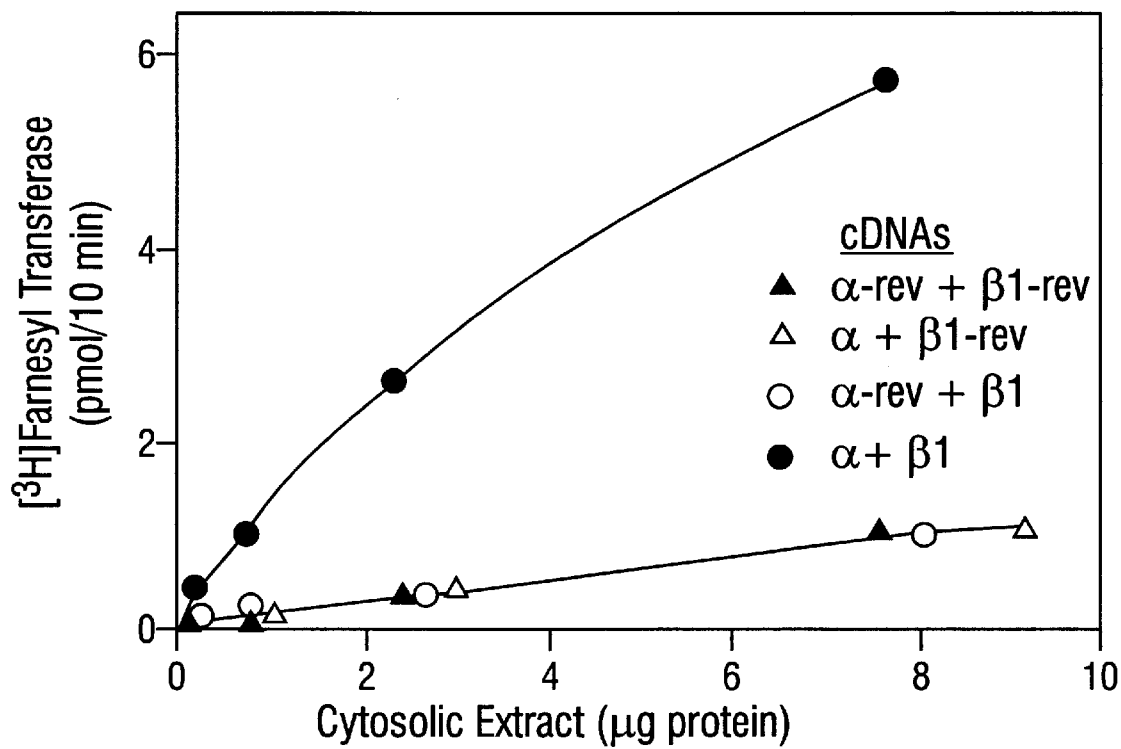
FIG. 21 Farnesyl Transferase Activity of Cytosolic Extracts from 293 cells Transfected with cDNAs Encoding the α and β Subunits of Rat Protein Farnesyl Transferase in the Correct or Reverse (rev) Orientations. Cells were transfected with 3 μg of the indicated plasmid plus 1 μg pVA. Each assay contained in a final volume of 25 μl the indicated amount of cytosolic extract, 50 mM Tris-chloride (pH 7.5), 50 μM ZnCl₂, 20 mM KCl, 3 mM MgCl₂, 1 mM dithiothreitol, 0.4% (v/v) octyl-β-glucopyranoside, 40 μM p21$^{H-ras}$, and 15 pmol of all-trans [³H]farnesyl pyrophosphate (15,335 dpm/pmol). Assay tubes were incubated at 37° C. for 10 min, after which the amount of [³H]farnesyl attached to p21$^{H-ras}$ was measured. Each value is the average of duplicate incubations.

The accumulation of detectable amounts of α subunit required simultaneous transfection with a properly oriented cDNA encoding the β-subunit (FIG. 20A). Similarly, the amount of detectable β-subunit was increased by transfection with the α subunit cDNA in the correct orientation (FIG. 20B). Transfection with the two cDNAs in the correct orientation was also required in order to produce significant amounts of p21$^{ras}$ farnesyl transferase activity as measured in cytosolic extracts (FIG. 21).

3. Discussion

The delineation of the amino acid sequence of the α subunit has not yet allowed its catalytic role to be precisely identified. Homology searches of protein databases failed to reveal significant resemblance of the α subunit to other proteins except for proteins that contain long stretches of prolines. These include such apparently unrelated proteins as the catalytic subunits of rat and human protein phosphatase 2B, mouse retinoblastoma-associated protein ppl05, and *Dictyostelium discoideum* protein tyrosine kinase-1. The α subunit does not bear significant structural resemblance to known prenyltransferases such as mammalian farnesyl pyrophosphate synthetase or yeast hexaprenyl pyrophosphate synthetase.

Present evidence suggests that the α subunit may be shared with another prenyltransferase with a different β subunit that exhibits geranylgeranyltransferase activity (Seabra et al., 1991). If the shared α subunit is stable only as a complex with one of several β subunits, this mechanism would assure that cells maintain only enough α subunits to satisfy all of the β subunits, thereby avoiding accumulation of excess α subunits, which might be toxic (Chen et al., 1991).

The above data reveal that the α and β subunits of the rat farnesyl transferase do not exhibit farnesyl transferase activity when expressed by themselves in transfected human 293 cells. However, co-expression of the two subunits results in the production of an active enzyme. Such expression data provides support for the previous conclusion that the farnesyltransferase is a heterodimer that requires both the α and β subunits for catalytic activity (Chen et al., 1991).

Furthermore, the transfection experiments indicate that mammalian cells will not accumulate high levels of either subunit of the farnesyltransferase unless the other subunit is present. This is particularly true for the α subunit, whose accumulation was nearly completely dependent on co-expression of the β subunit. It is likely that the α subunit is rapidly degraded unless the β subunit is present. However, until pulse-chase labeling experiments are performed, the possibility of control at the level of mRNA stability or translation cannot be ruled out.

The similarity between the rat β subunit and the previously reported sequence of the yeast DPR1-RAM1 gene product (Goodman et al., 1990) indicates that the latter is the yeast equivalent of the peptide-binding subunit of the mammalian farnesyl transferase. These findings confirm the previous suspicion that the yeast gene encodes one of the subunits of the farnesyl transferase and explains the failure of this protein to exhibit farnesyl transferase activity when expressed alone in *E. coli* (Goodman et al., 1988; Schafer et al., 1990).

Mutations at a second locus, designated RAM2, also disrupt farnesyl transferase activity in yeast (Goodman et al., 1990). The defect in the RAM2 cells is complemented by mating with the DPR1-RAM1 mutant. This finding suggests that the RAM2 gene product is the α subunit of the yeast farnesyl transferase. A more recent report of He et al. (1991) indicates that coexpression of the RAM1 and RAM2 genes in *E. coli* provided extracts that farnesylated synthetic a-factor substrate. However, when extracts from separate clones were mixed, only partial farnesyl transferase activity, on the order of about 3.5%, was recovered.

An inspection of the conserved sequences in the rat β subunit and the DPR1-RAM1 protein fails to reveal any obvious candidates for the peptide binding site. The rat protein (residues 35–41) does contain the sequence LXD-DXXE (seq id no:70), which resembles a sequence in four polyprenyl synthetases in which Ile, Leu or Val precedes the XDDXXD sequence (residues 2–7 of seq id no:70) that is believed to be a prenyl pyrophosphate binding site (Ashby and Edwards, 1990). This sequence is not found in the same position in the DPR1-RAM1 protein, and its significance in the β subunit is uncertain. Although the farnesyl transferase reaction requires two divalent cations ($Mg^{++}$ and $Zn^{++}$), the sequence of the β subunit does not reveal any obvious metal binding sites.

Recently, the inventors have explored the separate catalytic roles of $Zn^{2+}$ and $Mg^{2+}$ and the specificity of the prenyl pyrophosphate binding site of the rat brain protein farnesyltransferase, using a purified enzyme preparation. In summary, it was found that the binding of p21$^{H-ras}$ to the enzyme was abolished by dialysis against EDTA and restored by addition of $ZnCl_2$ as demonstrated by chemical crosslinking. The binding of the other substrate, all-trans farnesyl pyrophosphate, was independent of divalent cations, as demonstrated by gel filtration. Transfer of the enzyme-bound farnesyl group to the bound p21$^{H-ras}$ required $Mg^{2+}$. Geranylgeranyl pyrophosphate bound to the prenyl pyrophosphate binding site with an affinity equal to that of farnesyl pyrophosphate, but the geranylgeranyl group was not transferred efficiently to P21$^{H-ras}$. It also was not transferred to a modified p21$^{H-ras}$ containing COOH-terminal leucine, a protein that was shown previously to be a good substrate for a rat brain geranylgeranyltransferase (Seabra et al., 1991). The inventors conclude that the protein farnesyltransferase is a metalloenzyme that most likely contains $Zn^{2+}$ at the peptide-binding site. It thus resembles certain metallopeptidases, including carboxy-peptidase A and the angiotensin-converting enzyme. Strategies previously developed to screen for inhibitors of those enzymes will likely aid in the search for inhibitors of the protein farnesyltransferase.

Thus, these data establish several new points about the enzymology of the protein farnesyltransferase from rat brain: 1) the enzyme contains a tightly bound divalent cation, most likely $Zn^{2+}$, that can be removed by dialysis against EDTA; 2) $Zn^{2+}$ is essential for binding of the peptide substrate, and therefore it is probably attached to the β-subunit; 3) the enzyme binds FPP and GGPP with comparable affinities, but transfers only the farnesyl group and only to an acceptor whose CaaX sequence ends in methionine, serine, glutamine, or cysteine, but not leucine; 4) binding of prenyl pyrophosphates does not require any cation; and 5) transfer of the bound farnesyl group to the bound peptide acceptor requires $Mg^{2+}$.

Figure 22:
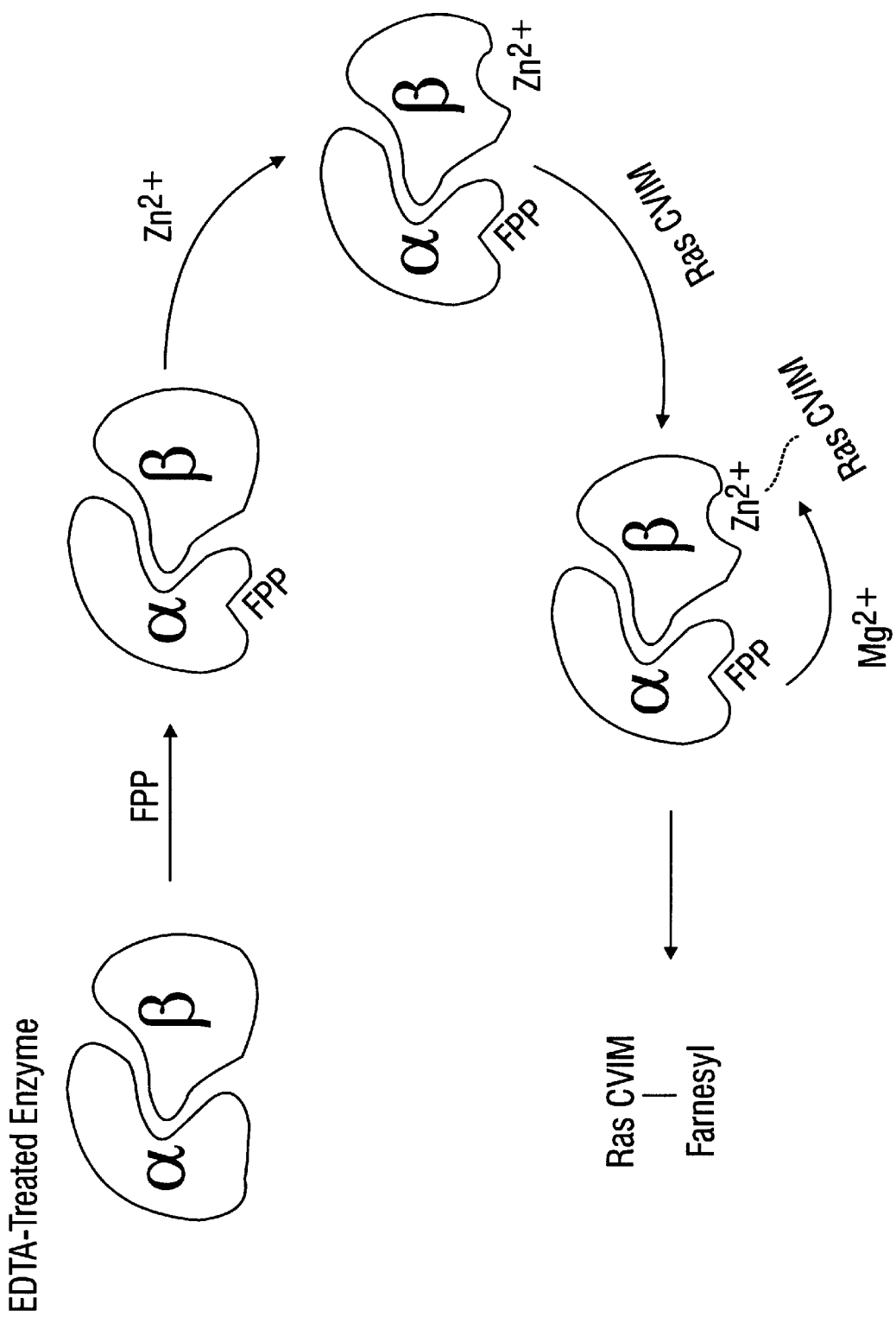
FIG. 22 Schematic Diagram of the Reaction Sequence for EDTA-treated Protein Farnesyltransferase.

The reaction sequence for the EDTA-treated protein farnesyltransferase is summarized graphically in FIG. 22. The EDTA-treated enzyme binds FPP without a requirement for prior $Zn^{2+}$ binding. Peptide binding requires $Zn^{2+}$, but is independent of FPP binding. After both substrates are bound, the transfer reaction occurs in a $Mg^{2+}$- dependent fashion. In the cell the enzyme is expected to be constitutively complexed with $Zn^{2+}$. Under these conditions the mechanism is a simple random-ordered, two-substrate reaction in which the FPP and peptide acceptor can bind to the enzyme in any order.

The requirement for Zn2+ in peptide binding is reminiscent of the requirement for $Zn^{2+}$ in certain metallopeptidases, such as carboxypeptidase A (Lipscomb, 1974). In this case the $Zn^{2+}$ coordinates with the carbonyl and amino groups in the peptide bond that will be broken. In the farnesyltransferase the $Zn^{2+}$ is likely to coordinate with the cysteine sulfhydryl group on the acceptor peptide. If this postulated mechanism is correct, inhibitors that mimic peptides that coordinate with $Zn^{2+}$ might be effective inhibitors of the farnesyltransferase. This strategy would be very similar to the strategy followed in the design of inhibitors of the angiotensin-converting enzyme, a zinc metalloenzyme that is mechanistically similar to carboxypeptidase A (Petrillo and Ondetti, 1982).

The ability of GGPP to compete with FPP for the prenyl pyrophosphate binding site on the protein farnesyltransferase creates potential regulatory problems for the cell. If the intracellular concentrations of FPP and GGPP are similar, then the farnesyltransferase might be competitively inhibited at all times. It seems likely that the concentration of GGPP in the cell is lower than that of FPP. FPP is an intermediate in the synthesis of cholesterol, which is the bulk product of the pathway (Goldstein and Brown, 1990). GGPP, on the other hand, is not known to be converted into any other metabolites in animal cells, and indeed its existence in animal cells was not appreciated prior to the discovery of geranylgeranyl-modified proteins (Farnsworth et al., 1990; Rilling et al., 1990). Thus, it seems likely that cells avoid GGPP competition by maintaining the FPP concentration at a higher level than the GGPP concentration.

If the α subunit is involved in prenyl phrophosphate binding and if the α subunit of the farnesyltransferase is identical to that of the leucine-recognizing geranylgeranyltransferase, then the α subunit must behave differently when it is part of the geranylgeranly-transferase. It seems unlikely that the geranylgeranyl-transferase would be inhibited by FPP because this would render the enzyme functionally inactive in the cell. Resolution of this issue will require the purification of the leucine-recognizing geranylgeranyltransferase and the determination as to whether its α subunit is identical to, or merely similar to, the α subunit of the farnesyltransferase.

The binding of prenyl pyrophosphates to the farnesyltransferase appears to be independent of divalent cations. In this regard the farnesyltransferase resembles the prenyltransferase that catalyzes the condensation of isopentenyl pyrophosphate with allylic pyrophosphates to form FPP (King and Rilling, 1977). The two enzymes also resemble each other in the requirement for a divalent cation ($Mg^{2+}$ or $Mn^{2+}$) in the transfer reaction. In studies not shown, it was found that $Mn^{2+}$ will substitute for $Mg^{2+}$ in the protein farnesyltransferase reaction. The two enzymes differ in that the FPP synthetase is a homodimer and it shows no requirement for $Zn^{2+}$ (Rilling, 1985).

Turning to the issue of the yeast counterpart prenyl transferases, very recently two additional putative β subunits of yeast prenyltransferases have been identified, BET2 (Rossi et al., 1991) and CAL1 (Ohya et al., 1991). Both sequences resemble the DPR1/RAM1 gene product and the β subunit of the rat brain farnesyl transferase. A mutation in the BET2 gene prevents the membrane attachment of two small GTP binding proteins (YPT1 and SEC4) that direct vesicular traffic in the yeast secretory pathway (Rossi et al., 1991). These proteins terminate in the sequence CC, which has recently been shown to be geranylgeranylated in animal cells (Khosravi-Far et al., 1991). The second putative β-subunit, encoded by the CAL1 gene, is necessary for yeast to control the cell cycle when deprived of calcium. Based on a genetic argument, it has been suggested that the targets for this prenyltransferase are two proteins that end in a Cys-X-X-Leu (seq id no:71) sequence and are believed to be geranylgeranylated (Ohya et al., 1991).

Considered together, the yeast and animal experiments suggest the existence of a family of closely related β subunits that mediate peptide binding to a variety of prenyltransferases. Whether all of these enzymes have the same α subunit, or whether a family of such subunits also exists, remains to be determined.

EXAMPLE IV

Recombinant Cloning of the Human Farnesyl:protein Transferase α and β Subunit cDNAs The inventors have now succeeded in cloning cDNAs encoding both the α and β subunits of the human farnesyl-:protein transferase. This was carried out using molecular cloning techniques with the aid of the information gained from the rat farnesyl:protein transferase gene disclosed herein.

1. α subunit Cloning and Sequence Analysis

Approximately $1\times10^6$ plaques from a human retinal λgt10 cDNA library (obtained from Jeremy Nathans, Johns Hopkins University Medical School, Baltimore, Md.) were screened using $^{32}$P-labeled probes corresponding to the 5' end of the cDNA for the rat farnesyl transferase α subunit, as disclosed herein and in Chen et al., (1991a). Filters were hybridized at 42° C. in hybridization buffer with 50% (v/v) formamide containing $1\times10^6$ cpm/ml of a single-stranded M13 probe and washed in IXSSC (150 mM sodium chloride and 15 mM sodium citrate, pH7) and 0.5% (w/v) SDS at 55° C.

On screening the human retinal cDNA library with $^{32}$P-labeled probes derived from the rat α subunit cDNA, several positive clones were identified. These were initially characterized by polymerase chain reaction (PCR) using primers corresponding to the right and left arms of λgt10. Positive clones containing the largest inserts were plaque purified, phage DNA prepared, and the cDNA inserts subcloned into the Bluescript (Stratagene) SKII vector for restriction mapping and DNA sequencing (Sanger et al., 1980) using specific oligonucleotides.

The nucleotide sequence of the human farnesyltransferase α subunit, as encoded by the cloned cDNA, is represented by seq id no:6. This coding region is followed by a 3'-untranslated region of 524 nucleotides that ends in a poly(A) tail. The cloned cDNA encodes a human α subunit protein of 379 amino acids, represented by seq id no:5, which is two amino acids longer than the deduced rat sequence (FIG. 23A, FIG. 23B, FIG. 23C and FIG. 23D.) Overall, the human farnesyltransferase α subunit is 93% identical to the rat α subunit at the protein level (FIG. 23A, FIG. 23B, FIG. 23C and FIG. 23D.) In the coding region, the nucleotide sequence of the human cDNA is 79% identical to that of the rat.

When introduced together into the human kidney 293 cell line by transfection, the human farnesyltransferase α subunit cDNA and the rat farnesyltransferase β subunit cDNA produced an active enzyme, as was the case when the cDNAs encoding both of the rat subunits were co-transfected into 293 cells (disclosed herein).

2. β subunit Cloning and Sequence Analysis

PCR was used to produce a probe specific for the human farnesyltransferase β subunit. Human prostate poly (A)+ RNA was subjected to first strand synthesis (Chen et al. 1991a; 1991b), and then used as a template in a PCR reaction with a primer pair developed from the rat farnesyl transferase β subunit, as disclosed herein and in Chen et al., (1991b). The 300 bp amplified product was sequenced and shown to correspond to the human farnesyl transferase β subunit.

On screening 1.5×10$^6$ plaques from the human retinal λgt10 cDNA library with the $^{32}$P-labeled probe corresponding to the PCR-product, 9 positive clones were identified. Positive clones containing the largest inserts were plaque purified, phage DNA prepared, and the cDNA inserts subcloned into M13 and pUC18 vector for restriction mapping and DNA sequencing (Sanger et al., 1980) using the M13 universal sequencing primer.

The nucleotide sequence of the human farnesyltransferase β subunit, as encoded by the partial cDNA clone obtained, is represented by seq id no:8. This partial cDNA clone encodes a human β subunit protein of 487 amino acids (seq id no:7), 50 amino acids shorter than the deduced rat sequence (FIG. 24A, FIG. 24B and FIG. 24C.) Overall, the human farnesyltransferase β subunit is 96% identical to the rat farnesyltransferase β subunit at the protein level (FIG. 24A, FIG. 24B and FIG. 24C, FIG. 24D.) In the coding region, the nucleotide sequence of the human cDNA (seq id no:8) is 87% identical to the rat sequence (seq id no:4).

3. Discussion

In a disease or disorder where the function of CAAX farnesyl transferase and the related prenyltransferase, CAAX geranylgeranyl transferase, is potentially important, an abnormality of either the α or β subunit of CAAX farnesyltransferase or CAAX geranylgeranyl transferase might either cause or exacerbate the condition. It would appear that mutations in either the α subunit or the β subunit of farnesyltransferase would have pleiotropic effects because of the number of different proteins and systems that are affected by prenylation. Pleiotropy would be expected to be particularly evident in mutations that affect the farnesyltransferase α subunit since this protein is the α subunit for both the CAAK farnesyltransferase and CAAX geranylgeranyl transferase.

Different mutations in critical regions of the α or β subunits of farnesyltransferase may have a differential effect on individual GTP-binding proteins. For p21$^{ras}$ proteins, farnesylation assists attachment of p21$^{ras}$ to the inner surface of the plasma membrane. It is believed that farnesylation increases the efficiency with which oncogenic ras proteins stimulate cell growth. It is possible that amplification or activating mutations of either the α or β subunits of the farnesyltransferase enzyme may affect tumor cell growth and progression indirectly by increasing the attachment efficiency of p21$^{ras}$ proteins.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

Akada, R., et al. (1989), *Mol. Cell. Biol.,* 9:3491–3498.

Akusjärvi, G., Svensson, C., and Nygard, 0. (1987), *Mol. Cell. Biol.* 7, 549–551.

Andersson, S., Davis, D. L., Dahlbäck, H., Jörnvall, H. & Russell, D. W. (1989), *J. Biol. Chem.* 264, 8222–8229.

Ashby, M. N., and Edwards, P. A. (1990), *J. Biol. Chem.* 265, 13157–13164.

Aviv, H., et al. (1972), *Proc. Natl. Acad. Sci. USA,* 69:1408–1412.

Barbacid (1987), *Ann. Rev. Biochem.,* 56:779–827.

Bos, J. (1989), *Cancer Res.,* 49:4682–4689.

Casey, P. J., et al. (1989), *Proc. Natl. Acad. Sci., U.S.A.,* 86:8323–8327.

Chen, W- J., Andres, D. A., Goldstein, J. L., and Brown, M. S. (1991a), *Proc. Natl. Acad. Sci., USA,* 88, 11368–11372.

Chen, W- J., Andres, D. A., Goldstein, J. L., Russell, D. W. and Brown, M. S. (1991b), *Cell* 66, 327–334.

Chirgwin, J. M., et al. (1979), *Biochemistry,* 18:5294–5303. Clarke, E., et al. (1988), *Natl. Acad. Sci. U.S.A.,* 85:4643–4647.

Davisson, V. J., et al. (1986), *J. Org. Chem.,* 51:4768–4779.

Farnsworth, D. C., et al. (1989), *J. Biol. Chem.,* 264:20422–20429.

Farnsworth, C. C., Gelb, M. H., Glomset, J. A. (1990), *Science,* 247, 320–322.

Feig, L. A., et al. (1986), *Proc. Natl. Acad. Sci. U.S.A.,* 83:4607–4611.

Frohman, M. A., et al. (1988), *Proc. Natl. Acad. Sci. USA,* 85:8998–9002.

Gautam, N., et al. (1989), *Science,* 244:971–974.

Gibbs, J. B., et al. (1989), *Micro Rev.,* 53:171–185.

Glisin, V., et al. (1974), *Biochemistry,* 13:2633–2640.

Goldstein, J. L. and Brown, M. S. (1990), *Nature,* 343, 425–430.

Goldstein, J. L., Brown, M. S., Stradley, S. J., Reiss, Y., and Gierasch, L. M. (1991), *J. Biol Chem.,* 266, 15575–15578.

Goodman, L. E., Perou, C. M., Fujiyama, A., and Tamanoi, F. (1988), *Yeast* 4, 271–281.

Goodman, L. E., Judd, S. R., Farnsworth, C. C., Powers, S., Gelb, M. H., Glomset, J. A., and Tamanoi, F. (1990), *Proc. Natl. Acad. Sci. USA,* 87, 9665–9669.

Gutierrez, L., et al. (1989), *Embo J.,* 8:1093–1098.

Hancock, J. F., et al. (1989), *Cell,* 57:1167–1177.

Harlow, E. & Lane, D. (1988), In: *Antibodies: A Laboratory Manual.* Cold Spring Harbour Laboratory Press, NY, pp. 82–83.

He, B., Chen, P., Chen, S. Y., Vancura, K. L., Michaelis, S., and Powers, S. (1991), *Proc. Natl. Acad. Sci. USA,* 88, 11373–11377.

Kamiya, Y., et al. (1978), *Biochem. Biophys. Res. Comm.,* 83:1077–1083.

Kamiya, Y., et al. (1979),*N. Agric. Biol. Chem.,* 43:1049–1053.

Khosravi-Far, R., Lutz, R. J., Cox, A. D., Clark, R., Bourne, J. R., Sinensky, M., Balch, W. E., Buss, J. E., and Der, C. J. (1991), *Proc. Natl. Acad. Sci. USA,* 88, 6264–6268.

King, H. L. and Rilling, H. C. (1977), *Biochemistry,* 16, 3815–3819.

Kohl, N. E., Diehl, R. E., Schaber, M. D., Rands, E., Soderman, D. D., He, B., Moores, S. L., Pompliano, D. L., Ferro-Novick, S., Powers, S., Thomas, K. A., Gibbs, J. B. (1991), *J. Biol. Chem.,* 266, 18884–18888.

Kozak, M. (1984). *Nucleic Acids Res.* 12, 857–872.

Kyte, J., & Doolittle, (1982), *J. Mol. Biol.,* 157:105–132.

Laemmli, U. K. (1970), *Nature,* 227:680–685.

Lee, C. C., et al. (1988), *Science,* 239:1288–1291.

Lehrman, M. A., et al. (1987), *J. Biol. Chem.,* 262:3354–3361.

Lipscomb, W. N. (1974), *Tetrahedron,* 30, 1725–1732.

Lowry, O. H., et al. (1951), *J. Biol. Chem.,* 193:265–275.

Lowry, D. R. et al. (1989), *Nature,* 341: 384–385.

Maxam, A. M., et al. (1980), *Methods Enzymol,* 65:499–560.

Mumby, S. M., et al. (1990), *Proc. Natl. Acad. Sci. USA,* 87:5873–5877.

Ohya, Y., Goebl, M., Goodman, L. E., Petersen-Bjørn, S., Friesen, J. D., Tamanoi, F., and Anraku, Y. (1991), *J. Biol. Chem.,* 266, 12356–12360.

Petrillo, E. W. Jr., Ondetti, M. A. (1982), *Medicinal Res. Rev.,* 2, 1–41.

Reiss, Y., Seabra, M. C., Armstrong, S. A., Slaughter, C. A.,

Goldstein, J. L., and Brown, M. S. (1991), *J. Biol. Chem.,* 266, 10672–10677.

Rilling, H. C. (1985), *Meth. Enzymol.,* 110, 145–152.

Rilling, H. C., Breunger, E., Epstein, W. W., and Crain, P. F. (1990), *Science,* 247, 318–320.

Robishaw, J. D., et al. (1989), *J. Biol. Chem.,* 264:15758–15761.

Rossi, G., Jiang, Y., Newman, A. P., and Ferro-Novick, S. (1991), *Nature,* 351, 158–161.

Saiki, R. K. et al. (1988), *Science,* 239:487–491.

Sakagami, Y., et al. (1981), *Science,* 212:1525–1527.

Sambrook, J., et al. (1989), *Molecular Cloning: A Laboratory Manual,* Cold Spring Harbor Laboratory, Cold Spring Harbor, N.Y.

Sanger, F., et al. (1977), *Proc. Natl. Acad. Sci. USA,* 74:5463–5467.

Sanger, F., Coulson, A. R., Barrell, B. G., Smith, A. J. H. & Roe, B. A. (1980), *J. Mol. Biol.* 143, 161–178.

Schafer, W. R., Trueblood, C. E., Yang, C-. C., Mayer, M. P., Rosenberg, S., Poulter, C. D., Kim, S- H., and Rine, J. (1990), *Science,* 249, 1133–1139.

Scheler, W. R. et al. (1989), *Science,* 248:379–385.

Seabra, M. C., Reiss, Y., Casey, P. J., Brown, M. S., and Goldstein, J. L. (1991), *Cell,* 65:429–434.

Stewart, J. M. et al. (1984), *Solid Phase Peptide Synthesis,* 2nd ed., Pierce Chemical Co., Rockford, Ill.

Tabor, S., et al. (1987), *Proc. Natl. Acad. Sci. USA,* 84:4767–4771.

Yamane, H. K., et al. (1990), *Proc. Natl. Acad. Sci. USA,* 87:5868–5872.

---

What is claimed is:

1. An isolated and purified DNA segment encoding the α subunit or the β subunit or the α and β subunits of mammalian farnesyl:protein transferase.

2. The DNA segment of claim 1, further defined as encoding the α subunit.

3. The DNA segment of claim 2, further defined as encoding the rat farnesyl:protein transferase α subunit.

4. The DNA segment of claim 3, wherein the encoded farnesyl:protein transferase α subunit has the α subunit amino acid sequence as set forth in seq id no: 1.

5. The DNA segment of claim 4, further defined as having the farnesyl:protein transferase α subunit-encoding nucleic acid sequence as set forth in nucleic acids 1 through 1680 of seq id no:2.

6. The DNA segment of claim 2, further defined as encoding the human farnesyl:protein transferase α subunit.

7. The DNA segment of claim 6, where in the encoded farnesyl:protein transferase α subunit has the α subunit amino acid sequence as set forth in seq id no:5.

8. The DNA segment of claim 7, further defined as having the farnesyl:protein transferase α subunit-encoding nucleic acid sequence as set for in nucleic acids 1 through 1638 of seq id no:6.

9. The DNA segment of claim 1, further defined as encoding the β subunit.

10. The DNA segment of claim 9, further defined as encoding the rat farnesyl:protein transferase β subunit.

11. The DNA segment of claim 10, wherein the encoded farnesyl:protein transferase β subunit has the β subunit amino acid sequence as set forth in seq id no:3.

12. The DNA segment of claim 11, further defined as having the farnesyl:protein transferase β subunit-encoding nucleic acid sequence as set forth in seq id no:4.

13. The DNA segment of claim 9, further defined as encoding the human farnesyl:protein transferase β subunit.

14. The DNA segment of claim 13, wherein the encoded farnesyl:protein transferase β subunit has the β subunit amino acid sequence as set forth in seq id no:7.

15. The DNA segment of claim 14, further defined as having the farnesyl:protein transferase β subunit-encoding nucleic acid sequence as set forth in seq id no:8.

16. A plasmid, phage or viral vector comprising a DNA segment in accordance with claim 1.

17. The vector of claim 16, further defined as comprising a DNA segment encoding both a farnesyl:protein transferase α subunit and a farnesyl:protein transferase β subunit.

18. A host cell incorporating a DNA segment in accordance with claim 1 or claim 16.

19. The host cell of claim 18, further defined as incorporating a vector comprising a DNA segment encoding both a farnesyl:protein transferase α subunit and a farnesyl:protein transferase β subunit.

20. The host cell of claim 18, further defined as a eukaryotic host cell.

21. A host cell of claim 18, further defined as a bacterial host cell.

22. A host cell of claim 20, wherein the DNA segment is integrated into the genome of the host cell.

23. The host cell of claim 18, wherein at least one farnesyl:protein transferase subunit is expressed.

24. The host cell of claim 19, wherein both an α and β subunit is expressed.

25. The host cell of claim 24, further defined as expressing biologically active farnesyl:protein transferase.

26. An isolated and purified nucleic acid segment which comprises at least a ten nucleotide long contiguous stretch of the nucleic acid sequence shown in nucleic acids 1 through 1680 of seq id no:2, seq id no:4, nucleic acids 1 through 1638 of seq id no:6 or seq id no:8, or the complement of the nucleic acid sequence shown in nucleic acids 1 through 1680 of seq id no:2: seq id no:4: nucleic acids 1 through 1638 of seq id no:6 or seq id no:8.

27. The nucleic acid segment of claim 26, further defined as comprising a least a fifteen nucleotide long contiguous stretch of the nucleic acid sequence of nucleic acids 1 through 1680 of seq id no:2, seq id no:4, nucleic acids 1 through 1638 of seq id no:6 or seq id no: 8, or the complement of the nucleic acid sequence shown in nucleic acids 1 through 1680 of seq id no:2 seq id no:4: nucleic acids 1 through 1638 of seq id no:6 or seq id no:8.

28. The nucleic acid segment of claim 27, further defined as comprising a least a twenty nucleotide long contiguous stretch of the nucleic acid sequence of nucleic acids 1 through 1680 of seq id no:2, seq id no:4, nucleic acids 1 through 1638 of seq id no:6 or seq id no:8, or the complement of the nucleic acid sequence shown in nucleic acids 1 through 1680 of seq id no:2: seq id no:4: nucleic acids 1 through 1638 of seq id no:6 or seq id no:8.

29. The nucleic acid segment of claim 28, further defined as comprising a least a thirty nucleotide long contiguous stretch of the nucleic acid sequence of nucleic acids 1 through 1680 of seq id no:2, seq id no:4, nucleic acids 1 through 1638 of seq id no:6 or seq id no:8, or the complement of the nucleic acid sequence shown in nucleic acids 1 through 1680 of seq id no:2: seq id no:4: nucleic acids 1 through 1638 of seq id no:6 or seq id no:8.

30. The nucleic acid segment of claim 29, further defined as comprising a least a fifty nucleotide long contiguous stretch of the nucleic acid sequence of nucleic acids 1 through 1680 of seq id no:2, seq id no:4, nucleic acids 1 through 1638 of seq id no:6 or seq id no:8 or the complement of the nucleic acid sequence shown in nucleic acids 1 through 1680 of seq id no:2: seq id no:4: nucleic acids 1 through 1638 of seq id no:6 or seq id no:8.

31. The nucleic acid segment of claim 26, further defined as comprising a nucleic acid fragment of up to 200 basepairs in length.

32. The nucleic segment of claim 31, further defined as comprising a nucleic acid fragment of up to 100 basepairs in length.

33. The nucleic acid segment of claim 32, further defined as comprising a nucleic acid fragment of up to 50 basepairs in length.

34. The nucleic acid segment of claim 26, further defined as a DNA segment.

35. A method for using a DNA segment which encodes the α or β subunit of mammalian farnesyl:protein transferase, the method comprising:

(a) preparing a recombinant host cell which incorporates a DNA segment encoding the α or β subunit of mammalian farnesyl:protein transferase and expressing one or both of said subunits; and (b) culturing the transformed host cell under conditions effective to allow expression of the farnesyl:protein transferase subunit so encoded.

36. The method of claim 35, wherein the recombinant host cell incorporates a DNA segment encoding both the α and β subunit of mammalian farnesyl:protein transferase and is capable of expressing biologically active farnesyl:protein transferase enzyme.

* * * * *

UNITED STATES PATENT AND TRADEMARK OFFICE
CERTIFICATE OF CORRECTION

| | | |
|---|---|---|
| PATENT NO. | : 5,976,851 | Page 1 of 1 |
| DATED | : November 2, 1999 | |
| INVENTOR(S) | : Michael S. Brown et al. | |

It is certified that error appears in the above-identified patent and that said Letters Patent is hereby corrected as shown below:

<u>Title page,</u>
Item [57], ABSTRACT,
Line 17, please delete "families" and insert therefor -- family --.
Item [56], U.S. PATENT DOCUMENTS, please add the following:

| -- 5,104,975 | 4/1992 | McCormick et al. | 530/350 |
| 5,234,839 | 8/1993 | McCormick et al. | 436/501 |
| 5,238,922 | 8/1993 | Graham et al. | 514/18 -- |

<u>Column 51,</u>
Line 23, please delete "for" and insert therefor -- forth --.

<u>Column 52,</u>
Line 8, please delete "a" and insert -- at --.
Line 16, please delete "a" and insert -- at --.
Line 24, please delete "a" and insert -- at --.
Line 32, please delete "a" and insert -- at --.

Signed and Sealed this

Eleventh Day of March, 2003

JAMES E. ROGAN
*Director of the United States Patent and Trademark Office*